United States Patent
Hernández Míguez et al.

(10) Patent No.: US 9,914,768 B2
(45) Date of Patent: Mar. 13, 2018

(54) ANTI-S100A7 ANTIBODIES FOR THE TREATMENT AND DIAGNOSIS OF CANCER

(71) Applicant: LYKERA BIOMED, S.A., Barcelona (ES)

(72) Inventors: José Luis Hernández Míguez, Sant Boi de Llobregat (ES); Jaume Adan Plana, Mataró (ES); Josep Maria Martínez Escolà, Barcelona (ES); Marc Masa Álvarez, Esparreguera (ES); Ramon Messeguer Peypoch, Premià de Mar (ES); Francesc Mitjans Prat, Igualada (ES); Sheila Dakhel Plaza, Esparreguera (ES); Antonio Coll Manzano, Barcelona (ES); Rosa M$^a$ Hervas Villegas, L'Hospitalet de Llobregat (ES); Carme Calvis Calpe, L'Hospitalet de Llobregat (ES); Laura Padilla García, Segur de Calafell (ES); Lourdes Tatiana Roque Navarro, Barcelona (ES); Laura Barberà Ferrando, Jesús-Tortosa (ES); Manuel Rivas Cañas, Sant Boi de Llobregat (ES)

(73) Assignee: Lykera Biomed, S.A., Terrassa, Barcelona (ES)

( * ) Notice: Subject to any disclaimer, the term of this patent is extended or adjusted under 35 U.S.C. 154(b) by 0 days.

(21) Appl. No.: 14/897,108

(22) PCT Filed: Apr. 9, 2014

(86) PCT No.: PCT/EP2014/057213
§ 371 (c)(1),
(2) Date: Dec. 9, 2015

(87) PCT Pub. No.: WO2014/167030
PCT Pub. Date: Oct. 16, 2014

(65) Prior Publication Data
US 2016/0289307 A1     Oct. 6, 2016

(30) Foreign Application Priority Data
Apr. 9, 2013   (EP) ..................................... 13382128

(51) Int. Cl.
| | | |
|---|---|---|
| *A61K 39/395* | (2006.01) | |
| *C07K 16/18* | (2006.01) | |
| *C07K 16/30* | (2006.01) | |
| *G01N 33/574* | (2006.01) | |
| *A61K 47/68* | (2017.01) | |

(52) U.S. Cl.
CPC .......... *C07K 16/18* (2013.01); *A61K 47/6843* (2017.08); *C07K 16/3015* (2013.01); *C07K 16/3046* (2013.01); *C07K 16/3053* (2013.01); *G01N 33/57407* (2013.01); *G01N 33/57415* (2013.01); *G01N 33/57419* (2013.01); *C07K 2317/33* (2013.01); *C07K 2317/73* (2013.01); *C07K 2317/76* (2013.01); *G01N 2333/4727* (2013.01)

(58) Field of Classification Search
None
See application file for complete search history.

(56) References Cited

U.S. PATENT DOCUMENTS

| | | | |
|---|---|---|---|
| 4,619,794 | A | 10/1986 | Hauser |
| 5,591,828 | A | 1/1997 | Bosslet et al. |
| 5,658,570 | A | 6/1997 | Newman et al. |
| 6,113,898 | A | 9/2000 | Anderson et al. |
| 2009/0104618 | A1 | 4/2009 | Polyak et al. |
| 2010/0021472 | A1 | 1/2010 | Srikrishna et al. |

FOREIGN PATENT DOCUMENTS

| | | |
|---|---|---|
| EP | 0052322 | 5/1982 |
| EP | 143949 A1 | 6/1985 |
| EP | 36676 B2 | 9/1990 |
| WO | WO 1993/11161 A1 | 6/1993 |
| WO | WO 2003/057159 A2 | 7/2003 |
| WO | WO 2011/157724 A1 | 12/2011 |
| WO | 03057159 | 7/2013 |

OTHER PUBLICATIONS

Strome et al., The Oncologist, 2007; 12:1084-95.*
Brand et al., Anticancer Res. 2006; 26:463-70.*
Nelson et al., Ann. Intern Med. 2009; 151:727-737.*
Kataja et al., Ann Oncol 2009; 20(sup 4): iv10-14.*
Paul, Fundamental Immunology, 3rd Edition, 1993, pp. 292-295.*
Rudikoff et al (Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Brown et al (J. Immunol. May 1996; 156(9):3285-3291.*
Vajdos et al (J. Mol. Biol. Jul. 5, 2002;320(2); 415-428).*
Tockman et al, Cancer Research vol. 52 p. 2711s (1992).*
Janicke et al Fibrinolysis vol. 4 p. 69 (1990).*
Alowami et al., (2003) Psoriasin (S100A7) expression is altered during skim tumorigenesis. BMC Dermatol, 3:1.

(Continued)

*Primary Examiner* — Sheela J. Huff
(74) *Attorney, Agent, or Firm* — Gary J. Gershik; Cooper & Dunham LLP

(57) ABSTRACT

The present invention relates to the use of antibodies against S100A7 protein for the prevention and/or treatment of cancer or a disease associated to an undesired angiogenesis or a disease associated with inflammation; and to methods and kits for diagnosing and determining the prognostic of said diseases in vitro and in vivo by means of detecting levels of S100A7 in a biofluid, preferably with an antibody. The invention also relates to specific anti-S100A7 monoclonal antibodies, hybridoma cell lines producing them and method for obtaining them, as well as pharmaceutical compositions and conjugates containing them.

17 Claims, 12 Drawing Sheets

(56) References Cited

OTHER PUBLICATIONS

Arumugam T. et al., (2006) Effect of Cromolyn on S100P on Interactions with RAGE and Pancreatic Cancer Growth and Invasion in Mouse Models. J. Nat Cancer Inst. 98:1806-1818.
Barbieri MR. et al., (2011) Expression of human protein S100A7 (psoriasin) preparation of antibody and application to human larynx squamous cell carcinoma. BMC Res Notes;4(1):494.
Celis JE. et al., (1996) Bladder Squamous Cell Carcinomas Express Psoriasin and Externalize it to the Urine. J Urol, 155(6): 2105-2112.
Chothia and Lesk J. (1987) Canonical Structure for the Hypervariable Regions of Immunoglobulins. Mol. Biol. 196:901-917.
Chothia et al., (1989) Conformations of immunoglobulin hypervariable regions. Nature 342:878-883.
Cyranka-Czaja A. et al., (2012) Selection and characterization of human antibody gragments specific for psoriasin—A Biochem Biophys Res Commun, 419(2):250-255.
El-Rifai et al., (2002) Gastric Cancers Overexpress DARPP-32 and a Novel Isoform, t-DARPP[1] Cancer Res., 62:6823-6826.
Epstein et al., (1985) Biological activity of liposome-encapsulated murine interferon γ is mediated by a cell membrane receptor. Proc. Natl. Acad. Sci. USA, 82:3688-3692.
Ethan D. Emberley et al., (2003) S100A7 (psoriasin) expression is associated with aggressive features and alteration of Jab1 in ductal carcinoma in situ of the breast. Clin. Can. Res., 9:2627-2631.
Gagnon et al., (2008) Use of a Combination of Approaches to Identify and Validate Relevant Tumor-Associated Antigens and Their Corresponding Autoantibodies in Ovarian Cancer Patients. Clin. Cancer Res., 14(3): 764-761.
Hollinger et al., (1993) "Diabodies": Small bivalent and bispecific antibody fragments. Proc. Natl. Acad. Sci. USA, 90: 6444-6448.
Hwang et al., (1980) Hepatic uptake and degradation of unilamellar sphingomyelin/cholesterol liposomes: A kinetic study. Proc. Natl. Acad.. Sci. USA, 77:4030-4034.
Kai K et al. (2009) Maintenance of HCT116 colon cancer cell line conforms to a stochastic model but not a cancer stem cell model. Cancer Sci. Dec; 100: 2275-82.
Krop et al., (2005) A putative role for psoriasin in breast tumor progression. Cancer Res., 65:11326-11334.
Mandal S. et al. (2007) S100A7 (psoriasin) influences immune response genes in human breast cancer. Exp Cell Res, 313(14):3016-3025.
Morgan et al., (2011) Psoriasin (S1000A7) associates with integrin β6 subunit and is required for αvβ6-dependent carcinoma cell invasion. Oncogene.; 30:1422-35.
Maubayed et al., (2007) Psoriasin (S100A7) is significantly up-regulated in human epithelial skin tumors. J Cancer Res Clin Oncol, 133:253-61.
Nasser MW. et al., (2012) S100A7 Enhances mammary tumoigensis through upregulation of inflammatory pathways. Cancer Res, 72(3): 604-615.
Newman et al., (1992) "Primatization" of recombinant antibodies for immunotherapy of human diseases: a maxaque/human chimeric antibody against human CD4. Biotechnology, 10:1458-1460.
Ostergaard M et al., (1997) Proteome Profiling of Bladder Squamous Cell Carcinomas: Identification of Markers That Cancer Res Clin Oncol, 133:253-61.
Paruchuri et al., (2008) S100A7-Downregulation Inhibits Epidermal Growth Factor-Induced Signaling in Breast Cancer Cells and Blocks Osteoclast Formation. PLos One, 3:e1741.
Sneh A. et al., (2013) Differential role os paoriasin (S100A7) in estrogen receptor α positive and negative breast cancer cells occur through actin remodeling. Breast Cancer Res Treat, 138(3)727-739.
Szlosarek et al., (2006) Tumour necrosis factor-α as a tumour promoter. Eur. J. Cancer, 42(6):745-50.
Tripathi, et al., (2010) Nuclear S100A7 is associated with poor prognosis in head and neck cancer. PLos 5(8):e11939.
Watson PH. et al., (1998) Molecules in focus Psoriasin (S100A7). Int J. Biochem Cell Biol, 30(1): 567-571.
West NR. et al., (2010) S100A7 (psoriasin) is induced by the proinflammatory cytokines oncostatin-M and interleukin-6 in human breast cancer. Oncogene, 29(14):2083-2092.
Zhang et al., (2008) Selective expression of S100A7 in lung squamous cell carcinomas and large cell carcinomas but not in adenocarcinomas and small cell carcinomas. Thorax, 63(4): 352-359.
International Search Report issued by the International Searching Authority (ISA/O.E.P.M.) on Jul. 22, 2014 in connection with International Application No. PCT/EP2014/057213.
Amita, S. et al., "Differential role of psoriasin (S100A7) in estrogen receptor [alpha] positive and negative breast cancer cells occur through actin remodeling", Breast Cancer Research and Treatment, vol. 138, No. 3, 2013, pp. 727-739.
Celis et al., "Bladder Squamous Cell Carcinomas Express Psoriasin and Externalize it to the Urine", Journal of Urology, Lippincott Williams & Wilkins, Baltimore, MD, US, vol. 155, No. 6, 1996, pp. 2105-2112.
Cyranka-Czaja, A. et al., "Selection and characterization of human antibody fragments specific for psoriasin A cancer associated protein", Biochemical and Biophysical Research Communications, vol. 149, No. 2, 2012, pp. 250-255.
Mandal et al., "S100A7 (psoriasin) influences immune reponse genes in human breast cancer", Experimental Cell Research, Academic Press, US, vol. 313, No. 14, 2007, pp. 3016-3025.
Nasser, M.W., et al., "S100A7 enhances mammary tumorigenesis through upregulation of inflammatory pathways", Cancer Research, 2012, pp. 604-615.
Watson, P.H. et al., "Molecules in focus: Psoriasin (S100A7)", International Journal of Biochemistry and Cell Biology, Pergamon, GB, vol. 30, 1998, pp. 567-571.
West, N.R. et al., "S100A7 (psoriasin) is induced by the proinflammatory cytokines oncostation-M and interleukin-6 in human breast cancer", Oncogene, vol. 29, No. 14, 2010, pp. 2083-2092.

\* cited by examiner

| Secreted TNFα | | | | | | 17 kDa |
|---|---|---|---|---|---|---|
| S100A7 (μM): | — | 3 | 3 | 3 | — | — |
| mAb 2H3 (μM): | — | — | 3 | — | 3 | — |
| mAb 2D9 (μM): | — | — | — | 3 | — | 3 |

ANTI-S100A7 ANTIBODIES FOR THE TREATMENT AND DIAGNOSIS OF CANCER

RELATED APPLICATIONS

This application is a § 371 national stage of PCT International Application No. PCT/EP2014/057213, filed Apr. 9, 2014, designating the United States, and claiming priority of European Patent Application EP13382128.0, filed Apr. 9, 2013, the contents of each of which are hereby incorporated by reference into this application.

REFERENCE TO SEQUENCE LISTING

This application incorporates-by-reference nucleotide and/or amino acid sequences which are present in the file named "151209_0206_88251_Substitute_Sequence_Listing_SC.txt," which is 2 kilobytes in size, and which was created Dec. 9, 2015 in the IBM-PC machine format, having an operating system compatibility with MS-Windows, which is contained in the text file filed Dec. 9, 2015 as part of this application.

FIELD OF THE INVENTION

The invention relates to the use of antibodies against the S100A7 protein for the prevention and/or treatment of cancer or a disease associated to an undesired angiogenesis or a disease associated with inflammation; and to methods and kits for diagnosing and determining the prognostic of said diseases in vitro or in vivo by means of detecting levels of S100A7 in a biofluid, preferably with an antibody. The invention also relates to specific anti-S100A7 monoclonal antibodies, hybridoma cell lines producing them and method for obtaining them, as well as pharmaceutical compositions and conjugates containing them.

BACKGROUND OF THE INVENTION

Cancers are the most frequent type of human malignancies, and the fatality of cancer predominantly results from the dissemination of primary tumor cells to distant sites and the subsequent formation of metastases.

S100A7 protein (Psoriasin) is a member of the S100 family of calcium-binding proteins which was initially identified as an over-expressed protein in the skin of patients with psoriasis. In normal cells the expression levels of S100A7 protein are very reduced, however high levels of expression of said protein can be found in tumor cells derived from for example, breast cancer, skin cancer, stomach cancer, bladder cancer and also head and neck cancer.

In breast cancer, the expression levels of S100A7 protein are very high in stage of pre-invasive tumors such ductal carcinoma in situ and are reduced in the acquisition of invasive phenotype. The persistently high expression level of S100A7 in invasive breast cancer is a poor prognosis factor in cancer patients. This correlation has also been demonstrated in skin cancer patients among other cancers.

The intracellular and extracellular location of S100A7 has been demonstrated and its expression can be detected in the cytoplasm and sometimes, in the cellular nucleus. The entire mechanism of action of said protein is still unknown although the Jab1 protein has been identified as S100A7 binding-protein.

The S100A7 protein has a proinflammatory function acting as chemotactic agent for immune cells recruiting. In this sense, the positive correlation between high expression of S100A7 and immune cells infiltration in tumoral stroma and also with metastatic potential has been described.

S100A7 plays an important role in breast cancer progression by promoting angiogenic response. When S100A7 is secreted by mammary epithelial cells, said protein induces an increase in endothelial cell proliferation acting via RAGE receptor (receptor for advanced glycation end products).

The S100A7 protein is also over-expressed in a large number of hyperproliferative and inflammatory skin diseases including atopic dermatitis.

It has been demonstrated that pro-inflammatory action of S100A7 is carried out by its interaction with RAGE receptor. Said interaction is involved in immune cells recruiting and also induces cytokine and chemokine production by neutrophils which contribute to inflammatory process.

It has been disclosed that silencing S100A7 by using stable short hairpin RNA (shRNA) in a human tumor cell line increases anchorage-independent growth, cell motility and invasion in vitro, while decreasing tumorigenicity in vivo (Krop et al., Cancer Res., 2005; 65:11326-11334). However, these effects are not due to the direct inhibition of S100A7 activity, but rather to decreased VEGF and increased MMP-13 levels.

Therefore, there is a need in the art to provide new therapeutic approaches for the treatment of cancer, particularly for the treatment of metastatic cancer, targeting the S100A7 protein.

In addition, at a diagnostic level, S100A7 can be considered a good marker in the differentiation progress of a normal cell towards a tumor cell, and therefore is a good biomarker in the cytological examination of tumors (Barbieri M R. et al., BMC Res Notes, 2011; 4(1): 494). However, the detection of the expression of S100A7 in cancerous tissue presents the drawback of requiring a patient biopsy. Therefore, there is a need in the art to provide a simpler and less invasive method for the clinical diagnosis of cancer by means of detecting the levels of S100A7 in a subject.

SUMMARY OF THE INVENTION

In a first aspect, the invention relates to the use of an antibody which binds specifically to the S100A7 protein or of a fragment thereof with capacity for binding to the antigen for use in the prevention and/or treatment of a disease selected from cancer, a disease associated to an undesired angiogenesis and a disease associated with inflammation.

In another aspect, the invention relates to a specific anti-S100A7 monoclonal antibody produced by a hybridoma selected from the group consisting of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7.

In another aspect, the invention relates to a hybridoma cell line selected from those cell lines deposited with accession number ECACC 13020701, ECACC 13020702, ECACC 13020703, ECACC 13020704, ECACC 13020705 and ECACC 13020706.

In additional aspects, the invention relates to a conjugate comprising a monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7, and a second component selected from the group of:
(a) a cytotoxic agent
(b) an antiangiogenic agent
(c) an antimetastatic agent
(d) an antiproliferative agent and
(e) an antiinflammatory agent as well as to the uses thereof in the prevention and/or treatment of cancer, or a disease associated to an undesired angiogenesis, or a disease associated with inflammation.

In yet another aspect, the invention relates to a method for obtaining a monoclonal antibody of the invention which comprises culturing a hybridoma cell line selected from those cell lines deposited with accession number ECACC 13020701, ECACC 13020702, ECACC 13020703, ECACC 13020704, ECACC 13020705 and ECACC 13020706 in conditions which allow the production of said antibody.

In another aspect, the invention relates to a pharmaceutical composition comprising a pharmaceutically effective amount of at least one monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 and at least one pharmaceutically acceptable excipient.

In another aspect, the invention relates to an in vitro method for diagnosing cancer selected from digestive and genital carcinoma or a disease associated to an undesired angiogenesis, or a disease associated with inflammation in a subject which comprises:
(a) detecting the levels of the S100A7 protein or of a variant thereof in a biofluid of said subject, and
(b) comparing said levels with a reference value wherein increased levels of the S100A7 protein or of a variant thereof with respect to the reference value are indicative of the subject suffering from cancer selected from digestive and genital carcinoma or a disease associated to an undesired angiogenesis or a disease associated with inflammation.

In another aspect, the invention relates to an in vitro method for determining the prognosis or for monitoring the progression of a cancer selected from digestive and genital carcinomaor a disease associated to an undesired angiogenesis, or a disease associated with inflammation in a subject which comprises:
(a) detecting the levels of the S100A7 protein or of a variant thereof in a biofluid of said subject, and
(b) comparing said levels with a reference value for said protein obtained from the same subject at an earlier time point of the disease wherein a decrease in the levels of the S100A7 protein or a variant thereof with respect to the reference value is indicative that the digestive or genital carcinoma or a disease associated to an undesired angiogenesis or a disease associated with inflammation shows a good prognosis or wherein an increase in the levels of the S100A7 protein or a variant thereof with respect to the reference value is indicative that the digestive or genital carcinoma or a disease associated to an undesired angiogenesis or a disease associated with inflammation shows a bad prognosis.

In another aspect, the invention relates to a kit for diagnosing or for determining the prognosis or monitoring the progression of cancer or a disease associated to an undesired angiogenesis or a disease associated with inflammation in a biofluid which comprises at least one antibody produced by a hybridoma selected from the group consisting of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7.

DETAILED DESCRIPTION OF THE INVENTION

Figure 1:
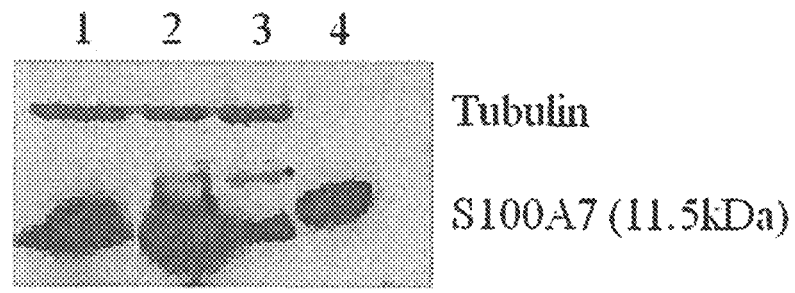
FIG. 1. S100A7 protein expression determined by Western-blot analysis in cell extracts of different origins. Lane 1, HT29 (colorectal carcinoma); Lane 2, MDA-MB-468 (breast carcinoma); Lane 3, MCF-7 (breast carcinoma); Lane 4, human recombinant S100A7.

The authors of the present invention have surprisingly discovered that monoclonal antibodies directed against the S100A7 protein are capable of neutralizing the proliferative and migrative capacity induced by S100A7 in functional in vitro tumor proliferation and tumor migration assays. These results indicate that the anti-S100A7 antibodies are useful for the prevention and/or treatment of cancer. The authors of the present invention have also found that monoclonal antibodies directed against the S100A7 protein have antimetastatic activity.

Moreover, these findings allow for the development of assays for the early detection of cancer based on the detection of the levels of S100A7 in a biofluid.

The authors of the present invention have additionally demonstrated that the monoclonal antibodies against the S100A7 protein are capable of neutralizing levels of the TNF alpha molecule which is produced by tumor cell lines induced by S100A7. TNF alpha is one of the most important molecules produced during the inflammatory process and is overexpressed in most of chronic inflammatory disorders. These results indicate that the S100A7 antibodies are also useful for the prevention and/or treatment of inflammatory diseases.

Therefore, the present invention also relates to a method (in vitro or in vivo) and to kits for the diagnosis of cancer or diseases associated to an undesired angiogenesis or diseases associated with inflammation in a patient by means of detecting the levels of S100A7 in a biofluid, especially with antibodies.

Therapeutic Uses of the Anti-S100A7 Antibodies
Cancer and Angiogenesis

The anti-S100A7 antibodies capable of binding specifically to the S100A7 protein can be used for the treatment of tumors wherein S100A7 is expressed.

Specifically, the S100A7 protein is expressed, as has been described above, in a wide variety of cancers. As a result, the S100A7 protein ligands, and more specifically, antibodies specific against this protein, are candidate drugs to be used in therapy for the treatment of cancer or for the treatment of diseases associated to an undesired angiogenesis.

Thus, in one aspect, the invention relates to an antibody which binds specifically to the S100A7 protein or of a fragment thereof with capacity for binding to the antigen for use in the prevention and/or treatment of a disease selected from cancer and a disease associated to an undesired angiogenesis.

In another aspect, the invention relates to the use of an antibody which binds specifically to the S100A7 protein or a fragment thereof with capacity for binding to the antigen for the preparation of a medicament for the prevention and/or treatment of a disease selected from cancer and a disease associated to an undesired angiogenesis In another aspect, the invention relates to a method of treatment or prevention of a disease selected from cancer and a disease associated to an undesired angiogenesis in a subject which comprises the administration to said subject of an antibody which binds specifically to the S100A7 protein or of a fragment thereof with capacity for binding to the antigen.

As it is used in the present invention, the term "antibody" relates to a monomeric or multimeric protein which comprises at least one polypeptide having the capacity for binding to a determined antigen and comprising all or part of the light or heavy chain variable region of an immunoglobulin molecule. The term antibody includes any type of known antibody, such as, for example, polyclonal antibodies, monoclonal antibodies and genetically engineered antibodies, such as chimeric antibodies, humanized antibodies, primatized antibodies, human antibodies and bispecific antibodies.

The basic structural unit of a typical antibody is a tetramer, which is made up of two identical pairs of polypeptide chains, each pair having a "light" or L chain (approximately 25 kDa) and a "heavy" or H chain (approximately 50-70 kDa). The amino-terminus part of each chain includes a variable region of approximately 100 to 110 or more amino acids which are mainly responsible for antigen recognition; whereas the carboxyl-terminus part of each chain defines a constant region, mainly responsible for the effector function. The light chains consist of a variable region (VL) and a constant region (CL); whereas the heavy chains have a variable region (VH) and three constant regions (CH1, CH2, CH3). Within the light and heavy chains, the variable and constant regions are bound together by means of a "J" region of approximately 12 or more amino acids, the heavy chain also including a "D" region of approximately 10 more amino acids. In general, see Fundamental Immunology Cap. 7 (Paul, W., ed., 2$^{nd}$ ed. Raven Press, N.Y. (1989)). The variable regions of each pair of light/heavy chains form the antibody binding site, such that an intact antibody typically has two equal binding sites.

All the chains have the same general structure of relatively conserved framework regions (FR) bound by means of three hypervariable regions, also referred to as complementarity determining regions or CDRs. The CDRs of the two chains of each pair are aligned by means of the framework regions, and the CDR regions are responsible for binding to a specific epitope. From the N-terminus end to the C-terminus end, both the light and heavy chains comprise the FR1, CDR1, FR2, CDR2, FR3, CDR3 and FR4 domains. The assignment of amino acids to each domain is according to the definitions of the Kabat sequences of proteins of immunological interest (National Institutes of Health, Bethesda, Md. (1987 and 1991); Chothia and Lesk J. Mol. Biol. 196:901-917 (1987); Chothia et al Nature 342:878-883 (1989)).

In the present invention, "polyclonal antibodies" are understood as antibodies derived from different B-cell lines, i.e., antibodies which are a mixture of immunoglobulins, secreted against a specific antigen (S100A7), each of which recognizes different epitopes.

"Monoclonal antibodies" are understood as identical homogenous antibodies produced by a hybrid cell product of the fusion of a B-cell clone descendent of a single unique parent cell and a tumor plasma cell. In a particular embodiment, the antibody is a monoclonal antibody.

"Chimeric antibodies" are understood as antibodies constructed with variable regions of an antibody of a species (usually a mammal in which the monoclonal antibody was generated) and constant regions of another species (that species in which the chimeric antibody is going to be used). The objective of said construct is to obtain an antibody with the original monoclonal antibody but which is less immunogenic and better tolerated in the subject who is going to be treated, with an improved serum half-life and which can be recognized by immunological effector mechanisms, i.e., the complement, the Fc receptor of cytotoxic cells or other specific immunoglobulin receptors which show species specificity. In a preferred embodiment, the chimeric antibodies are formed by murine variable regions and human constant regions.

"Humanized antibody" is understood as an antibody from a nonhuman antibody, typically a murine antibody, which conserves the antigen binding properties of the parent antibody, but which is less immunogenic in human beings. This can be achieved by means of different processes, which include (a) grafting the complete nonhuman variable domains into human constant regions to generate chimeric antibodies; (b) grating only the nonhuman complementarity determining regions (CDR) in a human framework and the constant regions, with or without retaining the critical framework residues; and (c) transplanting the complete nonhuman variable domains, but "concealing them" with a section similar to the human variable domain by means of replacing the surface residues.

"Primatized antibody" is understood as a recombinant antibody that has been genetically manipulated to contain the heavy and light variable domains of a monkey antibody (or of another primate), particularly an antibody of a cynomolgus monkey, and containing sequences of a human constant domain, preferably the constant domain of human gamma 1 or 4 immunoglobulin (or a PE variant). The preparation of said antibodies is described in Newman et al., Biotechnology, 10: 1458-1460 (1992); and in patent documents U.S. Pat. No. 5,658,570 and U.S. Pat. No. 6,113,898. It has been described that these antibodies show a high degree of homology with human antibodies, i.e., 85-98%, they have human effector functions, they have lower immunogenicity and can show a high affinity for human antigens. Another very effective means for generating recombinant antibodies is described by Newman, Biotechnology, 10: 1455-1460 (1992).

"Human antibody" is understood as an antibody integrally containing human light and heavy chains as well as constant regions, produced by means of any of the known standard methods.

"Bispecific antibodies" or "bifunctional antibodies" are understood as antibodies having binding specificities for at least two different epitopes. The exemplary bispecific antibodies can bind to two different epitopes of the B-cell surface marker. Others of the said antibodies can bind to a first B-cell marker and additionally bind to a second B-cell surface marker. Alternatively, a binding arm of an anti-B cell marker can be combined with an arm which binds to a triggering molecule in a leukocyte, such as a T-cell receptor molecule (for example, CD2 or CD3), or Fc receptors for IgG (FcγR), such as FcγRI (CD64), FcγRII (CD32) and FcγRIII (CD 16), such that the mechanisms of cell defense are concentrated in the B-cell. Bispecific antibodies can also be used to locate cytotoxic agents against the B-cell. These antibodies have a binding arm to the marker of the lymphocyte and an arm which binds to the cytotoxic agent (for example, saporin, anti-interferon-α, vinca alkaloid, ricin A-chain, methotrexate or a radioactive hapten isotope). Bispecific antibodies can be prepared as whole antibodies or as antibody fragments (for example, F(ab)$_2$ bispecific antibodies).

The invention also comprises the use of fragments of the different types of antibodies mentioned above. The term "antibody fragment" includes antibody fragments such as Fab, F(ab')$_2$, Fab', single chain Fv fragments (scFv), diabodies and nanobodies.

Papain digestion of antibodies produces two identical antigen binding fragments referred to as "Fab" fragments, each with a single antigen binding site, and a residual "Fc" fragment, the name of which reflects its capacity for readily crystallizing. Pepsin treatment yields an F(ab')$_2$ fragment which has two antigen binding sites and which is still capable of cross-linking to the antigen.

"Fv" is the minimal antibody fragment containing a complete antigen binding and antigen recognition site. This region consists of a variable domain of a variable light chain and heavy chain dimer in a strong noncovalent association. In this configuration the three hypervariable regions of each variable domain interact to define an antigen binding site on the surface of the VH-VL dimer. As a whole, the six hypervariable regions confer antigen-antibody specificity to the antibody. However, even a single variable domain (or half an Fv, which comprises only three hypervariable regions specific for an antigen) has antigen recognition and binding capacity, although with less affinity than the complete binding site.

The Fab fragment also contains the constant domain of the light chain and the first constant domain (CH1) of the heavy chain. Fab' fragments differ from Fab fragments in the addition of a few residues at the carboxy terminus of the domain CH1 of the heavy chain, including one or more cysteine of the antibody hinge region.

The "single chain Fv" or "scFv" antibody fragments comprise the VH and VL domains of an antibody, in which these domains are present in a single polypeptide chain. Preferably, the Fv polypeptide additionally comprises a linker polypeptide between the VH and VL domains which allows the scFv to form the desired structure for antigen binding. For a review of scFv, see Pluckthun in The Pharmacology of Monoclonal Antibodies, vol. 113, Rosenburg and Moore eds., Springer-Verlag, N.Y., pp. 269-315 (1994).

The term "diabodies" refers to small antibody fragments with two antigen binding sites, those fragments comprising a heavy chain variable domain (VH) connected to a light chain variable domain (VL) in the same polypeptide chain (VH-VL). By means of using a linker which is too short to allow pairing between the two domains in the same chain, the domains are forced to pair with the complementary domains of another chain and create two antigen binding sites. Diabodies are described in further detail in, for example, documents EP 404,097; WO 93/11161; and Hollinger et al., Proc. Natl. Acad. Sci. USA, 90: 6444-6448 (1993).

The term "nanobodies" designates small sized entities (15 kDa) formed solely by the antigen binding region of the heavy chain (VH fragment) of immunoglobulins. Said nanobodies are mainly produced after immunizing animals of the Camelidae family, such as camels, llamas and dromedaries, mainly llamas; and also of the shark family, which have the particularity of having antibodies which naturally lack the light chain and recognize the antigen by the heavy chain variable domain. Nevertheless, the nanobodies derived from these sources require a humanization process for their therapeutic application. Another potential source for obtaining nanobodies is from antibodies derived from different human samples by separating the VH and VL domains of the variable region. Nanobodies present advantages such as a production cost reduction with respect to whole antibodies, stability and the reduction of immunogenicity.

The antibody fragments included in the present invention conserve the capacity for binding to the S100A7 antigen of the whole antibody they derive, and they also conserve the function of inhibiting one or more characteristic functions of the S100A7 protein, such as binding activity, signaling activity and/or the stimulation of a cell response. For example, in one embodiment, an antibody fragment can inhibit the interaction of the S100A7 protein with one or more of its ligands, especially with its RAGE ligand, and/or it can inhibit one or more functions mediated by said protein, such as the tumor cell proliferation, metastasis or the formation of tumor spheres. In another embodiment, an antibody fragment can inhibit the interaction of the S100A7 protein with one or more of its ligands, especially with its RAGE ligand, and/or it can inhibit one or more functions mediated by said protein such as endothelial cell proliferation.

The antibody is capable of inhibiting the interaction of the S100A7 protein with the receptor for advanced glycation endproducts (RAGE). The term "receptor for advanced glycation end products (RAGE)" used herein refers to a transmembrane ligand-regulated receptor of the immunoglobulin superfamily capable of binding advanced glycation endproducts, which modulates pro-inflammatory intracellular signaling cascade incurred when the target protein is interacting. The expression "advanced glycation end product" refers to the end product of a chain of chemical reactions after an initial glycation reaction. Said term encompasses the S100A7 of any mammalian species, including but not being limited to domestic and farm animals (cows, horses, pigs, sheep, goats, dogs, cats or rodents), primates and humans. Preferably, the RAGE is human.

In the present invention, "human RAGE" is understood as the protein defined by the sequence of the Swiss-Prot database with accession number Q15109 (release of Jul. 11, 2012).

As used herein is understood that "antibody capable of inhibiting the interaction of the S100A7 protein with the receptor for advanced glycation end products (RAGE)" refers to an antibody capable of inhibiting the binding of S100A7 protein to RAGE receptor while not inhibiting the interaction between RAGE and other ligands such as other members of the S100 family, high-mobility group box 1 ligand (HMGB1) or advanced glycation end products.

To identify the antibodies capable of inhibiting the interaction of the 5100A7 protein with RAGE, assays well known in the art can be used. Said assays typically involve measuring the formation of a complex between S100A7 protein and RAGE in the presence of an antibody. Said antibodies conserve the function of inhibiting one or more characteristic functions of the S100A7 protein, such as binding activity, signaling activity and/or the stimulation of a cell response. Said inhibition of the interaction can be evaluated by means of the assays described in examples of the present invention. For example, in one embodiment, one or more antibodies of the invention can inhibit one or more functions mediated by the S100A7 protein as the formation of tumor spheres shown in Example 10 or the tumor cell proliferation shown in Example 11.

The antibodies useful in the invention bind specifically to the S100A7 protein. As it is used herein, the expression "binds specifically to" refers to the capacity of the antibodies for binding specifically to the S100A7 protein and not to other proteins of the S100 family.

Suitable assays for the identification of antibodies with the desired specificity include, immunochemical assays, such as immunofluorescence, flow cytometry, Western blot and ELISA assays, radioimmunoassays, immunohistochemical assays, immunoprecipitations or other immunochemical assays known in the art. A number of protocols for competitive binding or immunoradiometric assays are known in the state of the art. Said immunoassays typically involve measuring the formation of a complex between an antibody and an immunogen of the S100A7 protein.

As it is used herein, the term "S100A7" refers to a protein belonging to the family of calcium binding proteins called S100, which is overexpressed in tumor cells and associated with tumor proliferation, the invasive and metastatic capacity of tumor cells and with capacity of formation of tumor spheres. As used herein, the term "S100A7" also refers to a protein belonging to the family of calcium binding proteins called, S100 which is associated with angiogenesis. The term also includes all the physiologically relevant post-translational chemical modifications forms, for example, glycosylation, phosphorylation or acetylation, etc., provided that the functionality of the protein is maintained. Said term encompasses the S100A7 of any mammal species, including but not being limited to domestic and farm animals (cows, horses, pigs, sheep, goats, dogs, cats or rodents), primates and humans. Preferably, the S100A7 is human.

In the present invention, "human S100A7" is understood as the protein defined by the sequence of the Swiss-Prot database with accession number P31151 (release of Jul. 11, 2012).

The first aspect of the invention contemplates the use of functionally equivalent variants of S100A7. As it is used herein, "functionally equivalent variant of S100A7" is understood as any molecule sharing with S100A7 one or more of the functions described in the present invention associated with S100A7, both in vitro and in vivo, and having a minimal identity in the amino acid sequence. The variants of S100A7 can be both natural and artificial.

The expression "natural variant" refers to all those variants of human S100A7 mentioned above which occur naturally in other species, i.e., S100A7 orthologs. Said natural variants include but are not limited to S100A7 of cows, corresponding to the sequences with accession number DAA31756 and NP 777021 (release of May 21, 2010 and Apr. 28, 2012, respectively) or to the predicted sequence with accession number XP_002686048 (release of Dec. 1, 2011); S100A7 of mice, corresponding to the sequence with accession number AAS91715 (release of Apr. 21, 2004); S100A7 of horses, corresponding to the sequence with accession number NP_001075349 (release of Apr. 22, 2012); macaque monkeys, corresponding to the predicted sequence with accession number XP_001110603 (release of Jun. 1, 2010); S100A7 of pigs, corresponding to the predicted sequence with accession number XP_003125797 (release of Oct. 11, 2011). The natural variants of S100A7 suitable for use in the first aspect of the present invention can also be derived from said sequences by means of insertion, substitution or deletion of one or more amino acids and include natural alleles, variants resulting from alternative processing and secreted and truncated forms occurring naturally.

The S100A7 useful in the present invention can, therefore, be of a natural sequence when it comprises a polypeptide having the same amino acid sequence as the S100A7 derived from nature. Such polypeptides of a natural sequence can be isolated from nature or they can be produced by recombinant and/or synthetic means. Thus, the S100A7 of the invention can be a recombinant protein obtained by the expression of a polynucleotide encoding S100A7 or a functionally equivalent variant thereof in a heterologous organism, such as a bacterium, yeast or insect or mammal cell. Said recombinant protein can be obtained as a fusion protein with an amino-terminus tail of histidines facilitating the subsequent purification thereof. The expression and purification of said proteins can be performed according to methods known by the person skilled in the art and described in the state of the art.

In a preferred embodiment, the S100A7 is of a human origin, preferably of sequence with accession number P31151 in Swiss-Prot database (release of Jul. 11, 2012). In another preferred embodiment, the S100A7 is a fusion protein comprising the sequence of human S100A7 with an amino-terminus tail of three additional amino acids, the sequence of which is SEQ ID NO: 1.

```
                                          SEQ ID NO: 1
GSHMSNTQAERSIIGMIDMFHKYTRRDDKIEKPSLLTMMKENFPNF

LSACDKKGTNYLADVFEKKDKNEDKKIDFSEFLSLLGDIATDYHKQ

SHGAAPCSGGSQ
```

Alternatively, the S100A7 can be an artificial functionally equivalent variant of S100A7 which can be obtained by recombinant and/or synthetic means.

The variants of S100A7 contemplated in the first aspect of the present invention show at least one of the functions of S100A7 such as, without limitation:

- the capacity for inducing tumor cell proliferation, which can be determined by means of the method described in Example 11 of the present invention.
- the capacity for stimulating the invasive and metastatic capacity of tumor cells, which can be determined by means of methods described in the state of the art, such as an stimulus-directed invasion using invasion chambers coated with matrigel or by performing orthotopic tumor growth models in mice (Arumugam T et al. 2006. J. Nat. Cancer Inst. 98:1806-1818).
- the capacity for forming tumor spheres, which can be determined by means of the method described in Example 10 of the present invention.
- the capacity for inducing the endothelial cell migration, which can be determined by means of the method described in Example 13 of the present application.
- the capacity for inducing an inflammatory response mediated by secretion of TNFalpha, which can be determined by means of the method described in Example 9 of the present application.
- the capacity for activating MMP9 matrix metalloproteinase activity, which can be determined by means of the method described in Example 13 of the present application.
- the capacity for inducing an inflammatory response in monocytes which can be determined by means of the method described in Example 14.
- the capacity for inducing tumor development in athymic nude mice, which can be determined by means of the method described in Example 15, Additionally, the functionally equivalent variants of S100A7 contemplated in the first aspect of the invention, include polypeptides showing at least 60%, 65%, 70%, 72%, 74%, 76%, 78%, 80%, 90%, 95%, 97%, 99% similarity or identity with the different natural variants of S100A7 mentioned above. The degree of identity between two polypeptides is determined using algorithms implemented in a computer and methods which are widely known by the persons skilled in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

In the context of the present invention, the term "antigen" refers to S100A7.

In general, modifications in the amino acid sequence of the antibody of the invention are also contemplated. For example, it can be desirable to improve the binding affinity and/or other biological properties of the antibody. The variants of the amino acid sequences of the antibody are prepared by introducing the suitable nucleotide changes in the nucleic acid encoding the antibody, or by means of peptide synthesis. Said modifications include, for example, eliminations and/or insertions and/or substitutions of residues in the amino acid sequences of the antibody. Any combination of elimination, insertion and substitution is performed to achieve the final construct, provided that the final construct has the desired characteristics, i.e., S100A7 binding specificity and antagonist activity of said protein. The changes in the amino acids can also alter the post-translational processes of the antibody, such as changing the number or the position of the sites of glycosylation.

Some insertions in the amino acid sequence include amino terminus and/or carboxy terminus fusions varying in length from one residue up to polypeptides containing one hundred or more residues, as well as insertions within the sequence of one or several amino acid residues. Some examples of terminal insertions include an antibody with an N-terminus methionyl residue, or the antibody fused to a cytotoxic polypeptide. Other variants by insertion of the antibody molecule include fusion with the N- or C-terminus of the antibody of an enzyme, or a polypeptide increasing the serum half-life of the antibody.

Another type of variant is a variant by amino acid substitution. These variants have at least one amino acid residue of the antibody substituted with a different residue. The sites of major interest for mutagenesis by antibody substitution include the hypervariable regions, but alterations in the FR are also contemplated.

"Medicament" is understood as a pharmaceutical composition comprising an antibody which binds specifically to the S100A7 protein or a fragment thereof with capacity for binding to the antigen.

"Prevention" is understood as the administration of an antibody which binds specifically to the S100A7 protein or of a fragment thereof with capacity for binding to the antigen, or of a medicament containing them in an initial or early stage of the disease, or to also prevent its onset.

The term "treatment" is used to designate the administration of an antibody which binds specifically to the S100A7 protein or of a fragment thereof with capacity for binding to the antigen or of a medicament containing it to control the progression of the disease before or after the clinical signs have appeared. Control of the progression of the disease is understood as the beneficial or desired clinical results which include but are not limited to reduction of the symptoms, reduction of the duration of the disease, stabilization of pathological conditions (specifically avoiding additional impairment), delaying the progression of the disease, improving the pathological condition and remission (both partial and complete). The control of the progression of the disease also involves a prolongation of survival in comparison to the expected survival if the treatment was not applied.

The terms "cancer" and "tumor" relate to an abnormal mass of cells within a multicellular organism that results from excessive cell division that is uncontrolled and progressive, also called a neoplasm. The antibodies binding specifically to the S100A7 protein or its fragments with capacity for binding to the antigen are useful for the treatment of any cancer or tumor, such as, without limitation, breast, heart, lung, small intestine, colon, splenic, kidney, bladder, head, neck, ovarian, prostate, brain, pancreatic, skin, bone, bone marrow, blood, thymic, uterine, testicular and liver tumors. Particularly, tumors which can be treated with said antibodies include but are not limited to adenoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and teratoma. Particularly, the tumor/cancer is selected from the group of aeral lentiginous melanoma, actinic keratosis adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, cystadenoma, endodermal sinus tumor, endometrial hyperplasia, endometrial stromal sarcoma, endometrioid adenocarcinoma, ependymal sarcoma, Ewing's sarcoma, focal nodular hyperplasia, germline tumors, glioblastoma, glucagonoma, hemagioblastoma, hemangioendothelioma, hemangioma, hepatic adenoma, hepatic adenomatosis, hepatocellular carcinoma, insulinoma, intraepithelial neoplasia, interepithelial squamous cell neoplasia, invasive squamous cell carcinoma, large-cell carcinoma, leiomyosarcoma, melanoma, malignant melanoma, malignant mesothelial tumor, medulloblastoma, medulloepithelioma, mucoepidermoid carcinoma, neuroblastoma, neuroepithelial adenocarcinoma, nodular melanoma, osteosarcoma, papillary serous adenocarcinoma, pituitary tumors, plasmacytoma, pseudosarcoma, pulmonary blastoma, renal cell carcinoma, retinoblastoma, rhabdomyosarcoma, sarcoma, serous carcinoma, small-cell carcinoma, soft tissue carcinoma, somatostatin secreting tumor, squamous carcinoma, squamous cell carcinoma, undifferentiated carcinoma, uveal melanoma, verrucous carcinoma, vipoma, Wilm's tumor. In an embodiment of the invention, the tumor/cancer to be prevented or treated with said antibodies is a cancer selected from fibrosarcoma, breast, colorectal carcinoma and epidermoid carcinoma, preferably selected from fibrosarcoma, colorectal carcinoma and epidermoid carcinoma. In another preferred embodiment of the invention, the tumor/cancer to be prevented or treated with said antibodies is colorectal cancer, preferably colorectal carcinoma. In another preferred embodiment of the invention, the tumor/cancer to be prevented or treated with said antibodies is a genital carcinoma. In another preferred embodiment of the invention, the tumor/cancer to be prevented or treated with said antibodies is a digestive carcinoma.

The term cancer includes both, primary tumors and metastasis.

The term primary tumor refers to a tumor which is in the primary site in which said tumor originates.

The term "metastasis", as used herein, refers to the process by which a cancer spreads or transfers from the site of origin to other regions of the body with the development of a similar cancerous lesion at a new location. A "metastatic" or "metastasizing" cell is one that loses adhesive contacts with neighboring cells and migrates via the bloodstream or lymph from the primary site of disease to invade neighboring body structures. This new tumor is known as a metastatic (or secondary tumor). When tumor cells metastasize, the new tumor cell is called a secondary or metastatic tumor, and its cells are similar to those in the original tumor. This means, for example, that if breast cancer metastasizes to the lungs, the secondary tumor is made up of abnormal breast cells, not of abnormal lung cells. The tumor in the lung is then called, metastatic breast cancer, not lung cancer. Metastatic tumors are very common in the late stages of cancer. The spread of metastasis may occur via the blood or the lymphatics or through both routes. The most common places for the metastases to occur are lung, liver, brain and the bones. In a preferred embodiment the cancer is a metastatic cancer.

In a preferred embodiment, the antibodies for use according to the present invention are characterized in that they block the activation of the MAPK pathway induced by S100A7.

The term "increased activation of the MAPK pathway", as used herein, refers to tumors wherein the activity and/or the expression of one or more components of the MAPK pathway are increased in respect to a reference level, wherein said reference level is the expression or activity in tumors which do not show an activation of the MAPK pathway or in non-tumor cells which have not been stimulated with agents capable of activating the MAPK pathway.

The term "MAPK pathway", also known as the Ras-Raf-MEK-ERK pathway, as used herein, refers to a chain of proteins in the cell that communicates a signal from a receptor on the surface of the cell to the DNA in the nucleus of the cell. The signal starts when a signaling molecule binds to the receptor on the cell surface and ends when the DNA in the nucleus expresses a protein and produces some change in the cell, such as cell division.

In a preferred embodiment, a tumor is considered as showing increased activation of the MAPK pathway if it shows increased expression and/or activity of one or more components of the MAPK pathway selected from the group consisting of EGFR, GRB2, SOS, Ras, RAF kinase, MEK1, MEK2 and MAPK. As used herein, increased expression or activity is understood as an expression level or activity level which is at least 10%, at least 20%, at least 30%, at least 40%, at least 50%, at least 100%, at least 200%, at least 300% or more with respect to a reference expression level or to a reference activity level. Methods for determining whether the expression level of a given component of the MAPK pathway is increased are well-known in the art and include methods based on the determination of the mRNA levels of the corresponding component (e.g., Northern blot, RT-PCR and the like) and methods based on the determination of the protein levels of the corresponding component (e.g., ELISA, Western blot, etc.). Methods for determining whether the activity of one or more components of the MAPK pathway is increased are based on the determination of the activity of the different components and are widely known to the skilled person. Suitable methods for determining the activity of the MAPK pathway include, for instance, the detection of phosphorylated ERK (MAPK) protein as well as the ratio of phosphoERK to ERK.

In a preferred embodiment, the antibodies for use according to the present invention are characterized in that they block the increased expression of TNFalpha induced by S100A7.

The term "increased expression of TNFalpha", as used herein, refers to tumors wherein the activity and/or the expression of TNFalpha are increased in respect to a reference level, wherein said reference level is the expression or activity in tumors which do not show increased TNFalpha activation or in non-tumor cells which have not been stimulated with agents capable of activating TNFalpha.

In a preferred embodiment, a tumor is considered as showing increased expression of TNFalpha if it shows a expression level or activity level of TNFalpha which is at least 10%, at least 20%, at least 30%, at least 40%, at least 50%, at least 100%, at least 200%, at least 300% or more with respect to a reference expression level or to a reference activity level. Methods for determining whether the expression level of TNFalpha is increased are well-known in the art and include methods based on the determination of the mRNA levels of the corresponding component (e.g., Northern blot, RT-PCR and the like) and methods based on the determination of the protein levels of the corresponding component (e.g., ELISA, Western blot, etc.). Methods for determining whether the TNFalpha activity is increased are based on the determination of the biological activity of TNFalpha. Since TNFalpha is a secreted protein, the determination of the activity of TNFalpha can be determined by measuring TNFalpha activity in the conditioned culture media of the tumor cells.

The term "colorectal carcinoma" is understood as cancer from uncontrolled cell grown in the colon or rectum or in the appendix. In another preferred embodiment of the invention, the tumor/cancer to be prevented or treated with said antibodies is fibrosarcoma.

As used herein, the term "fibrosarcoma" refers to a malignant tumor composed of cells and fibers derived from fibroblasts, which produce collagen but otherwise lack cellular differentiation.

In another preferred embodiment of the invention, the tumor/cancer to be treated is epidermoid carcinoma.

As used herein, the term "epidermoid carcinoma" refers to a malignant tumor derived from epithelial tissue that tends to metastasize other areas of the body.

In another preferred embodiment of the invention, the tumor/cancer to be treated is genital carcinoma.

As used herein, the term "genital carcinoma" refers to a malignant tumor derived from genital transformed tissue that tends to metastasize other areas of the body. The term "genital carcinoma" refers to any carcinoma having its origin in the genital organs including, without limitation, vaginal carcinoma, cervix carcinoma, ovarian carcinoma, oviductal carcinoma, uterine carcinoma, and carcinomas of the male genital tract.

In another preferred embodiment of the invention, the tumor/cancer to be treated is a digestive carcinoma. The term "digestive carcinoma", as used herein, refers to any malignant condition of the gastrointestinal tract and accessory organs of digestion. As used herein, "digestive carcinoma" means any gastrointestinal cancer (i.e. any carcinoma having its origin in the digestive organs) including, without limitation, esophagus, stomach, biliary system, pancreas, small intestine, large intestine, rectum, anus and colorectal cancer. In another preferred embodiment of the invention, the tumor/cancer to be prevented or treated with said antibodies is breast cancer.

The term "breast cancer" is understood as cancer from uncontrolled cell grown in the breast.

The authors of the present invention have discovered that the S100A7 protein is involved in the formation of tumor spheres. Therefore, in a particular embodiment the cancer to be prevented or treated is a cancer forming tumor spheres.

"Cancer forming tumor spheres" refers to a tumor composed of progenitor cells which are capable of forming spheres and which have a capacity of self-renewal and tumorigenesis and which can be induced to differentiate in vitro into tumor cells. The capacity of self-renewal herein implies the capacity of clonal proliferation.

In a particular embodiment the cancer to be prevented or treated is a metastatic cancer.

As used herein, the term "metastatic" refers to a cancer for which there is known to exist at least one tumor (a "secondary tumor") in an organ other than the organ which is the source of the tumor cells. For example, colorectal cancer has a tendency to spread from the colon or rectum to lymph nodes and then to the liver. The organ which is the source of the tumor cells can be identified using standard methods in the art.

In the context of the present invention, the term "angiogenesis" is understood to mean the physiological process that consists of the formation of new blood vessels from existing blood vessels. Angiogenesis is also known as neovascularization.

The expression "diseases associated to undesired angiogenesis" relates to all those diseases where pathogenic angiogenesis occur i.e. when said process is harmful or undesirable, whether cancerous or not. The scope of the present invention excludes the treatment of angiogenesis in situations where it is necessary, such a wound healing, diseases associated to an undesired angiogenesis which may be treated with the compounds in accordance with the present invention, without limitation, are inflammatory diseases, especially chronic inflammatory diseases such as rheumatoid arthritis, psoriasis, sarcoidosis and such like; autoimmune diseases; viral diseases; genetic diseases; allergic diseases; bacterial diseases; ophthalmological diseases such as diabetic retinopathy, premature retinopathy, proliferative atrial retinopathy, retinal vein occlusion, macular degeneration, senile discoid macular degeneration, neovascular ocular glaucoma, choroidal neovascularization diseases, retinal neovascularization diseases, rubeosis (angle neovascularization), corneal graft rejection, retrolental fibroplasia, epidermal keratoconjunctivitis, vitamin A deficiency, contact lens exhaustion, atopical keratitis, superior limbic keratitis, pterygium dry eye, Sjögrens syndrome, acne rosacea, phlyctenulosis, syphilis, micobacterial infections, lipid degeneration, burns with corrosive substances, bacterial ulcers, mycotic ulcers, protozoan infections, Kaposi sarcoma, Mooren's ulcer, Terrien marginal degeneration, marginal keratolysis, scleritis, chronic retinal detachment and such like; atherosclerosis; endometriosis; obesity; cardiac insufficiency; advanced renal insufficiency; endotoxemia; toxic shock syndrome; meningitis; silicon-induced fibrosis; asbestos-induced fibrosis; apoplexia; periodontitis; gingivitis; macrocytic anaemia; refractory anaemia; 5q deletion syndrome; conditions where the vascularization is altered as infection by HIV, hepatitis, hemorrhagic telangiectasia or Rendu-Osler-Weber's disease.

In a preferred embodiment, the disease associated to an undesired angiogenesis is a disease selected from cancer, rheumatoid arthritis, psoriasis, sarcoidosis, diabetic retinopathy, premature retinopathy, retinal vein occlusion, senile discoid macular degeneration, atherosclerosis, endometriosis and obesity, preferably cancer.

In a particular embodiment the diseases associated to an undesired angiogenesis are inflammatory diseases. "Inflammatory disease" is understood to be any disease where there is an excessive or altered inflammatory response that leads to inflammatory symptoms. Said inflammatory diseases which may be treated by compounds of the invention include, without limitation, Addison's disease, acne vulgaris, alopecia areata, amyloidosis, ankylosing spondylitis, ulcerations, aphthous stomatitis, arthritis, arteriosclerosis, osteoarthritis, rheumatoid arthritis, bronchial asthma, Bechet's disease, Boeck's disease, intestinal inflammatory disease, Crohn's disease, choroiditis, ulcerative colitis, celiac's disease, cryoglobulinemia, macular degeneration, dermatitis, dermatitis herpetiformis, dermatomyositis, insulin dependent diabetes, juvenile diabetes, inflammatory demyelinating disease, Dupuytren contracture, encephalomyelitis, allergic encephalomyelitis, endophthalmia, allergic enteritis, autoimmune enteropathy syndrome, erythema nodosum leprosum, ankylosing spondylitis, idiopathic facial paralysis, chronic fatigue syndrome, rheumatic fever, cystic fibrosis, gingivitis, glomerulonephritis, Goodpasture syndrome, Graves syndrome, Hashimoto's disease, chronic hepatitis, histiocytosis, regional ileitis, iritis, disseminated lupus erythematous, systemic lupus erythematous, cutaneous lupus erythematous, lymphogranuloma, infectious mononucleosis, miastenia gravis, transverse myelitis, primary idiopathic myxedema, nephrosis, obesity, sympathetic ophthalmia, granulomatous orchitis, pancreatitis, panniculitis, pemphigus vulgaris, periodontitis, polyarteritis nodosa, chronic polyarthritis, polymyositis, acute polyradiculitis, psoriasis, chronic obstructive pulmonary disease, purpura, gangrenous pioderma, Reiter's syndrome, diabetic retinopathy, rosacea, sarcoidosis, ataxic sclerosis, progressive systemic sclerosis, scleritis, sclerodermia, multiple sclerosis, disseminated sclerosis, acute anterior uveitis, vitiligo, Whipple's disease, diseases associated to AIDS, severe combined immunodeficiency and Epstein Barr's virus such as Sjögren's syndrome, osteoarticular tuberculosis and parasitic diseases such as leishmaniasis. Preferred inflammatory diseases are rheumatoid arthritis, psoriasis, sarcoidosis, diabetic retinopathy, macular degeneration, arteriosclerosis and obesity. In a more preferred embodiment the disease is psoriasis.

In one embodiment of the present invention, the medicament comprises one or more antibodies according to the invention as the sole therapeutic agent. However, the medicament of the invention can also contain one or several additional compounds for the treatment of cancer. Therefore, in another embodiment of the present invention, the medicament is prepared for the combined administration of an antibody according to the invention and one or more therapeutic agents useful in the treatment of said disease.

The term "therapeutic agent useful in the treatment of said disease" refers to an agent suitable for being used in the treatment of cancer.

For the treatment of cancer, the antibody of the invention can be used in combination with an additional therapeutically active compound, such as a cytotoxic agent, an antiangiogenic agent, an antimetastatic agent, an antiproliferative agent or an anti-inflammatory agent.

Cytotoxic agents which can be used in combination with the antibodies of the invention for the treatment of cancer include but are not limited to anthracycline antibiotics such as doxorubicin and daunorubicin, taxanes such as Taxol™ and docetaxel, vinca alkaloids such as vincristine and vinblastine, 5-fluorouracil (5-FU), leucovorin, irinotecan, idarubicin, mitomycin C, oxaliplatin, raltitrexed, tamoxifen, cisplatin, carboplatin, methotrexate, actinomycin D, mitoxantrone, blenoxane or mithramycin. Antiangiogenic agents which can be used in combination with the antibodies of the invention for the treatment of cancer include but are not limited to an antiangiogenic agent selected from the group of paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastal, penicillamine, PTK787/ZK 222584, RPL4610, squalamine lactate, SU5416, thalidomide, combretastatin, tamoxifen, COL-3, neovastat, BMS-275291, SU6668, anti-VEGF antibodies, Medi-522 (Vitaxin II), CA1, interleukin 12, IM862, amiloride, angiostatin, Kl-3 angiostatin, Kl-5 angiostatin, Captopril, DL-alpha-difluoromethylornithine, DL-alpha-difluoromethylornithine HC, endostatin, fumagillin, herbimycin A, 4-hydroxyphenylretinamide, juglone, laminin, laminin hexapeptide, laminin pentapeptide, lavendustin A, medroxyprogesterone, minocycline, placenta ribonuclease inhibitor, suramin, thrombospondin, antibodies directed against proangiogenic factors (for example, Avastin, Erbitux, Vectibix, Herceptin); low molecular weight tyrosine kinase inhibitors of proangiogenic growth factors (for example Tarceva, Nexavar, Sutent, Iressa); mTOR inhibitors (for example Torisel); interferon alpha, beta and gamma. IL-12, matrix metalloproteinase inhibitors (for example, COL3, marimastat, batimastat); ZD6474, SU11248, vitaxin; PDGFR inhibitors (for example Gleevec); NM3 and 2-ME2; cyclopeptides such as cilengitide. Antimetastatic agents which can be used in combination with the antibodies of the invention for the treatment of cancer include but are not limited to any agent capable of acting as an antimetastatic agent, such as alkylating agents; antimetabolites such as 5-fluorouracil, pemetrexed (MTA), raltitrexed (TDX), platinum cytotoxic agents such as cisplatin or oxaliplatin; topoisomerase inhibitors; antimicrotubule agents; anthracyclines; plant alkaloids; GTPase inhibitors; angiogenesis inhibitors; matrix metalloproteinase inhibitors; inhibitors of the cell cycle regulating kinase, such as cyclin-dependent kinases and cyclin inhibitors; Wan signaling inhibitors; inhibitors of the E2F transcription factor; histone deacetylase inhibitors; AKT kinase or ATPase inhibitors. Antiproliferative agents are agents capable of preventing or inhibiting the formation or growth of tumors. Antiproliferative agents which can be used in combination with the antibodies of the invention for the treatment of cancer include but are not limited to (i) antimetabolites such as folic acid antimetabolites (aminopterin, denopterin, methotrexate, edatrexate, trimetrexate, nolatrexed, lometrexol, pemetrexed, raltitrexed, piritrexin, pteropterin, leucovorin, 10-propargyl-5,8-didenazafolate (PDDF, CB3717)), purine analogs (cladribine, clofarabine, fludarabine, mercaptopurine, pentostatin, thioguanine) and pyrimidine analogs (capecitabine, cytarabine or ara-C, decitabine, fluorouracil, 5-fluorouracil, doxifluridine, floxuridine and gemcitabine) (ii) natural products, such as antitumor antibiotics and mitotic inhibitors such vinca alkaloids such as vindesine, vincristine, vinblastine, vinorelbine; taxanes such as paclitaxel (Taxol™), docetaxel (Taxotere™); colchicine (NSC 757), thiocolchicine (NSC 361792), colchicine derivatives (e. g., NSC 33410), and allocolchicine (NSC 406042); halichondrin B (NSC 609395); dolastatin 10 (NSC 376128); maytansine (NSC 153858); rhizoxin (NSC 332598); epothilone A, epothilone B; discodermolide; estramustine; nocodazole; (iii) hormones and antagonists thereof, such tamoxifen, toremifene, anastrozole, arzoxifene, lasofoxifene, raloxifene, nafoxidine, fulvestrant, aminoglutethimide, testolactone, atamestane, exemestane, fadrozole, formestane, letrozole, goserelin, leuprorelin or leuprolide, buserelin, histrelin, megestrol and fluoxymesterone; (iv) biological agents, such as viral vectors, interferon alpha and interleukines; (v) platinum based compounds such as carboplatin, cisplatin [cis-diamminedichloroplatinum, (CDDP)], oxaliplatin, iproplatin, nedaplatin, triplatin tetranitrate, tetraplatin, satraplatin (JM216), JM118 [cis ammine dichloro (II)], JM49 [cis ammine dichloro (cyclohexylamine) trans dihydroxo platinum (IV)], JM335 [trans ammine dichloro dihydroxo platinum (IV)], transplatin, ZD0473, cis, trans, cis-Pt(NH3)(C6H11NH2)(OOCC3H7)2Cl, malanate-1,2-diaminociclohexanoplatin(II), 5-sulphosalycilate-trans-(1,2-diaminociclohexane)platin (11) (SSP), poly-[(trans-1,2-diaminocyclohexane)platin]-carboxyamilose (POLY-PLAT) and 4-hydroxy-sulphonylphenylacetate (trans-1,2-diaminocyclohexane) platinum (II) (SAP) and the like and (vi) DNA-alkylating drugs such as nitrogen mustards, nitrosoureas, ethylenimine derivatives, alkyl sulfonates and triazenes, including, but not limited to, cyclophosphamide (Cytoxan™), busulfan, improsulfan, piposulfan, pipobroman, melphalan (L-sarcolysin), chlorambucil, mechlorethamine or mustine, uramustine or uracil mustard, novembichin, phenesterine, trofosfamide, ifosfamide, carmustine (BCNU), lomustine (CCNU), chlorozotocin, fotemustine, nimustine, ranimnustine, semustine (methyl-CCNU), streptozocin, thiotepa, triethylenemelamine, triethylenethiophosphoramine, procarbazine, altretamine, dacarbazine, mitozolomide and temozolomide.

Anti-inflammatory agents which can be used in combination with the antibodies of the invention for the treatment of cancer include but are not limited to any agent capable of acting as anti-inflammatory agent such 5-aminosalicylic acid and medicaments containing it (sulfasalazine, mesalamine, mesalazine, osalazine); acetylsalicylic acid; corticosteroids such hydrocortisone, cortisone, triameinolone, budesonide, prednisone, deflazacort, methotrexate; infliximab or adalimumab.

As "combined administration" it is understood that the antibody according to the invention is administered jointly or separately, simultaneously, at the same time or sequentially with a therapeutic agent useful in the treatment of cancer in any order. For example, the administration of the antibody of the invention can be done first, followed by the administration of one or more therapeutic agents useful in the treatment of said pathology; or the administration of the antibody of the invention can be done last, preceded by the administration of one or more therapeutic agents useful in the treatment of said pathology; or the administration of the antibody of the invention can be done at the same time as the administration of one or more therapeutic agents useful in the treatment of said pathology.

The person skilled in the art will understand that in the context of the present invention, the medicament for the combined administration of an antibody according to the invention and an additional therapeutic agent useful in the treatment of cancer can be prepared as a single dosage form or in separate dosage forms.

In a particular embodiment, the antibody used is a monoclonal antibody produced by a hybridoma selected from the group consisting of ECACC 13020701, ECACC 13020702, ECACC 13020703, ECACC 13020704, ECACC 13020705 and ECACC 13020706 or a functional variant of said antibody as will later be described in the context of the monoclonal antibodies of the invention.

The terms "monoclonal antibody" and "hybridoma" are defined below in the context of the second aspect of the invention.

"Functional variant" of the monoclonal antibodies of the invention is understood as any molecule sharing with said monoclonal antibodies one or more of the functions described in the present invention associated with said monoclonal antibodies, both in vitro and in vivo, and having a minimal identity in the amino acid sequence. The functional variants of the monoclonal antibodies of the invention can be derived from said sequences by means of insertion, substitution or deletion of one or more amino acids and can be obtained by recombinant and/or synthetic means.

The functional variants of the monoclonal antibodies of the invention must conserve their capacity for binding to the S100A7 antigen and also the capacity for inhibiting one or more characteristic functions of the S100A7 protein, such as the interaction of the S100A7 protein with one or more of its ligands, especially with its RAGE ligand, and/or the inhibition of one or more of the functions mediated by S100A7, such as the tumor cell proliferation, metastasis, the formation of tumor spheres or endothelial cell migration and proliferation. Said functions can be determined by means of the methods described in the examples of the present invention.

The functional variants of the monoclonal antibodies of the invention include polypeptides showing at least 60%, 65%, 70%, 72%, 74%, 76%, 78%, 80%, 90%, 95%, 97%, 99% similarity or identity with the polypeptide sequence of said antibodies. The degree of identity between two polypeptides is determined using algorithms implemented in a computer and methods which are widely known by the persons skilled in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

Inflammation

The S100A7 protein is expressed in diseases associated with inflammation such as psoriasis (Anderson et al., Br. J. Dermatol, 2009; 160(2): 325-32). As a result, the S100A7 protein ligands, and more specifically, antibodies specific against this protein, are candidate drugs to be used in therapy for the treatment of said diseases.

Thus, in another aspect, the invention relates to an antibody which binds specifically to the S100A7 protein or a fragment thereof with capacity for binding to the antigen for use in the prevention and/or treatment of a disease associated with inflammation.

Said antibody or fragment thereof can also have antimetastatic activity and/or antiangiogenic activity but it is not necessary.

In another aspect, the invention relates to the use of an antibody which binds specifically to the S100A7 protein or a fragment thereof with capacity for binding to the antigen for the preparation of a medicament for the prevention and/or treatment of a disease associated with inflammation.

In another aspect, the invention relates to a method of treatment or prevention of a disease associated with inflammation in a subject which comprises the administration to said subject of an antibody which binds specifically to the S100A7 protein or of a fragment thereof with capacity for binding to the antigen.

The terms "antibody", "fragment" and "antigen" have been previously defined.

The antibody fragments included in the present invention conserve the capacity for binding to the S100A7 antigen of the whole antibody they derive, and they also conserve the function of inhibiting one or more characteristic functions of the S100A7 protein, such as binding activity and/or stimulation of a cell response. For example, in one embodiment, an antibody fragment can inhibit the interaction of the S100A7 protein with one or more of its ligands, especially with its RAGE ligand, and/or it can inhibit one or more functions mediated by said protein such as TNF alpha secretion by tumor cells.

In this context, the term "TNF alpha or TNF-α" refers to tumor necrosis factor-alpha which is a cytokine involved in systemic inflammation and is a member that stimulate the acute phase reaction. It is produced chiefly by activated macrophages (M1), although it can be produced by many other cell types as CD4+ lymphocytes, natural killer cells and neurons. Sustained presence of TNF-α in the tumor microenvironment is also related with an enhanced inflammation and tumor progression (Szlosarek et al., 2006, Eur. J, Cancer, 42(6): 745-50).

The terms "RAGE" and "antibody capable of inhibiting the interaction of the S100A7 protein with RAGE" have been previously defined. Said antibodies conserve the function of inhibiting one or more characteristic functions of the S100A7 protein, such as binding activity, signaling activity and/or the stimulation of a cell response. Said inhibition of the interaction can be evaluated by means of the assays described in examples of the present invention. For example, in one embodiment, one or more antibodies of the invention can inhibit one or more function mediated by the S100A7 protein such as TNF alpha secretion by tumor cells shown in Example 9.

As used herein, the term "S100A7" refers to a protein belonging to the family of calcium binding proteins called S100 which is associated to inflammation. The term also includes all the physiologically relevant post-translational chemical modifications forms, for example, glycosylation, phosphorylation or acetylation, etc., provided that the functionality of the protein is maintained. Said term encompasses the S100A7 of any mammal species, including but not being limited to domestic and farm animals (cows, horses, pigs, sheep, goats, dogs, cats or rodents), primates and humans. Preferably, the S100A7 is human.

The terms "human S100A7" and "functionally equivalent variants of S100A7" have been previously defined.

The variants of S100A7 contemplated in the first aspect of the present invention show the capacity of inhibiting the TNF alpha secretion by tumor cells induced by S100A7 protein.

As mentioned previously, modifications in the amino acid sequence of the antibody of the invention are also contemplated.

The expression "disease associated with inflammation" relates to all those diseases where pathogenic inflammation occurs i.e. when said process is harmful or undesirable, whether cancerous or not. Diseases associated with inflammation include inflammatory diseases, where there is an excessive or altered inflammatory response that leads to inflammatory symptoms. Said inflammatory diseases which may be treated by the antibodies of the invention include, without limitation, Addison's disease, acne vulgaris, alopecia areata, amyloidosis, ankylosing spondylitis, ulcerations, aphthous stomatitis arthritis, arthritis, arteriosclerosis, osteoarthritis, rheumatoid arthritis, bronchial asthma, Bechet's disease, Boeck's disease, intestinal inflammatory disease, Crohn's disease, choroiditis, ulcerative colitis, celiac's disease, cryoglobulinemia, macular degeneration, dermatitis, dermatitis herpetiformis, dermatomyositis, insulin dependent diabetes, juvenile diabetes, inflammatory demyelinating disease, Dupuytren contracture, encephalomyelitis, allergic encephalomyelitis, endophthalmia, allergic enteritis, autoimmune enteropathy syndrome, erythema nodosum leprosum, ankylosing spondylitis, idiopathic racial paralysis, chronic fatigue syndrome, rheumatic fever, cystic fibrosis, gingivitis, glomerulonephritis, Goodpasture syndrome, Graves syndrome, Hashimoto's disease, chronic hepatitis, histiocytosis, regional ileitis, iritis, disseminated lupus erythematous, systemic lupus erythematous, cutaneous lupus erythematous, lymphogranuloma, infectious mononucleosis, miastenia gravis, transverse myelitis, primary idiopathic myxedema, nephrosis, obesity, sympathetic ophthalmia, granulomatous orchitis, pancreatitis, panniculitis, pemphigus vulgaris, periodontitis, polyarteritis nodosa, chronic polyarthritis, polymyositis, acute polyradiculitis, psoriasis, chronic obstructive pulmonary disease, purpura, gangrenous pioderma, Reiter's syndrome, diabetic retinopathy, rosacea, sarcoidosis, ataxic sclerosis, progressive systemic sclerosis, scleritis, sclerodermia, multiple sclerosis, disseminated sclerosis, acute anterior uveitis, vitiligo, Whipple's disease, diseases associated with AIDS, severe combined immunodeficiency and Epstein Barr's virus such as Sjögren's syndrome, osteoarticular tuberculosis and parasitic diseases such as leishmaniasis. Preferred inflammatory diseases are rheumatoid arthritis, arteriosclerosis, psoriasis, inflammatory bowel disease and graft-versus-host disease. In a more preferred embodiment the inflammatory disease is psoriasis.

In one embodiment of the present invention, the medicament comprises one or more antibodies according to the invention as the sole therapeutic agent. However, the medicament of the invention can also contain one or several additional compounds for the treatment of diseases associated to inflammation. Therefore, in another embodiment of the present invention, the medicament is prepared for the combined administration of an antibody according to the invention and one or more therapeutic agents useful in the treatment of said diseases. The terms "medicament", "prevention" and "treatment" have been previously defined.

The term "therapeutic agent useful in the treatment of said disease" refers to an agent suitable for being used in the treatment of a disease associated with inflammation.

Anti-inflammatory agents which can be used in combination with the antibodies of the invention include but are not limited to any agent capable of acting as antiinflammatory agent such as 5-aminosalicylic acid ad medicaments containing it (sulfasalazine, mesalamine, mesalazine, osalazine); acetylsalicic acid; corticosteroids such hydrocortisone, cortisone, triamcinolone, budesonide, prednisone, deflazacort, methotrexate; infliximab or adalimumab.

As "combined administration" it is understood that the antibody according to the invention is administered jointly or separately, simultaneously, at the same time or sequentially with a therapeutic agent useful in the treatment of a disease associated with inflammation in any order. For example, the administration of the antibody of the invention can be done first, followed by the administration of one or more therapeutic agents useful in the treatment of said pathology; or the administration of the antibody of the invention can be done last, preceded by the administration of one or more therapeutic agents useful in the treatment of said pathology; or the administration of the antibody of the invention can be done at the same time as the administration of one or more therapeutic agents useful in the treatment of said pathology.

In a particular embodiment, the antibody used is a monoclonal antibody produced by a hybridoma selected from the group consisting of ECACC 13020701, ECACC 13020702, ECACC 13020703, ECACC 13020704, ECACC 13020705 and ECACC 13020706 or a functional variant of said antibody as will later be described in the context of the monoclonal antibodies of the invention.

The terms "monoclonal antibody" and "hybridoma" are defined below in the context of the second aspect of the invention.

The term "functional variant" of the monoclonal antibodies of the invention has been defined previously. The functional variants of the monoclonal antibodies of the invention must conserve their capacity for binding to the S100A7 antigen and also the capacity for inhibiting one or more characteristic functions of the S100A7 protein, such as the interaction of the S100A7 protein with one or more of its ligands, especially with its RAGE ligand, and/or the inhibition of one or more of the functions mediated by S100A7, such as the secretion of TNF-α.

Monoclonal Antibodies of the Invention

In a second aspect, the invention relates to a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7.

As it is used herein, the term "antibody" refers to an immunoglobulin showing specific binding activity towards a target molecule or antigen, which in this specific case is the S100A7 protein.

In the present document, the "antigen" is the molecule to which an antibody specifically binds. Specifically, the antigen for the antibodies of the invention is the S100A7 protein.

The antibodies of the invention are capable of binding to an epitope of the S100A7 protein. The term "epitope" or "antigenic determinant" includes any region of an antigen which is specifically recognized by an antibody. One and the same antigen can have different epitopes. Each epitope usually consists of clusters of chemically active surfaces of molecules such as amino acids or sugar side chains, which have specific three-dimensional structural characteristics, as well as specific charge characteristics. At least 6, 8, 10 or 12 contiguous amino acids are typically required to form an epitope. However, the epitopes involving non-contiguous amino acids may require more, for example, at least 15, 25 or 50 amino acids.

In the context of this second aspect, a "specific anti-S100A7 monoclonal antibody" is a homogenous antibody produced by a hybrid cell or hybridoma which is capable of specifically recognizing a specific epitope of the S100A7 protein, but it does not recognize other proteins of the S100 family. The monoclonal antibodies of the invention preferably recognize human S100A7, but they can also recognize the S100A7 protein of other mammal species as has been described in the context of the first aspect of the invention. In preferred embodiments of the invention, the monoclonal antibody is any of those mentioned in this second aspect of the invention.

The term S100A7 has been defined in the context of the first aspect of the invention and also includes the functionally equivalent variants of S100A7.

In the context of the present invention, "hybrid cell" or "hybridoma" is understood as the product of the fusion of a B-cell clone descendent of a single unique stem cell, and of a myeloma cell. Specifically, the monoclonal antibodies of the second aspect of the invention correspond with the anti-S100A7 monoclonal antibodies referred to in the experimental part of the present document as 2D9, 2H3, 6E3, 6F5, 8B6 and 9F3, which have been obtained from the hybridomas generated by the inventors and identified as 2D9-1C4-3D7-5E6, 2H3-1A12-5E12-1A4, 6E3-2D5-1F9-5B4, 6F5-2F8-2G9-1A2, 8B6-1A9-5A8-8G2 and 9F3-3E6-2D7-3B3, respectively. Said hybridomas have been deposited prior to filing the present patent application in the European Collection of Cell Cultures (ECACC), Porton Down, Salisbury, SP4 OJG, United Kingdom, as a legally recognized institution for that purpose in accordance with the Budapest Treaty, of 28 Apr. 1977, on the International Recognition of the Deposit of Microorganisms.

The European Collection of Cell Cultures (ECACC) has assigned to hybridomas 2D9-1C4-3D7-5E6, 2H3-1A12-5E12-1A4, 6E3-2D5-1F9-5B4, 6F5-2F8-2G9-1A2, 8B6-1A9-5A8-8G2 and 9F3-3E6-2D7-3B3 the respective deposit numbers, ECACC 13020701, ECACC 13020702, ECACC 13020703, ECACC 13020704, ECACC 13020705 and ECACC 13020706. The culture conditions of said hybridoma lines which allow obtaining the anti-S100A7 monoclonal antibodies of the invention are described in the context of the method for obtaining the monoclonal antibodies of the invention.

In the present document, hybridomas 2D9-1C4-3 D7-5E6, 2H3-1A12-5E12-1A4, 6E3-2D5-1F9-5B4, 6F5-

2F8-2G9-1A2, 8B6-1A9-5A8-8G2 and 9F3-3E6-2D7-3B3 and the antibodies produced by said hybridomas are indicated by means of their abbreviated name 2D9, 2H3, 6E3, 6F5, 8B6 and 9F3 respectively.

The invention also contemplates polypeptides having at least one fragment of the sequence of the specific anti-S100A7 monoclonal antibodies of the second aspect of the invention which maintain the capacity for binding to S100A7. Said capacity for binding can be checked by means of methods known by the person skilled in the art, such as ELISA, Western blot or immunocytochemical or immunohistochemical techniques as described in Examples 4, 5, and 6 of the present invention.

"Polypeptides" are understood as molecules formed by the binding of at least 10 amino acids by means of peptide bonds. The polypeptides of the invention must have at least one fragment of the sequence of the mentioned specific anti-S100A7 monoclonal antibodies. Said "fragment of the sequence" can correspond to one or several portions of the amino acid sequence of the mentioned monoclonal antibody which maintains the capacity for binding to S100A7, and therefore, the polypeptide must include the sequence of the 6 CDR regions, which can be used for obtaining the antibodies defined in the context of the first aspect of the invention, such as, without limitation, genetically engineered antibodies such as chimeric antibodies, humanized antibodies or bispecific antibodies. Said "fragment of the sequence" can also be used for obtaining antibody fragments such as Fab, F(ab')$_2$, Fab', single chain Fv fragments (scFv), diabodies or nanobodies.

The Fab and F(ab')$_2$ fragments can be obtained by means of enzymatic or chemical cleavage of the intact monoclonal antibodies of the second aspect of the invention.

Papain digestion of a monoclonal antibody of the invention produces two identical antigen binding fragments referred to as "Fab" fragments, each with a single antigen binding site. In turn, the "F(ab')$_2$" fragment, which has two antigen binding sites, is obtained by pepsin treatment.

Additionally, the "fragment of the sequence" allows obtaining another type of antibody fragments such as Fab' fragments, single chain Fv fragments (scFv) or diabodies by means of genetic engineering techniques.

The monoclonal antibodies of the second aspect of the invention have demonstrated that they are capable of neutralizing tumor cell proliferation. Therefore, in a particular embodiment, the invention relates to a monoclonal antibody produced by a hybridoma selected from ECACC 13020701, ECACC 13020702, ECACC 13020703, ECACC 13020704, ECACC 13020705 and ECACC 13020706 or a polypeptide having at least one fragment of the sequence of said monoclonal antibody which is capable of stopping the growth of tumor cells.

"Stopping the growth of tumor cells" is understood as the inhibition of the proliferation of said tumor cells by at least 25%, 30%, 35%, 40%, 45%, 50%, 60%, 70%, 75%, 80%, 85%, 90%, 95%, 99%, 100%; preferably at least 30%; more preferably at least 35%; still more preferably at least 60%; most preferably at least 65%. Said inhibition of the proliferation or stop of the growth can be evaluated by means of the assays described in Examples 11 and 15 of the present invention.

The monoclonal antibodies of the second aspect of the invention have demonstrated that they are capable of neutralizing tumor cell migration. Therefore, in a particular embodiment, the invention relates to a monoclonal antibody produced by a hybridoma selected from ECACC 13020701, ECACC 13020702, ECACC 13020703, ECACC 13020704, ECACC 13020705 and ECACC 13020706 or a polypeptide having at least one fragment of the sequence of said monoclonal antibody which is capable of stopping the migration of tumor cells.

"Stopping the migration of tumor cells" is understood as inhibition of the migration of said tumor cells by at least 25%, 30%, 35%, 40%, 45%, 50%, 60%, 70%, 75%, 80%, 85%, 90%, 95%, 99%, 100% with respect to the migration in untreated cells; preferably at least 55%; more preferably at least 60%; still more preferably at least 65%; most preferably at least 70%; still more preferably at least 80%; even more preferably at least 90%. Said inhibition of the migration can be evaluated by means of the assays described in Example 12 of the present invention.

The monoclonal antibodies of the second aspect of the invention have demonstrated that they are capable of neutralizing tumor spheres formation. Therefore, in a particular embodiment, the invention relates to a monoclonal antibody produced by a hybridoma selected from ECACC 13020701, ECACC 13020702, ECACC 13020703, ECACC 13020704, ECACC 13020705 and ECACC 13020706 or a polypeptide having at least one fragment of the sequence of said monoclonal antibody which is capable of inhibiting the formation of tumor spheres.

"Inhibiting the formation of tumor spheres" is understood as inhibition of the formation of said tumor spheres by at least 25%, 30%, 35%, 40%, 45%, 50%, 60%, 70%, 75%, 80%, 85%, 90%, 95%, 99%, 100% with respect to untreated cells; preferably at least 55%; more preferably at least 60%; still more preferably at least 65%; most preferably at least 70%. Said inhibition of the formation of tumor spheres can be evaluated by means of the assays described in Example 10 of the present invention.

"Tumor cell" is understood as a malignant cell, also known as a cancerous or carcinogenic cell which grows and divides beyond the normal limits, invading the surrounding tissue and sometimes causing metastasis. The tumor cells that can be treated with the antibodies of the present invention are cells which overexpress the S100A7 protein. Said cells include tumor cells from known and established cell lines and tumor cells present in the organism of a patient suffering from cancer. Several illustrative non-limiting examples of known tumor lines which overexpress S100A7 are MDA-MB-468 and MCF-7. Illustrative non-limiting examples of tumor cells present in a patient suffering from cancer and which overexpress S100A7 are tumor cells from breast tumors (Ethan et al., Clin. Can. Res., 2003, 9:2627-2631; Nasser et al., Cancer Res., 2012, 72:604-615), gastric tumors (El-Rifai et al., Cancer Res., 2002, 62:6823-6826), lung tumors (Zhang et al, Thorax, 2008, 63(4): 352-359), bladder tumors (Ostergaard M et al., Cancer Res, 1997: 57:4111-4117), epithelial skin tumors (Moubayed et al., J Cancer Res Clin Oncol, 133:253-61; Alowami et al, BMC Dermatol, 3:1), head and neck tumors (Tripathi et al., Plos One, 2010, 5(8):e11939), ovarian tumors (Gagnon et al., Clin. Cancer Res., 2008, 14(3):764-761).

The tumor cells which express the S100A7 protein can be identified by means of conventional methods such as ELISA or Western blot, according to the method described in the present invention.

In one embodiment, the tumor cells the growth of which is stopped by means of the antibodies of the invention are tumor cells of any type of tumor with the exception of breast cancer. In another embodiment the tumor cells the growth of which is stopped by means of the antibodies of the invention are colorectal carcinoma tumor cells. In another embodiment the tumor cells the growth of which is stopped by means of the antibodies of the invention are fibrosarcoma tumor cells. In another embodiment the tumor cells the growth of which is stopped by means of the antibodies of the invention are breast tumor cells.

The antibodies of the invention are also capable of showing antimetastatic activity. Thus, in a preferred embodiment the monoclonal antibody or polypeptide according to the invention is antimetastatic.

"Antimetastatic" is understood as a chemical or biological substance which inhibits or reduces metastasis, i.e., the distance propagation, fundamentally by the lymphatic or blood stream, of the cancer causing cells, and the growth of new tumors in the destination sites of said metastasis. Preferably, the antimetastatic antibody or fragment thereof of the invention is understood as the inhibition of the metastasis of said tumor cells by at least 25%, 30%, 35%, 40%, 45%, 50%, 60%, 70%, 75%, 80%, 85%, 90%, 95%, 99%, 100%.

The monoclonal antibodies of the second aspect of the invention are capable of inhibiting angiogenesis or neovascularization. Therefore, in a particular embodiment, the invention relates to a monoclonal antibody produced by a hybridoma selected from ECACC 13020701, ECACC 13020702, ECACC 13020703, ECACC 13020704, ECACC 13020705 and ECACC 13020706 or a polypeptide having at least one fragment of the sequence of said monoclonal antibody which is capable of inhibiting the proliferation of endothelial cells and/or which is capable of stopping the migration capacity of endothelial cells.

"Inhibiting the proliferation of endothelial cells" is understood as inhibition of the proliferation of said cells by at least 25%, 30%, 35%, 40%, 45%, 50%, 60%, 70%, 75%, 80%, 85%, 90%, 95%, 99%, 100% with respect to the migration in untreated cells; preferably at least 55%; more preferably at least 60%; still more preferably at least 65%; most preferably at least 70%; more preferably at least 80%; still more preferably at least 90%.

The expression "migration capacity of endothelial cells" refers to the capacity of said cells of moving which is a key step in neovasculature formation. In a preferred embodiment said cells are human endothelial cells that are cells lining all the vessels of a mammalian organism. Human endothelial cells included in said definition are, without limitation, human umbilical vein endothelial cells (HUVECs). In a preferred embodiment the human endothelial cells are HUVECs cells.

The monoclonal antibodies of the second aspect of the invention have demonstrated that they are capable of blocking the secretion of active forms of metalloproteinase MMP9. Therefore, in a particular embodiment, the invention relates to a monoclonal antibody produced by a hybridoma selected from ECACC 13020701, ECACC 13020702, ECACC 13020703, ECACC 13020704, ECACC 13020705 and ECACC 13020706 or a polypeptide having at least one fragment of the sequence of said monoclonal antibody which is capable of blocking the secretion of active forms of metalloproteinase MMP9.

The expression "blocking the secretion of active forms of metalloproteinase MMP9", is understood as inhibition of the secretion of said active forms by at least 25%, 30%, 5%, 40%, 45%, 45%, 50%, 60%, 65%, 70%, 75%, 80%, 85%, 90%, 95%, 99%, 100% with respect to the secretion in untreated cells; preferably at least 70%; more preferably at least 80%; more preferably at least 90%; still more preferably at least 95%; even more preferably at least 99%; the most preferred 100%.

The monoclonal antibodies of the second aspect of the invention have demonstrated that they are capable of neutralizing the secretion of TNF-α by tumor cells which is associated with inflammation. Therefore, in a particular embodiment, the invention relates to a monoclonal antibody produced by a hybridoma selected from ECACC 13020701, ECACC 13020702, ECACC 13020703, ECACC 13020704, ECACC 13020705 and ECACC 13020706 or a polypeptide having at least one fragment of the sequence of said monoclonal antibody which is capable of inhibiting secretion of TNF-α.

"Inhibiting the secretion of TNF-α" is understood as inhibition of the secretion of said TNF-α by at least 25%, 30%, 35%, 40%, 45%, 50%, 60%, 70%, 75%, 80%, 85%, 90%, 95%, 99%, 100% with respect to the migration in untreated cells; preferably at least 55%; more preferably at least 60%; still more preferably at least 65%; preferably at least 70%; more preferably at least 80%; still more preferably at least 90%.

The monoclonal antibodies of the second aspect of the invention have demonstrated that they are capable of blocking the migration of monocites which is associated with inflammation. Therefore, in a particular embodiment, the invention relates to a monoclonal antibody produced by a hybridoma selected from ECACC 13020701, ECACC 13020702, ECACC 13020703, ECACC 13020704, ECACC 13020705 and ECACC 13020706 or a polypeptide having at least one fragment of the sequence of said monoclonal antibody which is capable of blocking the migration of monocytes. In a preferred embodiment the monocytes are human monocytic cell line THP-1.

The expression "blocking the migration of monocytes", is understood as inhibition of the migration of monocytes by at least 25%, 30%, 35%, 40%, 45%, 50%, 55%, 60%, 65%, 70%, 75%, 80%, 85%, 90%, 95%, 99%, 100% with respect to the migration in untreated cells; preferably at least 40%; more preferably at least 50%; more preferably at least 70%; more preferably at leas 80%; more preferably at least 90%; still more preferably at least 95%; even more preferably at least 99%.

In another aspect, the invention relates to a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 for its use in medicine.

Method for Obtaining the Monoclonal Antibodies of the Invention

In another aspect, the invention relates to a method for obtaining a monoclonal antibody according to the second aspect of the invention which comprises culturing a hybridoma cell line selected from those cell lines deposited with accession number ECACC 13020701, ECACC 13020702, ECACC 13020703, ECACC 13020704, ECACC 13020705 and ECACC 13020706 in conditions which allow the production of said antibody.

The method for obtaining the monoclonal antibodies of the second aspect of the invention can be performed according to conventional methods known in the state of the art. Basically, the method consists of culturing the hybridoma cell line in a culture medium suitable for the hybridoma cells to produce antibodies and to secrete them into the medium, and of subsequently collecting the supernatant of the culture medium containing the monoclonal antibodies produced. Said antibodies can optionally be purified by conventional means, such as affinity chromatography, protein A sepharose, hydroxyapatite chromatography, gel electrophoresis or dialysis.

The term "monoclonal antibody" has already been defined in the previous aspect.

"Culturing" a hybridoma cell line is understood as incubating the hybridoma cells in the presence of a suitable medium in culture vials for the necessary time and in the suitable conditions for the multiplication of said cells and the production of the monoclonal antibodies of the invention to occur. Said culture can involve the use of culture media with different compositions. Preferably, in a first step the cells are cultured in a medium containing serum to favor their multiplication and, after collecting the cells and washing them, they are cultured in a serum-free medium to obtain antibodies. Culture media suitable for obtaining the antibodies according to this method are, without limitation, DMEM/F12 supplemented with L-Glutamine and Fetal Calf Serum to favor cell multiplication and a mixture based on the DMEM/F12 medium supplemented with L-glutamine but lacking Fetal Calf Serum ("protein free medium") as an antibody collection medium. The medium for producing antibodies could also consist of any medium or mixture of synthetic cell culture mediums the composition and subsequent supplementation of which does not include proteins ("protein free medium") or said proteins are in a very low proportion ("serum free medium" or "low protein medium") and they do not belong to the group of immunoglobulins. Said medium must allow the cell growth and maintenance as well as the secretion of antibodies by the hybridoma cell line previously adapted to grow in the absence of Fetal Calf Serum. In a preferred embodiment the medium suitable for the culture of said cells is a medium comprising DMEM/F12 and L-glutamine. The conditions in which said culture are performed are preferably in a humid environment and at a temperature of 37° C. with standard air atmosphere or 5% $CO_2$ enriched air.

Therefore, in another aspect the invention relates to a hybridoma cell line selected from those cell lines deposited with accession number ECACC 13020701, ECACC 13020702, ECACC 13020703, ECACC 13020704, ECACC 13020705 and ECACC 13020706.

The expression "hybridoma cell line" refers to a cell line formed by hybrid cells or hybridomas as previously defined in the second aspect of the invention. Said hybridoma cell line has been obtained by standard methodologies as described in Examples 2 and 3 of the present invention. Briefly, mice were immunized with a human recombinant S100A7 protein and cells were extracted from the spleen of the immunized mouse, which were fused with myeloma cells in the presence of a fusion inducer such as PEG-1500. The hybridomas were selected in HAT medium and each selected clone was subcloned by limiting dilution. The clones suitable for expansion were adapted to the DMEM/F12 medium and were frozen, constituting the hybridoma cell lines ECACC 13020701, ECACC 13020702, ECACC 13020703, ECACC 13020704, ECACC 13020705 and ECACC 13020706.

In preferred embodiments of the invention, the monoclonal antibody prepared by means of this method can be any of those produced by the hybridoma cell lines described in the context of the present invention.

Pharmaceutical Compositions of the Monoclonal Antibodies of the Invention

In another aspect, the invention relates to a pharmaceutical composition comprising a pharmaceutically effective amount of at least one monoclonal antibody according to the second aspect of the invention or a polypeptide having at least one fragment of the sequence of said monoclonal antibody with capacity for binding to S100A7 and at least one pharmaceutically acceptable excipient.

As it is used in the present invention, the expression "pharmaceutical composition" relates to a formulation that has been adapted for administering a predetermined dose of one or several therapeutic useful agents to a cell, a group of cells, an organ, a tissue or an animal in which there is an overexpression of the S100A7 protein.

"Pharmaceutically effective amount" is understood as an amount capable of providing a therapeutic effect, and which can be determined by the person skilled in the art by commonly used means.

The compositions of the invention can contain one or more monoclonal antibodies according to the second aspect of the invention or one or more polypeptides having at least one fragment of the sequence of said monoclonal antibodies with capacity for binding to S100A7.

The compositions of the invention can also contain one or several additional compounds for the prevention and/or treatment of pathologies in which there is an overexpression of the S100A7 protein, such as cancer. Said additional compounds such as cytotoxic agents, antiangiogenic agents, antimetastatic agents, antiproliferative agents and antiinflammatory agents can form part of the pharmaceutical composition as independent entities of the monoclonal antibodies or also forming conjugates with said antibodies.

The pharmaceutical compositions are prepared by conventional means with one or more pharmaceutically acceptable excipients.

"Pharmaceutically acceptable excipient" is understood a therapeutically inactive substance said to be used for incorporating the active ingredient and which is acceptable for the patient from a pharmacological/toxicological point of view and for the pharmaceutical chemist who manufactures it from a physical/chemical point of view with respect to the composition, formulation, stability, acceptation of the patient and bioavailability.

The number and the nature of the pharmaceutically acceptable excipients depend on the desired dosage form. The pharmaceutically acceptable excipients are known by the person skilled in the art (Faulí y Trillo C. (1993) "Tratado de Farmacia Galénica", Luzán 5, S. A. Ediciones, Madrid). Said compositions can be prepared by means of the conventional methods known in the state of the art ("Remington: The Science and Practice of Pharmacy", $20^{th}$ edition (2003) Genaro A. R., ed., Lippincott Williams & Wilkins, Philadelphia, US).

The pharmaceutical compositions containing a monoclonal antibody according to the second aspect of the invention or a polypeptide having at least one fragment of the sequence of said monoclonal antibodies with capacity for binding to S100A7 can be administered by any type of suitable route, such as by oral route, topical route, by inhalation or parenteral route so that the pharmaceutically acceptable excipients necessary for the formulation of the desired dosage form will be included. The preferred route of administration of the pharmaceutical composition is the endovenous route.

"Oral route" is understood as the pharmaceutical composition incorporated into the organism after deglutition. In a particular embodiment, the pharmaceutical composition of the invention can be in a dosage form suitable for its administration by oral route, whether it is solid or liquid. The dosage forms suitable for their administration by oral route can be tablets, capsules, syrups or solutions, and can contain any conventional excipient known in the art, such as binders, for example syrup, acacia, gelatin, sorbitol or polyvinylpyrrolidone; filling agents, for example lactose, sugar, corn starch, calcium phosphate, sorbitol or glycine; lubricants for compression, for example, magnesium stearate; disintegrating agents, for example starch, polyvinylpyrrolidone, sodium glycolate of starch or microcrystalline cellulose; or pharmaceutically acceptable wetting agents such as sodium lauryl sulfate. The solid oral compositions can be prepared by means of conventional processes of mixing, filling or compressing. Repetitive mixing operations can be used to completely distribute the active agent in those compositions that use high amounts of filling agents. Said operations are conventional in the art. The tablets can be prepared, for example, by means of wet or dry granulation, and optionally coating them according to the processes known in the common pharmaceutical practice, particularly with an enteric coating.

On the other hand, "topical route" is understood as an administration by non-systemic route, and includes the application of a pharmaceutical composition of the invention externally on the epidermis, in the oral cavity and the instillation of said composition into ears, eyes and nose, and in which it does not significantly enter the blood stream. "Systemic route" is understood as the administration by oral route, intravenous route, intraperitoneal route and intramuscular route. The amount of antibody required for the therapeutic or prophylactic effect will naturally vary according to the elected antibody, the nature and the severity of the illness that is going to be treated, and the patient.

"Inhalation" is understood as the administration by intranasal route and by oral inhalation. The dosage forms suitable for said administration, such as a formulation in aerosol or a meter dosed inhaler can be prepared by means of conventional techniques.

As it is used herein, the term "parenteral", includes administration by intravenous route, intraperitoneal route, intramuscular route or subcutaneous route. Subcutaneous, intramuscular and intravenous dosage forms of parenteral administration are generally preferred.

In one embodiment, the pharmaceutical compositions of the invention can be adapted for their parenteral administration, such as sterile solutions, suspensions or lyophilized products in the appropriate dosage unit form. The pharmaceutical compositions suitable for its injectable use include sterile aqueous solutions (when they are soluble in water), or dispersions and sterile powders for the extemporaneous preparation of sterile injectable solutions or dispersions. For its administration by intravenous route, some suitable carriers include saline solution buffered with phosphate (PBS). In all the cases, the composition must be sterile, and must be fluid to the point which that there exists easy ability for being injected. It must be stable in the preparation and storage conditions, and must be protected from the contamination action of microorganisms such as bacteria and fungi. The carrier can be a solvent or a dispersion medium which contains, for example, water, ethanol, a pharmaceutically acceptable polyol such as glycerol, propylene glycol, liquid polyethylene glycol and suitable mixtures thereof. Suitable fluidity can be maintained, for example, by means of using a coating such as lecithin, by means of maintaining the particle size required in the case of a dispersion and by means of using surfactants. The prevention of the action of the microorganisms can be achieved by means of various antibacterial and antifungal agents, for example, parabens, chlorobutanol, phenol, ascorbic acid, thiomersal, and the like. In most cases, it will be preferable to include isotonic agents, for example, sugars; polyalcohols such as mannitol, sorbitol; or sodium chloride in the composition. The prolonged absorption of the injectable compositions may be caused by the inclusion of an agent which delays the absorption, for example, aluminum and gelatin monostearate.

The injectable sterile solutions can be prepared by incorporating the active compound in the required amount in a suitable solvent with one or a combination of the aforementioned ingredients, as needed, followed by sterilization by filtration through sterile membranes. Generally, the dispersions are prepared by incorporating the active compound in a sterile vehicle containing a basic dispersion medium and the rest of the ingredients required from among those previously listed. In the case of sterile powders for the preparation of injectable sterile solutions, the preferred preparation processes are vacuum drying and lyophilization which give rise to a powder with the active ingredient plus any desired additional ingredient from a previously filtered sterile solution thereof. The antibody will usually be stored in lyophilized form or in solution. The compositions of therapeutic antibody are generally housed in a packaging which has a sterile access opening, for example, an intravenous solution bag or vial having an adaptor which allows recovering the formulation, such as a stopper that can be perforated by a hypodermic injection needle.

The pharmaceutical composition can be suitably administered by means of pulse infusion, for example, with decreasing doses of the antibody. Preferably, the dose is administered by means of injections, more preferably intravenous or subcutaneous injections, partly depending if the administration is acute or chronic.

In one embodiment, the pharmaceutical composition which contains the antibody of the second aspect of the invention is prepared with carriers which will protect said antibody from a rapid elimination from the body, such as a controlled release formulation, including implants and microencapsulated administration systems. Biodegradable biocompatible polymers such as ethylene vinylacetate, polyanhydrides, polyglycolic acid, collagen, polyorthoesters and polylactic acid can be used. The processes for preparing said formulations will be clear for persons skilled in the art. The materials can also be commercially obtained in Alza Corporation and Nova Pharmaceuticals, Inc.

The sustained release compositions also include preparations of antibody crystals suspended in suitable formulations which can maintain the crystals in suspension. These preparations, when they are injected by subcutaneous or intraperitoneal route may produce a sustained release effect. Other compositions also include antibodies trapped in liposomes. The liposomes containing such antibodies are prepared by means of known methods such as Epstein et al., Proc. Natl. Acad. Sci. USA, (1985) 82:3688-3692; Hwang et al., Proc. Natl. Acad. Sci. USA, (1980) 77:4030-4034; EP 52,322; EP 36,676; EP 88,046; EP 143,949.

The compositions of the invention are suitable for the administration into any type of mammal, preferably a human being.

In another aspect, the invention relates to a pharmaceutical composition according to the invention for use in medicine.

In another aspect, the invention relates to a pharmaceutical composition according to the invention for use in the prevention and/or treatment of cancer and/or prevention and/or treatment of a disease associated to an undesired angiogenesis.

In another aspect, the invention relates to a pharmaceutical composition according to the invention for use in the prevention and/or treatment of diseases associated with inflammation In another aspect, the invention relates to the use of a pharmaceutical composition according to the invention for the preparation of a medicament for the prevention and/or treatment of cancer and/or prevention and/or treatment of a disease associated to an undesired angiogenesis.

In another aspect, the invention relates to the use of a pharmaceutical composition according to the invention for the preparation of a medicament for the prevention and/or treatment of a disease associated with inflammation. In another aspect, the invention relates to a method of treatment or prevention of cancer and/or a disease associated to an undesired angiogenesis in a subject which comprises the administration to said subject of a composition according to the invention.

In another aspect, the invention relates to a method of treatment or prevention of a disease associated with inflammation n a subject which comprises the administration to said subject of a composition according to the invention.

Conjugates of the Monoclonal Antibodies of the Invention and their Uses

Given that the monoclonal antibodies of the invention are capable of binding to the S100A7 protein and that this protein is overexpressed in cancer and inflammatory processes, the monoclonal antibodies produced by a hybridoma selected from the group consisting of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 constitute agents suitable for carrying compounds with therapeutic activity towards the expression sites of S100A7.

The S100A7 protein is expressed, as has been detailed above, in a great variety of cancers.

Therefore, in another aspect, the invention relates to a conjugate comprising a monoclonal antibody produced by a hybridoma selected from ECACC 13020701, ECACC 13020702, ECACC 13020703, ECACC 13020704, ECACC 13020705 and ECACC 13020706 or a polypeptide having at least one fragment of the sequence of said monoclonal antibody and a second component selected from the group of:
  (a) cytotoxic agent,
  (b) an antiangiogenic agent,
  (c) an antimetastatic agent,
  (d) an antiproliferative agent and
  (e) an antiinflammatory agent "Conjugate" in the context of the present invention is understood as an assembly formed by an antibody according to the second aspect of the invention bound, linked or associated to a least one second component.

The terms "monoclonal antibody", "hybridoma", "polypeptide" and "fragment of the sequence" have been defined in the context of the second aspect of the invention.

"Second component" is understood as a molecule with therapeutic activity which is directed to its action site by means of the monoclonal antibody of the invention.

The S100A7 protein is overexpressed in tumor cells. Therefore, the monoclonal antibodies of the invention can be used to direct antitumor drugs to the expression sites. The S100A7 protein is expressed in diseases associated with inflammation such as psoriasis. Therefore, the monoclonal antibodies of the invention can be used to direct antiinflammatory drugs to the expression sites.

As used in the present invention, the term "cytotoxic agent" relates to an agent which is capable of promoting cell death and which has capacity for reducing the growth, stopping the growth or destroying cells and, particularly, rapidly proliferating cells and, yet more particularly, tumor cells. Cell death can be caused by any mechanism, such as for example apoptosis, although it is not limited to this cause, by the metabolism inhibition, the interference with the organization of the cytoskeleton or the chemical modification of the DNA. The term cytotoxic agent comprises any chemotherapy agent including small organic molecules, peptides, oligonucleotides and the like; toxins; enzymes; cytokines; radioisotopes or radiotherapy agents.

"Chemotherapy agents" are understood as chemical compounds such as, without limitation, anthracycline antibiotics such as doxorubicin and daunorubicin, taxanes such as Taxol™ and docetaxel, vinca alkaloids such as vincristine and vinblastine, 5-fluorouracil (5-FU), leucovorin, irinotecan, idarubicin, mitomycin C, oxaliplatin, raltitrexed, tamoxifen, cisplatin, carboplatin, methotrexate, actinomycin D, mitoxantrone, blenoxane or mithramycin.

"Toxin" is understood as a toxic agent which conjugates with the monoclonal antibody of the invention forming an immunotoxin. The conjugation of determined toxins with antibodies reduces the toxicity of the former, enabling their use as therapeutic agents, because otherwise they would be too toxic. The binding between the toxin and the antibody is performed chemically, conserving its biological activity. Their separation generally occurs in the lysosomes of the target cells recognized by the antibody such that the mentioned chemical binding is only broken in the enclosed acidic cellular environment provided by the lysosomes. Toxins useful in the context of the present invention are plant toxins, bacterial toxins, toxins of fungal or animal origin and fragments thereof, such as, without limitation, the ricin A-chain, saponin, the diphtheria A-chain, active non-binding fragments of the diphtheria toxin, *Pseudomonas aeruginosa* exotoxin A-chain, abrin A-chain, modecin A-chain, α-sarcin, *Leurites fordii* A-proteins, dianthin proteins, *Phytolaca americana* (PAPI, PAPII and PAP-S) proteins, *Momordica charantia* inhibitor, curcine, crotin, *Saponaria officinalis* inhibitor, gelonin, mitogelin, restrictocin, phenomycin, enomycin and trichothecenes.

"Enzymes" are understood in the context of the present invention as toxin or drug activating enzymes, such as, without limitation, alkaline phosphatase which activates etoposide and doxorubicin; carboxypeptidase G2 which activates nitrogen mustards; beta-lactamase which activates doxorubicin, paclitaxel and mitomycin.

"Cytokines" are understood as peptides of different sizes and molecular weights which synthesize the cells of the immune system for the purpose of regulating the immune response, and they can be hormones, growth factors, necrosis factors, etc. They can be of natural origin or from recombinant cell cultures and biologically active equivalents of natural sequence cytokines. Their conjugation with antibodies gives rise to immunocytokines. Cytokines useful in the present invention are, without limitation, TNF factor alpha, INF-gamma, GM-GSF factor or IL-2.

"Radioisotopes" is understood as radioactive isotopes such as, without limitation, $^{131}$I, $^{90}$Y, $^{177}$Lu, $^{188}$Re, $^{67}$Cu, $^{211}$At, $^{213}$Bi, $^{125}$I, $^{111}$In.

"Antiangiogenic agent" is understood as a chemical or biological substance which inhibits or reduces the formation of new blood vessels, i.e., angiogenesis.

Antiangiogenic agents that can be conjugated with the antibodies of the invention include, without limitation, an antiangiogenic agent selected from the group of paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, penicillamine, PTK787/ZK 222584, RPL4610, squalamine lactate, SU5416, thalidomide, combretastatin, tamoxifen, COL-3, neovastat, BMS-275291, SU16668, anti-VEGF antibodies, Medi-522 (Vitaxin II), CAI, interleukin 12, IM862, amiloride, angiostatin, Kl-3 angiostatin, Kl-5 angiostatin, Captopril, DL-alpha-difluoromethylornithine, DL-alpha-difluoromethylornithine HCl, endostatin, fumagillin, herbimycin A, 4-Hydroxyphenylretinamide, juglone, laminin, laminin hexapeptide, laminin pentapeptide, lavendustin A, medroxyprogesterone, minocycline, placenta ribonuclease inhibitor, suramin, thrombospondin, antibodies directed against proangiogenic factors ((or example, Avastin, Erbitux, Vectibix, Herceptin); low molecular weight tyrosine kinase inhibitors of proangiogenic growth factors (for example Tarceva, Nexavar, Sutent, Iressa); mTOR inhibitors (for example Torisel); interferon alpha, beta and gamma, IL-12, matrix metalloproteinase inhibitors (for example, COL3, marimastat, batimastat); ZD6474, SU11248, vitaxin; PDGFR inhibitors (for example Gleevec); NM3 and 2-ME2; cyclopeptides such as cilengitide.

"Antimetastatic agent" is understood as a chemical or biological substance which inhibits or reduces metastasis, i.e., the distance propagation, fundamentally by the lymphatic or blood stream, of the cancer causing cells, and the growth of new tumors in the destination sites of said metastasis.

Antimetastatic agents that can be conjugated with the antibodies of the invention include, without limitation, any cytotoxic agent capable of acting as an antimetastatic agent, such as alkylating agents; antimetabolites such as 5-fluorouracil, permetrexed (MTA), raltitrexed (TDX); platinum cytotoxic agents such as cisplatin or oxaliplatin; topoisomerase inhibitors; antimicrotubule agents; anthracyclines; plant alkaloids; GTPase inhibitors; angiogenesis inhibitors; matrix metalloproteinase inhibitors; inhibitors of the cell cycle regulating kinases, such as the cyclin-dependent kinases and cyclin inhibitors: Wnt signaling inhibitors; inhibitors of the E2F transcription factor; histone deacetylase inhibitors; AKT kinase or ATPase inhibitors.

The conjugates of the antibody and other agents can be created using a variety of coupling agents or bifunctional protein linkers. The linker can be a "cleavable linker" which allows the release of the agent in the cell, such as an acid-labile linker, a peptidase-sensitive linker, a dimethyl linker or a linker containing disulphide.

"Antiproliferative agent" is understood as a chemical or biological substance which is capable of preventing or inhibiting the formation or growth of tumors. Antiproliferative agents include but are not limited to (i) antimetabolites such as folic acid antimetabolites (aminopterin, denopterin, methotrexate, edatrexate, trimetrexate, nolatrexed, lometrexol, pemetrexed, raltitrexed, piritrexim, pteropterin, leucovorin, 10-propargyl-5,8-dideazafolate (PDDF, CB3717)), purine analogs (cladribine, clofarabine, fludarabine, mercaptopurine, pentostatin, thioguanine) and pyrimidine analogs (capecitabine, cytarabine or ara-C, decitabine, fluorouracil, 5-fluorouracil, doxifluridine, floxuridine and gemcitabine) (ii) natural products, such as antitumor antibiotics and mitotic inhibitors such *vinca* alkaloids such as vindesine, vincristine, vinblastine, vinorelbine; taxanes such as paclitaxel (Taxol™), docetaxel (Taxotere™); colchicine (NSC 757), thiocolchicine (NSC 361792), colchicine derivatives (e. g., NSC 33410), and allocolchicine (NSC 406042); halichondrin B (NSC 609395); dolastatin 10 (NSC 376128); maytansine (NSC 153858); rhizoxin (NSC 332598); epothilone A, epothilone B; discodermolide; estramustine; nocodazole; (iii) hormones and antagonist thereof, such tamoxifen, toremifene, anastrozole, arzoxifene, lasofoxifene, raloxifene, nafoxidine, fulvestrant, aminoglutethimide, testolactone, atamestane, exemestane, fadrozole, formestane, letrozole, goserelin, leuprorelin or leuprolide, buserelin, histrelin, megestrol and fluoxymesterone; (iv) biological agents, such as viral vectors, interferon alpha and interleukines; (v) platinum based compounds such as carboplatin, cisplatin [cis-diamminedichloroplatinum, (CDDP)], oxaliplatin, iproplatin, nedaplatin, triplatin tetranitrate, tetraplatin, satraplatin (JM216), JM118 [cis ammine dichloro (II)], JM149 [cis ammine dichloro (cyclohexylamine) trans dihydroxo platinum (IV)], JM335 [trans ammine dichloro dihydroxo platinum (IV)], transplatin, ZD0473, cis, trans, cis-Pt(NH3)(C6H11NH2)(OOCC3H7) 2Cl, malanate-1,2-diaminociclohexanoplatin(II), 5-sulphosalycilate-trans-(1,2-diaminociclohexane)platin (II) (SSP), poly-[(trans-1,2-diaminocyclohexane)platin]-carboxyamilose (POLY-PLAT) and 4-hydroxy-sulphonylphenylacetate (trans-1,2-diaminocyclohexane) platinum (II) (SAP) and the like and (vi) DNA-alkylating drugs such as nitrogen mustards, nitrosoureas, ethylenimine derivatives, alkyl sulfonates and triazenes, including, but not limited to, cyclophosphamide (Cytoxan™), busulfan, improsulfan, piposulfan, pipobroman, melphalan (L-sarcolysin), chlorambucil, mechlorethamine or mustine, uramustine or uracil mustard, novembichin, phenesterine, trofosfamide, ifosfamide, carmustine (BCNU), lomustine (CCNU), chlorozotocin, fotemustine, nimustine, ranimustine, semustine (methyl-CCNU), streptozocin, thiotepa, triethylenemelamine, triethylenethiophosphoramine, procarbazine, altretamine, dacarbazine, mitozolomide and temozolomide.

"Anti-inflammatory agent" is understood as a chemical or biological substance which inhibits or reduces inflammation.

Anti-inflammatory agents that can be conjugated with the antibodies of the invention include, without limitation, 5-aminosalicylic acid and medicaments containing it (sulfasalazine, mesalamine, mesalazine, osalazine); acetylsalicic acid; corticosteroids such hydrocortisone, cortisone, triamcinolone, budesonide, prednisone, deflazacort, methotrexate; infliximab or adalimumab.

Thus, in another aspect, the invention relates to conjugates comprising a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 for use in medicine.

In another aspect, the invention relates to the use of a conjugate comprising a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 for the preparation of a medicament for the prevention and/or treatment of cancer and/or a disease associated to an undesired angiogenesis.

In another aspect, the invention relates to the use of a conjugate comprising a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 for the preparation of a medicament for the prevention and/or treatment of a disease associated with inflammation.

In a preferred embodiment of the invention, the tumor/cancer to be prevented or treated with said conjugates of the invention is colorectal cancer, preferably colorectal carcinoma.

In another preferred embodiment of the invention, the tumor/cancer to be prevented or treated with said conjugates of the invention is digestive carcinoma.

In another preferred embodiment of the invention, the tumor/cancer to be prevented or treated with said conjugates of the invention is fibrosarcoma.

In another preferred embodiment of the invention, the tumor/cancer to be prevented or treated with said conjugates of the invention is breast cancer.

In another preferred embodiment of the invention, the tumor/cancer to be prevented or treated with said conjugates of the invention is epidermoid carcinoma.

In another preferred embodiment of the invention, the tumor/cancer to be prevented or treated with said conjugates of the invention is genital carcinoma.

In another aspect, the invention relates to a conjugate comprising a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 for use in the prevention and/or treatment of cancer and/or a disease associated to an undesired angiogenesis In another aspect, the invention relates to a method of treatment or prevention in an individual suffering from cancer and/or a disease associated to an undesired angiogenesis which comprises administering to said subject a conjugate comprising a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7.

In another aspect, the invention relates to a conjugate comprising a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 for use in the prevention and/or treatment of a disease associated with inflammation.

In another aspect the invention relates to a method of treatment or prevention in an individual suffering from a disease associated with inflammation which comprises administering to said subject a conjugate comprising a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7.

"Medicament", in the context of these inventive aspects, is understood as a pharmaceutical composition comprising a conjugate of a monoclonal antibody of the invention or a polypeptide having at least one fragment of the sequence of said monoclonal antibody with a compound useful in the treatment of cancer, a disease associated to an undesired angiogenesis, or a disease associated with inflammation.

The terms "prevention", "treatment", "cancer", "disease associated to an undesired angiogenesis", and "disease associated with inflammation" have been previously defined in the context of the therapeutic uses of the invention.

Diagnostic Method of the Invention

Since the S100A7 protein is secreted into the extracellular medium by the tumor cells, its presence can be detected in various biofluids. S100A7 also has a role in inflammation, since S100A7 can be secreted and was shown to be chemotactic for neutrophils and lymphocytes T CD4+, thereby providing a useful and non-invasive method for the diagnosis of cancer, or diseases associated to an undesired angiogenesis or diseases associated with inflammation.

Therefore, another aspect of the invention is related to a method for diagnosing cancer selected from digestive carcinoma and genital carcinoma or a disease associated to an undesired angiogenesis or a disease associated with inflammation in a subject which comprises:

(a) detecting the levels of the S100A7 protein or of a variant thereof in a biofluid of said subject, and (b) comparing said levels with a reference value wherein increased levels of the S100A7 protein or of a variant thereof with respect to the reference value are indicative of the subject suffering from cancer selected from digestive carcinoma and genital carcinoma or a disease associated to an undesired angiogenesis, or a disease associated to inflammation.

The method for diagnosing cancer selected from digestive carcinoma and genital carcinoma or a disease associated to an undesired angiogenesis or a disease associated with inflammation can be carried out in vivo or in vitro.

In the context of the present invention, "in vitro method for diagnosing cancer" is understood as method which allows showing the existence of a malignant tumor in a subject by means of detecting the presence of the S100A7 protein soluble in a biofluid isolated from the patient. It is also useful for documenting the expression of S100A7 produced by a tumor prior to administering S100A7 selecting drugs to allow a suitable selection of patients and the determination of the optimal dose.

In the context of the present invention, "in vitro method for diagnosing a disease associated to an undesired angiogenesis" is understood as a method which allows showing the existence of a disease associated to all those diseases where pathogenic angiogenesis occur i.e. when said process is harmful or undesirable, whether cancerous or not, in a subject by means of detecting the presence of the S100A7 protein soluble in a biofluid isolated from the patient. It is also useful for documenting the expression of S100A7 produced when an undesired angiogenesis occurs prior to administering S100A7 selecting drugs to allow a suitable selection of patients and the determination of the optimal dose.

In the context of the present invention, "in vitro method associated with inflammation" is understood as a method which allows showing the existence of an inflammatory disease in a subject by means of detecting the presence of the S100A7 protein soluble in a biofluid isolated from the patient. It is also useful for documenting the expression of S100A7 produced when a disease associated with inflammation occurs prior to administering S100A7 selecting drugs to allow a suitable selection of patients and the determination of the optimal dose.

"Subject" in the present invention is understood as any animal classified as mammal and includes but is not limited to domestic and farm animals, primates and humans, for example human beings, non-human primates, cows, horses, pigs, sheep, goats, dogs, cats or rodents. Preferably, the subject is a female or male human being of any race or age. In the context of the present invention, the subject is a subject who potentially suffers from cancer or has been previously diagnosed with cancer. It is also considered in the context of the present invention that the subject is a subject who potentially suffers from a disease associated to an undesired angiogenesis or a disease associated with inflammation or has been previously diagnosed with any of said diseases.

The first step of the method of the invention comprises determining the levels of the S100A7 protein or of a variant thereof in a biofluid of the study subject.

The term "biofluid" in the context of the present invention refers to any biological secretion or fluid, whether physiological or pathological, which is produced in the body of a subject. Such biofluids include, without limitation, blood, plasma, serum, bronchoalveolar washing fluid, urine, nasal secretion, ear secretion, urethral secretion, cerebrospinal fluid, pleural fluid, synovial fluid, peritoneal fluid, ascites fluid, pericardial liquid, amniotic fluid, gastric juice, lymphatic fluid, interstitial fluid, saliva, sputum, liquid deposition, tears, mucus, sweat, milk, semen, vaginal secretions, fluid coming from ulcer, blisters, abscesses and other surface eruptions. Said samples can be obtained by conventional methods, using processes known in the state of art by the person skilled in the art, such as blood extraction, instillation and aspiration of liquid during bronchofibroscopy, cisternal, ventricular or lumbar puncture, pleural puncture or thoracocentesis, joint or synovial percutaneous puncture, abdominal puncture, amniocentesis, expectoration, peritoneal percutaneous puncture, pericardial percutaneous puncture, etc., or by simple harvesting.

In a preferred embodiment, the biofluid is selected from blood, plasma and serum. The blood sample is typically extracted by means of puncturing an artery or vein, normally a vein from the inner part of the elbow or from the back of the hand, the blood sample being collected in a air-tight vial or syringe. A capillary puncture normally on the heel or on the distal phalanxes of fingers can be performed for analysis by means of a micromethod.

Serum can be obtained from the complete blood sample and in the absence of anticoagulant by leaving the sample to settle for 10 minutes so that it coagulates and subsequently centrifuging it at 1,500 rpm for 10 minutes for the purpose of separating the cells (precipitate) from the serum (supernatant). In turn, to obtain the plasma sample the complete blood is contacted with an anticoagulant and is centrifuged at 3,000 rpm for 20 minutes. The precipitate of said centrifugation corresponds to the formed elements, and the supernatant corresponds to the plasma.

The serum or the plasma obtained can be transferred to a storage tube for sample analysis by means of the method of the invention.

The levels of expression of the S100A7 protein can be detected and quantified by means of conventional methods. Said methods include, without limitation, the detection of S100A7 by measuring its affinity to one of its ligands such as RAGE, and the subsequent quantification of the S100A7-ligand complex; or by means of using antibodies with capacity of binding specifically to the S100A7 protein (or fragments thereof which contain the antigenic determinants) and the subsequent quantification of the resulting antigen-antibody complexes, in a preferred embodiment of the invention, the detection is carried out by means of using an antibody that binds specifically to the S100A7 protein or of a fragment thereof with capacity for binding to the antigen.

Antibodies that can be used in these assays are, for example, serum polyclonal antibodies; supernatants of hybridomas or monoclonal antibodies; chimeric antibodies; humanized antibodies; primatized antibodies; human antibodies; bispecific antibodies; and antibody fragments such as Fab, Fab', F(ab')$_2$, scFv, diabodies, triabodies, tetrabodies and nanobodies. All of the above have been previously described in the context of the therapeutic uses of the anti-S100A7 antibodies.

In a particular embodiment, the antibody used in the method of the invention is a monoclonal antibody produced by a hybridoma selected from the group consisting of ECACC 13020701, ECACC 13020702, ECACC 13020703, ECACC 13020704, ECACC 13020705 and ECACC 13020706 or a functional variant of said antibody, as described in the context of the second aspect of the invention.

In addition, the antibodies used in the method of the invention may or may not be labeled with a detectable agent. In a particular embodiment the antibody used is conjugated to a detectable agent.

In the context of the present invention, the terms "detectable agent" and "labeling" are synonyms and they refer to an agent the nature of which allows its detection by means of enzymatic, radioactive or fluorescence methods. The detectable compound can be an enzyme, a radioactively labeled compound or a radioactive isotope, a fluorochrome, a chemiluminescent reagent, an enzymatic substrate or cofactor, an enzymatic inhibitor, a particle, a dye, etc.

The compounds radioactively labeled by means of radioactive isotopes, also called radioisotopes or radionuclides, may include, without limitation, $^3$H, $^{14}$C, $^{15}$N, $^{35}$S, $^{90}$Y, $^{99}$Tc, $^{111}$In, $^{125}$I, $^{131}$I. The fluorescent labels may include, without limitation, rhodamine, phosphorus-lanthanides or FITC. The enzymatic labels may include, without limitation, horseradish peroxidase, β-galactosidase, luciferase or alkaline phosphatase. The preferred labelling include, but are not limited to, fluorescein, a phosphatase such as alkaline phosphatase, biotin, avidin, a peroxidase such as horseradish peroxidase and compounds related to biotin or compounds related to avidin (for example, streptavidin or ImmunoPure® NeutrAvidin available from Pierce, Rockford, Ill.).

There is a wide variety of well-known assays which can be used in the present invention, these assays use primary non-labeled antibodies and secondary labeled antibodies: such techniques include Western-blot or Western transfer, ELISA (Enzyme Linked Immunosorbent Assay), RIA (radioimmunoassay), competitive EIA (competitive enzyme immunoassay), DAS-ELISA (double antibody sandwich ELISA), or techniques based on the use of protein microarrays or biochips which include specific antibodies or assays based on the colloidal precipitation in forms such as reactive strips. Other ways for detecting the S100A7 protein include techniques such as affinity chromatography, ligand binding assays, etc. There are commercial antibodies against the S100A7 protein in the market which can be used in the context of the present invention.

In a particular embodiment, the quantification of the levels of S100A7 is performed by means of Western-blot or ELISA.

In yet a more particular embodiment, the levels of the S100A7 protein or of its variants are determined by Western-blot. Western-blot is based on detecting the previously resolved proteins by means of electrophoresis in gel under denaturing conditions and being immobilized on a membrane, generally nitrocellulose, by means of incubation with an antibody specific for S100A7 and a development system (e.g. chemiluminescent).

In another preferred embodiment, the diagnostic is performed by means of ELISA. Said technique is based on the detection of the S100A7 protein in a sample by means of an anti-S100A7 antibody immobilized on a substrate and the subsequent detection of the S100A7-antibody complex by means of a second antibody. Commercial kits for carrying out the diagnostic such as S100A7 (Circulex S100A7/Psoriasin ELSA kit CY8073)

The term "protein" as used herein refers to a molecular chain of amino acids, joined by covalent or non-covalent bonds. The term further includes all the physiologically relevant post-translational chemical modification forms. Post-translational modifications which fall within the scope of the present invention include, for example, signal peptide cleavage, glycosylation, acetylation, phosphorylation, isoprenylation, proteolysis, myristoylation, protein folding and proteolytic process, etc. Additionally, the proteins can include non-natural amino acids formed by post-translational modifications or by means of introducing non-natural amino acids during translation.

The term "S100A7" has been defined in the context of the first inventive aspect of the invention. For the diagnostic method of the invention, the detected S100A7 is that which corresponds to the species to which the subject from which the biofluid to be analyzed has been extracted belongs.

As mentioned above, variants of said protein can also be used to measure the levels of the S100A7 protein in the method of the invention.

Therefore, variants of the S100A7 protein can be: (i) those in which one or more of the amino acid residues are substituted by a conserved or non-conserved amino acid residue (preferably a conserved amino acid) and such substituted amino acid residue may or may not be encoded by the genetic code, (ii) those in which there are one or more modified amino acid residues, e.g. residues that are modified by the coupling of substituting groups, (iii) those in which the protein is an alternative splicing variant of the S100A7 and/or (iv) fragments of the protein. The fragments include proteins generated through proteolytic process (including proteolysis at multiple sites) of an original sequence. Said variants fall within the scope of the present invention.

Variants according to the present invention include amino acid sequences that are at least 60%, 70%, 80%, 90%, 95% or 96% similar or identical to the original amino acid sequence. As it is known, the "similarity" between two proteins is determined by means of comparing the amino acid sequence of a protein with a sequence of a second protein. The degree of identity between two proteins is determined using computer algorithms and methods that are widely known by the person skilled in the art, preferably using the BLASTP algorithm [BLASTManual, Altschul, S., et. al., NCBI NLM NIH Bethesda, Md. 20894, Altschul, S., et, al., J. Mol. Biol. 215: 403-410 (1990)].

In a particular embodiment, the variant is a variant from mammal, preferably a human variant, more preferably with at least 60%, 70%, 80%, 90%, 95% or 96% similarity or identity with the original amino acid sequence.

The person skilled in the art will appreciate that the method of the invention can be put into practice using both the absolute level and the relative level of expression of the S100A7 protein. Thus, in the present invention, the expression "levels of the S100A7 protein" is used to refer both the absolute levels and the relative levels of said protein.

The expression "absolute levels" refers to the total amount of the protein of interest in a sample. Said value may be given as the concentration of protein expressed in units of mass per unit of volume (e.g. in ng/ml of sample), in the number of protein molecules per unit of volume (e.g. in pmol protein/ml of sample), in the units of mass of S100A7 protein per unit of mass of total protein (pg S100A7/mg total protein) or in the number of S100A7 molecules per unit of mass of total protein (e.g. in pmol S100A7/mg of total protein).

The expression "relative levels" refers to the relationship between the levels of expression of the S100A7 protein object of the study and of a reference protein, i.e., the concentration of S100A7 protein in normalized form with respect to said reference protein is defined.

In order to normalize the values of protein between the different samples, it is possible to compare the levels of S100A7 protein in the samples to be analyzed with the expression of a control protein. "Control protein" in the present invention is understood as a protein the levels of expression of which do not change or only change in limited amounts in the tumor cells with respect to the non-tumor cells. Preferably, the control protein is a protein encoded by genes that are constitutively expressed that are those genes always active or being transcribed constantly, such that these proteins are constitutively expressed and carry out essential cellular functions. Preferred control proteins that can be used in the present invention include, without limitation, β-2-microglobulin (B2M), ubiquitin, 18-S ribosomal protein, cyclophilin, GAPDH, PSMB4, tubulin and actin. In a more preferred embodiment the control protein is tubulin.

The person skilled in the art understands that mutations in the amino acid sequence of the S100A7 protein do not affect the detection of the expression thereof and, therefore, the variants of this protein generated by mutations of the amino acid sequence fall within the scope of the present invention.

Once the level of expression of S100A7 in a sample has been determined, step (b) of the invention which consists of comparing the levels of S100A7 obtained in step (a) with a reference value takes place.

The "reference value" derives from a sample collection formed preferably by a mixture of the biofluid to be analyzed from normal individuals not affected by cancer a disease associated to an undesired angiogenesis or a disease associated with inflammation. Said reference value can be determined by means of techniques well known in the state of the art for example, determining the mean of the levels of S100A7 protein measured in biofluids taken from healthy subjects. The reference value can also be obtained from the constitutively expressed proteins taken from the same subject to be analyzed.

Once the reference value is established, the value of the levels of S100A7 obtained in step (a) can be compared with this reference value and, therefore, allows detecting alterations in the levels of S100A7 protein of the subject with respect to the reference value. More specifically, in the method of the invention, an increase of the levels of S100A7 with respect to the reference value is indicative of the subject suffering from cancer or a disease associated to an undesired angiogenesis or a disease associated with inflammation.

In the context of the present invention, "increased levels" with respect to the reference value is understood as a variation of the levels of S100A7 above the reference value of at least 1.1 times, 1.5 times, 5 times, 10 times, 20 times, 30 times, 40 times, 50 times, 60 times, 70 times, 80 times, 90 times, 100 times or even more times as compared to the reference value.

Therefore, once said comparison has been performed, the method of the invention allows diagnosing if the subject suffers from cancer. In a particular embodiment, the method is suitable for diagnosing digestive carcinoma. In a particular embodiment, the method is suitable for diagnosing colorectal carcinoma. In another particular embodiment, the method is suitable for diagnosing genital carcinoma. In another particular embodiment, the method is suitable for diagnosing epidermoid carcinoma.

In another embodiment, once said comparison has been performed, the method of the invention allows diagnosing if the subject suffers from a disease associated to an undesired angiogenesis.

In another embodiment, once said comparison has been performed, the method of the invention allows diagnosing if the subject suffers from a disease associated with inflammation.

Prognostic Method of the Invention

In another aspect, the invention relates to an in vitro method for determining the prognosis or monitoring the progression of cancer selected from digestive and genital carcinoma or a disease associated to an undesired angiogenesis or a disease associated with inflammation in a subject which comprises:
  a) detecting the levels of the S100A protein or a variant thereof in a biofluid of said subject, and
  b) comparing said levels with a reference value for said protein obtained from the same subject at an earlier time point of the disease,
wherein decreased levels of the S100A7 protein or a variant thereof with respect to the reference value is indicative that the digestive or genital carcinoma or a disease associated to an undesired angiogenesis or a disease associated with inflammation shows a good prognosis or
wherein increased levels of the S100A7 protein or a variant thereof with respect to the reference value is indicative that the digestive or genital carcinoma or a disease associated to an undesired angiogenesis or a disease associated with inflammation shows a bad prognosis.

In a preferred embodiment, the digestive carcinoma is a colorectal carcinoma.

As used in the present invention, the expression "monitoring the progression of cancer", which is equivalent to "determining the prognosis", relates to the determination of one or several parameters indicating the progression of the disease in a patient diagnosed with cancer selected from digestive and genital carcinoma. Parameters suitable for determining the evolution of a subject diagnosed with digestive or genital carcinoma are selected from the group risk of relapse, disease-free survival and/or overall survival of the subject. As used herein, the expression "risk of relapse" is understood as the probability of a subject developing digestive or genital carcinoma and/or a secondary metastasis again after a disease-free period; "disease-free survival" is understood as the time period after the treatment in which the cancer is not found; and "overall survival of the subject" is understood as the percentage of subjects who survive, from the time of the diagnosis or treatment, after a defined time period.

As used in the present invention, the expression "monitoring the progression of a disease associated to an undesired angiogenesis", which is equivalent to "determining the prognosis", relates to the determination of one or several parameters indicating the progression of the disease in a patient diagnosed with a disease associated to an undesired angiogenesis. Parameters suitable for determining the evolution of a subject diagnosed with a disease associated to undesired angiogenesis are selected from the group of risk of relapse, disease-free survival and/or overall survival of the subject. As used herein, the expression "risk of relapse" is understood as the probability of a subject developing a disease associated to an undesired angiogenesis again after a disease-free period; "disease-free survival" is understood as the time period after the treatment in which the disease associated to an undesired angiogenesis is not found; and "overall survival of the subject" is understood as the percentage of subjects who survive, from the time of the diagnosis or treatment, after a defined time period.

As used in the present invention, the expression "monitoring the progression of a disease associated with inflammation", which is equivalent to "determining the prognosis", relates to the determination of one or several parameters indicating the progression of the disease in a patient diagnosed with a disease associated with inflammation. Parameters suitable for determining the evolution of a subject diagnosed with a disease associated with inflammation are selected from the group of risk of relapse, disease-free survival and/or overall survival of the subject. As used herein, the expression "risk of relapse" is understood as the probability of a subject developing a disease associated with inflammation again after a disease-free period; "disease-free survival" is understood as the time period after the treatment in which the disease associated with inflammation is not found; and "overall survival of the subject" is understood as the percentage of subjects who survive, from the time of the diagnosis or treatment, after a defined time period.

According to this inventive aspect, the levels of the S100A7 protein or a variant thereof determined in a biofluid from a subject having cancer selected from digestive and genital carcinoma or a disease associated to an undesired angiogenesis or a or a disease associated with inflammation obtained at a first period of time (first subject sample) and the levels of the S100A7 protein or a variant thereof determined in a biofluid from a subject having cancer selected from digestive and genital carcinoma or a disease associated to an undesired angiogenesis or a disease associated with inflammation obtained at a second period of time (second subject sample) are compared allowing the progression of cancer selected from digestive and genital carcinoma or a disease associated to an undesired angiogenesis or a disease associated with inflammation in said subject having cancer selected from digestive and genital carcinoma or a disease associated to an undesired angiogenesis or a disease associated with inflammation to be monitorized. The second subject sample can be taken from the same subject having cancer selected from digestive and genital carcinoma or a disease associated to an undesired angiogenesis or a disease associated with inflammation from which the first measure is derived, at a second period of time, i.e., at any time after the first period of time, e.g., one day, one week, one month, two months, three months, 1 year, 2 years, or more after the first subject sample. In a particular embodiment, the first subject sample is taken prior to the subject receiving treatment, e.g. chemotherapy, radiation therapy, or surgery, and the second subject sample is taken after treatment. In another particular embodiment, the first subject sample is taken after the subject has started/received treatment, e.g. chemotherapy, radiation therapy, or surgery, and the second subject sample is taken later, at different time periods during a course of treatment. These methods allow for the evaluation of the progression of the cancer selected from digestive and genital carcinoma or a disease associated to an undesired angiogenesis or a disease associated with inflammation in a selected subject previously diagnosed as suffering from any of said diseases. Consequently, if the cancer selected from digestive and genital carcinoma or the disease associated to an undesired angiogenesis or the disease associated with inflammation has a bad prognosis, a further therapy should be designed to treat said disease in said subject. The progression of the cancer selected from digestive and genital carcinoma or the disease associated to an undesired angiogenesis or the disease associated with inflammation after said new treatment can be easily followed according to the teachings of this invention.

As mentioned previously concerning the diagnostic method of the invention, the the levels of the S100A7 protein or a variant thereof can be determined by any suitable means known in the art, such as, for example, western blot or ELISA.

Once the expression levels of the protein S100A7 or a variant thereof in the subject samples, at different periods of time (first and second subject samples) have been determined, it is necessary to identify if there is a significant increase in the expression of said protein in the second subject sample in comparison with the expression level of said protein in the first subject sample. Alternatively, if desired, one may analyze if there is a significant decrease in the expression of said protein in the second subject sample in comparison with the expression level of said protein in the first subject sample. The terms "increased levels" and "decreased levels" applied to the expression level of S100A7 protein or a variant thereof have been previously defined.

Thus, a significant increase levels of the protein S100A7 or a variant thereof in the second subject sample with respect to the expression level of said protein in the first subject sample is indicative that cancer selected from digestive and genital carcinoma or a disease associated to an undesired angiogenesis or a disease associated with inflammation in the subject under study is in progression (i.e., it has a bad prognosis); thus, the therapy administered to the subject under study should be changed and a new therapy should be designed to treat cancer selected from digestive and genital carcinoma or a disease associated to an undesired angiogenesis or a disease associated with inflammation in said subject. The progression of the cancer selected from digestive and genital carcinoma or a disease associated to an undesired angiogenesis or a disease associated with inflammation in the subject can be easily followed according to this method.

On the contrary, if no significant increase levels of the protein S100A7 or a variant thereof of protein in the second subject sample with respect to the expression level of said protein in the first subject sample is achieved, or even, if a significant decrease in the level of expression the protein S100A7 or a variant thereof in the second subject sample with respect to the expression level said protein in the first subject sample is achieved, then cancer selected from digestive and genital carcinoma or a disease associated to an undesired angiogenesis or a disease associated with inflammation in the subject under study is not in progression (i.e., it does not have a bad prognosis).

The term "subject", "sample", "biofluid", "disease associated to an undesired angiogenesis", "disease associated with inflammation" and their preferred embodiment, "digestive carcinoma", "colorectal carcinoma" and "genital carcinoma", have been previously defined in the context of the diagnostic method of the invention and equally apply to this inventive aspect of the present invention.

Kits of the Invention and Uses Thereof

In another aspect, the invention relates to a kit for diagnosing cancer or a disease associated to an undesired angiogenesis or a disease associated with inflammation in a sample which comprises at least one antibody according to the second aspect of the invention, i.e., one specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7. In a particular embodiment, the cancer is a cancer selected from digestive carcinoma and genital carcinoma. In a more preferred embodiment the digestive carcinoma is colorectal carcinoma.

In another aspect, the invention relates to the use of a kit as previously defined for diagnosing cancer in a sample of a subject. In a particular embodiment, the cancer is a cancer selected from digestive carcinoma and genital carcinoma. In a more preferred embodiment is colorectal carcinoma.

In another aspect, the invention relates to the use of a kit as previously defined for diagnosing a disease associated to an undesired angiogenesis in a sample of a subject.

In another aspect, the invention relates to the use of a kit as previously defined for diagnosing a disease associated with inflammation in a sample of a subject.

The term "kit", as used in the present document, refers to a combination of a set of reagents suitable for detecting the levels of S100A7 together with one or more types of elements or components (for example, other types of biochemical reagents, containers, packaging suitable for its commercial sale, substrates to which the reagents are bound, electronic hardware components, etc.).

In the present invention, "reagent suitable for detecting the levels of S100A7" is understood as a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 and, optionally, reagents for detecting one or more constitutive proteins.

As it will be understood by the person skilled in the art, the antibodies of the kit of the invention can be used in all the techniques for determining the levels of protein known to be suitable for the analysis of a biofluid, such as Western-blot or Western transfer, ELISA, RIA, competitive EIA, DAS-ELISA, immunocytochemical or immunohistochemical techniques, techniques based on the use of biochips, protein microarrays, assays of colloidal precipitation in reactive strips, etc.

The antibodies can be fixed to a solid support such as a membrane, a plastic or a glass, optionally treated to facilitate the fixation of said antibodies to the support. Said solid support comprises, at least, a set of antibodies which specifically recognize the S100A7 protein, and which can be used for detecting the levels of expression of said protein.

The kits of the invention additionally comprise reagents for detecting a protein encoded by a constitutive gene. The availability of said additional reagents allows normalizing the measurements performed in different samples (for example, the sample to be analyzed and the control sample) to rule out that the differences in the expression of the biomarkers are due to a different quantity of total protein amount in the sample more than the real differences in the relative levels of expression. The constitutive genes in the present invention are genes that are always active or being transcribed constantly and which encode for proteins that are expressed constitutively and carry out essential cellular functions. Proteins that are expressed constitutively and can be used in the present invention include, without limitation, β-2-microglobulin (B2M), ubiquitin, 18-S ribosomal protein, cyclophilin, GAPDH, PSMB4, tubulin and actin.

All the particular embodiments of the method of the present invention are applicable to the kits of the invention and to their uses.

Other Aspects of the Monoclonal Antibodies of the Invention

The monoclonal antibodies of the second aspect of the invention produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 can also be useful for detecting S100A7 in biological samples of another type different from a biofluid. Said detection processes are advantageously applied for the diagnosis and/or prognosis of cancer the tumor cells of which are cells which express the S100A7 protein These monoclonal antibodies can be used for identifying cells and tissues which express the S100A7 protein by means of standard techniques such as immunofluorescence, flow cytometry, affinity chromatography, immunocytochemical or immunohistochemical techniques or immunoprecipitation. For example, a monoclonal antibody of the invention can facilitate the identification of a tumor cell which expresses an S100A7 protein and allows diagnosing cancer in a subject.

Thus, in another aspect, the invention relates to an in vitro method for diagnosing cancer or a disease associated to an undesired angiogenesis or a disease associated with inflammation in a subject which comprises:

(a) detecting the levels of the S100A7 protein or of a variant thereof in a cell or tissue of said subject by means of a specific anti-S100A7 monoclonal antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7.

(b) comparing said levels with a reference value wherein increased levels of the S100A7 protein or of a variant thereof with respect to the reference value are indicative of the subject suffering from cancer or a disease associated to an undesired angiogenesis or a disease associated with inflammation. The term "in vitro method" implies that said method is carried out in a biological sample isolated from the subject from whom it is taken. Said biological sample can be a cell, such as a blood cell, an epithelial cell, a germ cell, etc. or also a biopsy sample of a tissue.

In a preferred embodiment, the diagnostic is performed by means of immunohistochemical techniques. Said techniques are based on the detection of the S100A7 protein in a cell or tissue by means of detection of an anti-S100A7 antibody conjugated to an enzyme, such peroxidase that can catalyse a color-producing reaction. Alternatively, the antibody can also be tagged to a fluorophore, such as fluorescein or rhodamine among others well known in the art.

The terms "levels of the S100A7 protein", "variant", "reference value" and "increased levels" have already been defined in the context of the method of the invention.

The detection can be facilitated by means of the coupling (i.e., physical binding) of the antibody to a labelling group.

Given that the monoclonal antibodies of the invention recognize the S100A7 protein, they can be used for purifying said protein from a sample.

Preferably, for use in the purification of S100A7, the monoclonal antibodies of the second aspect of the invention are used by associating them with a support or substrate. In principle, any type of support can be used in the methods of the invention, although the use of polymeric type supports such as Sephadex, dextran, polyamino acids soluble in water, polyethylene glycol (PEG), polyglutamic acid (PGA), polylactic acid (PLA), polylactic-co-glycolic acid (PLGA), poly(D,L-lactide-co-glycolide) (PLA/PLGA), poly(hydroxyalkylmethacrylamide), a polyglycerol, a polyamidoamine (PAMAM) and a polyethyleneimine (PEI) is preferable.

Typically, the purification of S100A7 using the monoclonal antibodies of the second aspect of the invention is carried out by means of a process which comprises the steps of:

(i) contacting the sample from which the S100A7 protein is to be purified with an antibody produced by a hybridoma selected from the group of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7 immobilized on a support in conditions suitable for the binding between the antibody and the S100A7 protein to take place;

(ii) washing the complexes formed in step (i) to remove all those compounds from the sample that are nonspecifically bound to the support-antibody conjugate and (iii) eluting the S100A7 protein that is bound to the compound.

The method for purifying the S100A7 protein of the invention can be carried out using any known protein purification method by means of affinity, including, for example, affinity chromatography columns the stationary phase of which is formed by the monoclonal antibodies according to the second aspect of the invention conjugated to a solid support.

The invention is described below by means of the following examples which must be considered as merely illustrative and in no case limiting to the scope of the present invention.

EXAMPLES

Example 1: Cell Culture Aid Cell Lines

Human colon adenocarcinoma HCT-116 (ATCC, No.: CCL-247), human fibrosarcoma HT1080 (ECACC, No.: 85111505), human breast adenocarcinoma MDA-MB-231 (ECACC, No.: 92020424) and human genital carcinoma A431 (ECACC, No.: 85090304) cell lines were cultured in DMEM High-glucose (PAA) supplemented with 10% FCS (Invitrogen) plus 2 mM L-glutamine. Human breast adenocarcinoma cells MDA-MB-468 (ATCC, No.: HTB-132) and human monocytic cells THP-1 (ATCC, No.: TIB-202) were cultured in RPMI 1640 (PAA) supplemented with 10% FCS (Invitrogen) plus 2 mM L-glutamine. Human Umbilical Vein Endothelial Cells, HUVEC, (Lonza) were cultured in EBM-2 media (Lonza) supplemented with growth factors and FCS as provided in the EGM-2 bullekit (Lonza).

Mouse myeloma cells were cultured in RPMI 1640 (PAA) supplemented with 10% FCS (PAA; Australian origin) plus 2 mM GlutaMAX™-I (Invitrogen).

All cells were cultured at 37° C. in a humidified 5% $CO_2$-atmosphere, and were consistently free of *mycoplasma* as evaluated by EZ-PCR *mycoplasma* test kit (Biological Industries).

Example 2: Preparation of the Human Recombinant S100A7 Protein

A fragment encoding the full-length human S100A7 was obtained by RT-PCR from mRNA of the breast adenocarcinoma cell line MDA-MB-468, derived from human breast adenocarcinoma. Specific primers used in the PCR were:
SEQ ID NO: 2 5'-ACTCACATATGAGCAACACT-CAAGCTGAGAGGTCCATAATAG-3' and
SEQ ID NO: 3 5'-ACTCATGAGCTCATCCTGGCTGC-CCCCGGAACAGGGCGCTGC-3'

S100A7 cDNA was cloned into the NdeI site of bacterial expression vector pET28a(+) (Novagen) and positive clones were selected and confirmed by DNA sequencing. This construct was transformed into *E. coli* Tuner™ (DE3) Competent Cells (Novagen), and the protein was induced with 1 mM isopropyl-D-thiogalacto-pyranoside (IPTG; Sigma) for 6 h. Then, bacteria were harvested and lysed by sonication in buffer A (10 μg/mL lisozim, 0.5M NaCl, 10 mM $Na_2HPO_4.2H_2O$, 10 mM $NaH_2PO_4.2H_2O$ and 10 mM imidazole pH 7.5). The lysate was cleared by centrifugation and filtered through a HiTrap™ Chelating affinity column (Amersham). The protein was eluted with buffer B (0.5M NaCl, 10 mM $Na_2HPO_4.2H_2O$, 10 mM $NaH_2PO_4.2H_2O$ and 300 mM imidazole pH 7.5). In some experiments the histidine tag was cleaved using Thrombin protease (Novagen, recognition sequence is Leu-Val-Pro-Arg-Gly-Ser (SEQ ID NO: 4), cleavage site between Arg and Gly). Therefore, the final full-length recombinant S100A7 protein has an additional Gly-Ser-His at the N-terminus. Following digestion the remaining poly-his chain was removed by HiTrap™ Chelating affinity column (Amersham) using the poly-histidine sequence tag and the purity of the supernatant containing the recombinant S100A7 protein was checked by SDS-12% (w/v) polyacrylamide gel electrophoresis.

Example 3: Obtaining the Anti-S100A7 Monoclonal Antibodies

Monoclonal antibody (mAb) fusion, ELISA screening and subcloning were performed using standard technologies. Maintenance, expansion and scale up of cultures were done in a humidified atmosphere (94% air and 6% CO2) at 37° C.

For each monoclonal antibody, four animals were immunized with human recombinant S100A7 according to the following protocol. Fifty micrograms of S100A7 protein diluted in PBS (137 mM NaCl, 2.8 mM KCl, 8.1 mM $Na_2HPO_4$, 1.5 mM $KH_2PO_4$; pH 7.2) was used as an emulsion with Complete Freund's adjuvant (Sigma) for the initial subcutaneous (s.c.) immunization and with Incomplete Freund's adjuvant (Sigma) for subsequent injections at days 13 and 28 (s.c.). Ten days after the third injection, sera were obtained and tested. At day-51 a final boost of 25 μg of S100A7 protein diluted in PBS was given intravenously to the mouse with the highest titer serum.

Fusion was done four days after the last injection. mAbs obtained were derived from one fusion of myeloma cells with spleen cells from the selected mouse at a ratio ⅒ respectively using PEG-1500 (Roche Diagnostics) as fusion inducer. After then, cells were plated in 96 microwell plates in medium containing HAT (Invitrogen) for selection of hybrids.

Hybridoma supernatants were screened for reactivity with recombinant human S100A7 by ELISA. 50 μl of S100A7 protein (3 μg/mL in PBS) was coated on MaxiSorp 96 microwell plates (NUNC) overnight at 4° C. After washing with PBS and blocking (1% skimmed milk in PBS; 1 h; 37° C.), 50 μl of hybridoma supernatants were added to each well and incubated for 2 h at 37° C. After washing, at room temperature, five times with calcium-magnesium free PBS-HT (274 mM NaCl, 2.8 mM KCl, 8.1 mM $Na_2HPO_4$, 1.5 mM $KH_2PO_4$, 0.1% Tween-20; pH 7.2), bound immunoglobulins were detected with HRP-conjugated goat anti-mouse IgG/IgM (Jackson ImmunoResearch) using Tetramethylbenzidine 3,3 5,5 (TBM, Sigma) as substrate.

Wells with an optical density greater than three times the plate background were chosen for cloning. Clones corresponding to monoclonal antibody 2D9 (internal code 2D9-1C4-3D7-5E6; ECACC 13020701), 2H3 (Internal code 2H3-1A12-5E12-1A4; ECACC 13020702), 6E3 (Internal code 6E3-2D5-1F9-5B4; ECACC 13020703), 6F5 (Internal code 6F5-2F8-2G9-1A2; ECACC 13020704), 8B6 (Internal code 8B6-1A9-5A8-8G2; ECACC 13020705) and 9F3 (Internal code 9F3-3E6-2D7-3B3; ECACC 13020706) were selected for in vitro and in vivo analysis and subcloned by limiting dilution. Only those subclones that grew at 0.1 and 0.01 cell per well were considered suitable for expansion and were adapted to DMEM/F12 medium (PAA) and frozen.

For large scale purification, hybridoma cells were cultured in DMEM/F12 containing 10% of Fetal Bovine Serum (PAA, Australian origin) and 2 mM of L-Glutamine (GlutaMAX™-I, Invitrogen) in 175 $cm^2$ culture flask. When cell concentration reached $0.8 \times 10^6$ cells/mL (viability over 85%) the culture medium was removed and the cells were washed twice with DMEM/F12 medium without serum. After then, 50 ml of a medium containing 80% DMEM/F12, 20% CDHybridoma (Invitrogen) and 2 mM of L-Glutamine was added to each flask and incubated for 96 h. At the end, serum-free medium was collected, centrifuged and frozen until purification.

Six liters of serum free supernatant from the hybridoma was obtained. After filtration, purification was made using a 5 ml HiTrap Protein G HP affinity column (Amersham). Eluted antibody was concentrated and diafiltrated in PBS with Amicon® Ultra-15 centrifugal filter devices with low-binding Ultracel® membranes (30000 NMWL, Millipore) Final conditioned antibodies were quantified at 280 nm.

Example 4: Characterizing the Cross-Reactivity of the Anti-S100A7 Monoclonal Antibodies 2D9, 2H3, 6E6, 6F5, 8B6 and 9F3 Monoclonal Antibodies Only React with Human S100A7

Monoclonal antibodies 2D9, 2H3, 6E3, 6F5, 8B6 and 9F3 were screened for cross-reaction against other members of the S100 family: recombinant human S100A4 and S100P (cloned from the HCT-116 human colon adenocarcinoma cell line and from the HeLa human cervix adenocarcinoma cell line, respectively, at Leitat Biomed Division). The immunoglobulin isotype for monoclonal antibodies against S100A7 were determined using the Mouse immunoglobulin subtyping kit (Southern Biotech).

Antibodies screening by ELISA on purified human S100A7, human S100A4 and human S100P revealed that monoclonal antibody 2D9, 2H3, 6E3, 6F5, 8B6 and 9F3 only recognized the human S100A7 (Table 1).

TABLE 1

2D9, 2H3, 6E3, 6F5, 8B6 and 9F3 specificity analyzed by ELISA.

| Antibody | Immunogen | Isotype | Human S100A7 | Human S100A4 | Human S100P |
|---|---|---|---|---|---|
| 2D9 | Human S100A7 | IgG1 | ++++ | – | – |
| 2H3 | Human S100A7 | IgG1 | ++++ | – | – |
| 6E3 | Human S100A7 | IgG1 | ++++ | – | – |
| 6F5 | Human S100A7 | IgG1 | ++++ | – | – |
| 8B6 | Human S100A7 | IgG1 | ++++ | – | – |
| 9F3 | Human S100A7 | IgG1 | ++++ | – | – |

++++ positive reaction,
– no reaction

Example 5: Characterization of the Monoclonal Antibodies by Western-Blot

Cell and tumor samples were rinsed twice with PBS and immediately lysed with ice cold Cell Lysis Buffer (150 mM NaCl, % IGEPAL CA630, 5 mM EDTA, 100 µg/mL PMSF, 1 mM $Na_3VO_4$, 1 mM NaF and 50 mM Tris pH 7.4). Lysates were cleared by centrifugation and the protein concentration was quantified with the Bradford reagent (Bio-Rad). Total extracts (50 µg) were resolved in a 15% SDS-polyacrilamide gel (PAGE) electrophoresis under reduced conditions and transferred to BioTrace™ PVDF membranes (PALL corporation). Membranes were blocked for 1 h in TBS plus 0.1% Tween-20 with 5% skimmed dried milk, incubated overnight with the relevant primary antibody and then with the secondary antibodies for h in blocking buffer, washing three times for 10 min in TBS plus 0.1% Tween-20 after each incubation. Signals were developed using the ECL™ Western Blotting Detection Reagents (Amersham) and exposed to Hyperfilm™ ECL (Amersham).

The concentrations of the antibodies were as follows: monoclonal mouse anti-human S100A7 (Leitat Biomed Division) at 3 µg/mL; polyclonal rabbit anti-tubulin (ICN Biomedicals) at 1:5000 dilution; goat anti-mouse (Jackson ImmunoResearch) at 0.04 µg/ml and goat anti-rabbit (Sigma) at 1:25000 dilution, as secondary antibodies.

FIG. 1 shows the expression pattern of S100A7 protein analyzed by western blot in several tumor cell lines using the monoclonal antibody 9F3 as a primary antibody. Human colorectal carcinoma cell line HT29 (Lane 1), human breast adenocarcinoma cell line MDA-MB-468 (Lane 2), and human breast adenocarcinoma MCF7 cells (Lane 3). Recombinant protein S100A7 was used as a positive control (Lane 4).

Same results obtained with 9F3 could be extensible also for the others monoclonal antibodies of this invention (data not shown).

Example 6: Characterization of 2D9, 2H3, 6E3, 8B6, and 9F3, mAbs by Immunochemistry Immunohistochemical (IHC) staining is widely used in the diagnosis of abnormal cells such as those found in cancerous tumors Detection of S100A7 by IHC in some tumors have been found to correlate with poor prognosis (Tripathi et al. PLoS One. 2010 Aug. 3; 5(8):e11939).

Four micrometer-thick sections from the tumor blocks of human genital carcinoma A431 and human colon adenocarcinoma HT29 were deparaffinised, rehydrated in grade alcohols and processed. Briefly, antigen retrieval was performed in a microwave oven for 15 min in 10 mM sodium citrate pH 6.0 with 0.05% Tween-20. Endogenous peroxidase activity was blocked with a 3% $H_2O_2$ solution in distilled water, and the slides were incubated in 5% normal goat serum for 30 min to prevent nonspecific staining. Then, they were incubated overnight at 4° C. with the appropriately diluted primary antibodies. The following antibodies were used: mouse monoclonal antibody 2D9, 2H3, 6E3, 6F5, 8B6 or 9F3 (2 µg/mL). Thereafter the sections were incubated with the appropriately biotinylated goat anti-mouse IgG (H+L) (Vector Laboratories) at 2 µg/mL for 60 min and ABC complex (Dako) for 30 min at room temperature. NovaRed (Dako) was used as chromogen. Negative control was done using a non-related monoclonal antibody (anti-polyhistidine) instead of the primary antibody.

Figure 2:
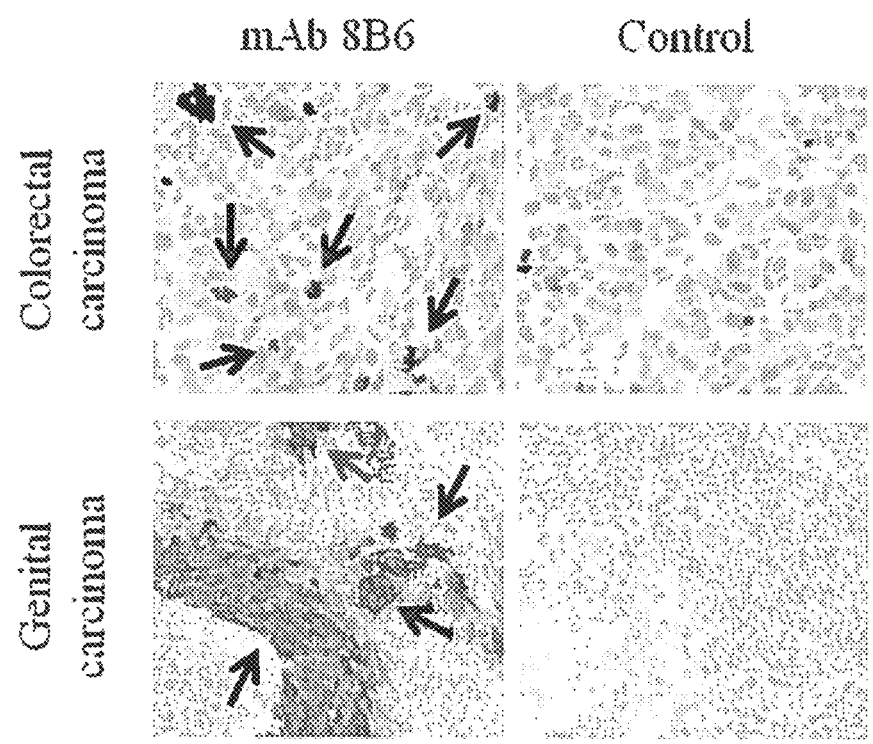
FIG. 2. Immunohistochemical analysis of S100A7 expression in tumors derived from human colorectal carcinoma cell line HT-29, and human genital carcinoma A431 cells. Images were taken at a magnification X200. Staining was done with the indicated anti-S100A7 monoclonal antibody. Arrows indicate S100A7 staining. A non-related mouse monoclonal antibody was used as a negative control (Control).

FIG. 2 shows the immunohistochemical analysis of tumor samples derived from A431 genital carcinoma and human colon adenocarcinoma HT29 model using the anti-S100A7 monoclonal antibody 8B6. S100A7 is highly expressed in the center of the tumor.

Same sensibility and specificity was observed for the other antibodies of the invention (data not shown).

Example 7: Quantification of S100A7 Plasma Levels on Subcutaneous Xenograft A431 Tumor Model There is a need for early detection of tumors and metastasis, critical process for improving treatment in cancer patients. The detection of molecular biomarkers using non-invasive simple tests as blood based quantification methods are one of most clinical needs to detect the presence of a tumor, and monitor cancer therapy.

Plasma levels of S100A7 were quantified by sandwich ELISA method. Briefly, 96 microtiter plates (Maxisorb, NUNC) were coated with 101 g/ml of monoclonal antibody 9F3 diluted in PBS (50 µl/well) 24 h at 4° C. After removing the coating, plates were washed twice with PBS and incubated 2 h at 37° C. in blocking buffer (PBS containing 1% of skimmed milk).

Plasma samples diluted 1:2 in dilution buffer (PBS-1% skimmed milk) were applied to the wells (50 µl/well) and were incubated 2 h at 37° C. Plates were washed six times with washing buffer (PBS-0.1% of Tween-20) and biotinilated 2D9 anti-S100A7 antibody at 10 µg/ml in blocking buffer was applied to the wells (50 µl/well) and incubated for 2 h at room temperature.

Plates were washed six times with washing buffer and goat anti-Mouse-IgG-peroxidase conjugated (Jackson) at the appropriate dilution was added to each well (50 µl/well) and was incubated 1 h at room temperature. After washing six times with washing buffer, the ELISA was revealed adding 50 µl of Tetramethylbenzidine substrate (Sigma) and was incubated for 10 min at RT before stopping with IM of HCl (50 µl/well). Absorbance was read at 450 nm.

Standard curve was obtained by serial dilutions of human recombinant S100A7 in blocking buffer with fetal bovine serum (1:1, v/v).

Figure 3:
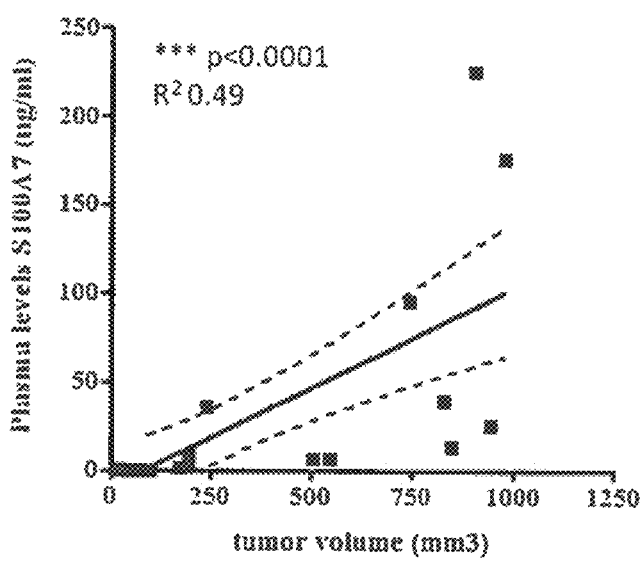
FIG. 3. Determination by ELISA of S100A7 plasma levels on animals bearing tumors derived from human genital carcinoma A431 cell line. (A) Quantification of S100A7 plasma levels compared with the tumor volume for each animal. (B) Comparison between the S100A7 plasma levels of each animal the day before (pre-operatory) and 4 days after the tumor resection (post-operatory). Graph shows mean±s.d. Mann whitney U-test * $p<0.05$ FIG. 4. 2D9 monoclonal antibody blocks ERK phosphorylation induced by S100A7 in both MDA-MB-231 and MDA-MB-468 breast adenocarcinoma cell lines. Images show the immunodetection of phosphorylated ERK (Ph-ERK), total ERK and actin protein analized by western blot. Graphs show the quantification of the relative amount of phospho-ERK compared with the control (non-stimulated cells).
Figure 3:
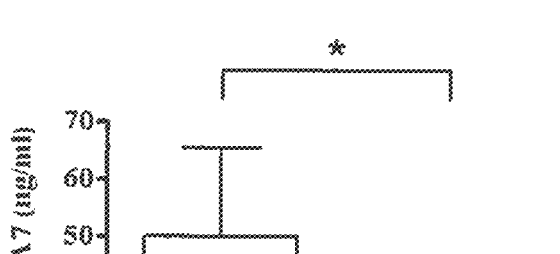

FIG. 3 shows the plasma levels quantification of S100A7 in animals bearing subcutaneous tumor (mean of tumor volumes between 50 and 1000 $mm^3$ approximately) of A431 cell line. Plasmas of animals without tumor were also analysed. FIG. 3A shows a correlation between the tumor volume and the levels of S100A7, being higher in the biggest tumors. In animals without tumor S100A7 was no detected (FIG. 3B).

FIG. 3B shows the S100A7 plasma levels from animals without tumor, animals bearing tumors between 800 and 1000 mm$^3$ and from animals 4 days after tumor resection. Plasma levels were analyzed by ELISA.

Taken together all these results, we confirm that tested monoclonal antibodies can be used as a tool in diagnostic, prognostic and disease monitorization analyses.

Example 8: S100A7 Induces ERK Phosphorylation and the Anti-S100A7 Monoclonal Antibodies Block this Activity It was determined whether S100A7 is an activator of MAPK pathway in breast adenocarcinoma cells and whether the monoclonal antibodies according to the present invention can block this activity.

Human breast adenocarcinoma cells, MDA-MB-231, were seeded in 24 well plates at a density of 150.000 cells/well and grown during 24 h. Then, 3 µM of S100A7 was added to the culture. For blocking assays, S100A7 was preincubated with monoclonal antibodies (3 µM) 4 h prior to the addition to the cells. After 60 min of stimulation, cells were washed with PBS and then were lysed with ice cold Cell Lysis Buffer (150 mM NaCl, 1% IGEPAL CA630, 5 mM EDTA, 100 µg/mL PMSF, 1 mM Na3VO4, 1 mM NaF and 50 mM Tris-HCL, pH 7.4). Lysates were cleared by centrifugation. Total extracts for all analyses were resolved by 15% SDS polyacrilamide gel (PAGE) electrophoresis under reducing conditions and transferred to BioTrace™ PVDF membranes (PALL corporation). Membranes were blocked for 1 h in TBS plus 0.1% Tween-20 and 5% skimmed dried milk, incubated overnight with the primary antibody and then with the secondary antibodies for 1 h in blocking buffer, with three washes of 10 min each in TBS plus 0.1% Tween-20 after each incubation. Signals were developed using the ECL™ Western Blotting Detection Reagents (Amersham) and exposed to Hyperfilm™ ECL (Amersham). The antibodies used for western blot were: monoclonal anti-β-actin peroxidase conjugated (sigma), 1:50000 dilution; mouse monoclonal anti-human phospho-p44/42 MAP kinase (Thr202/Tyr204) (Cell Signaling Technology), 1:2000 dilution; rabbit polyclonal anti-p44/p42 MAP kinase (Cell Signaling Technology), 1:1000 dilution. Goat anti-mouse (Jackson ImmunoResearch) at 0.04 µg/mL and goat anti-rabbit (Sigma) at a 1:25000 dilution, were used as secondary antibodies.

Figure 4:
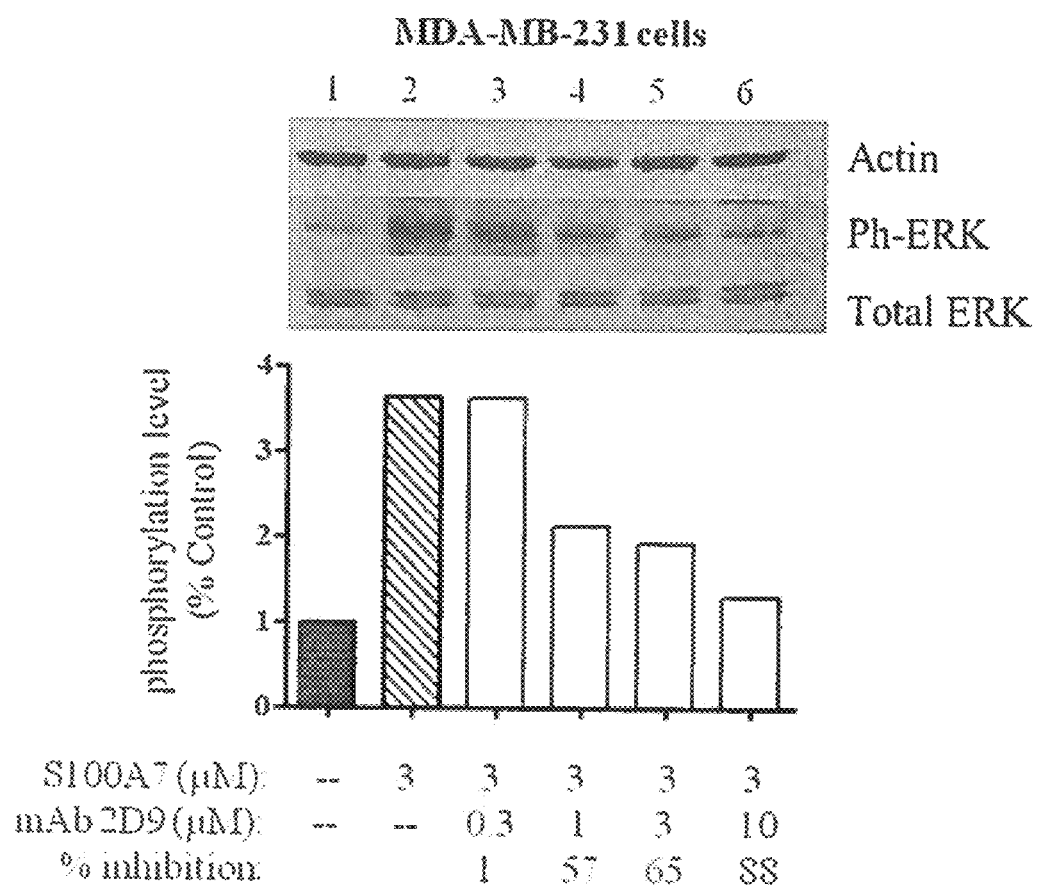
Figure 4:
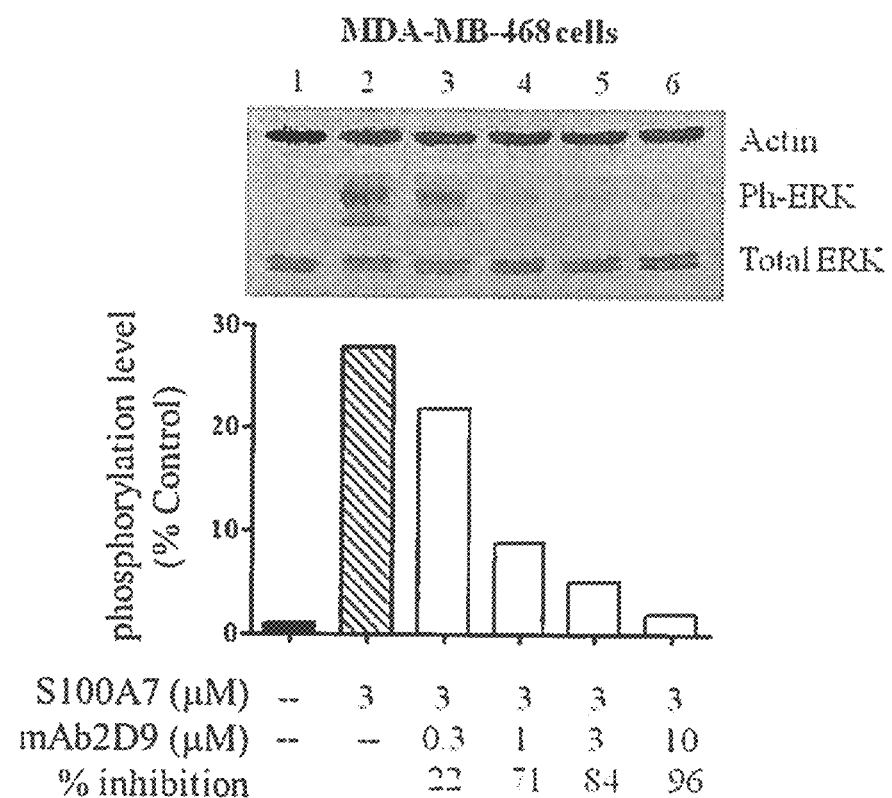

FIG. 4 shows the immunodetection of actin, ph-ERK and ERK proteins in both MDA-MB-231 and MDA-MB-468 cell lines after stimulation with S100A7 alone or with the combination of increased concentrations of 2D9 monoclonal antibody. Graphs show the quantification of the phosphorylation levels using the ImageJ (NIH) analysis software.

Results show the ratio value of: (ph-ERK/actin)/(ERK/actin), for each lane, considering the value for the non-stimulated cells (lane 1) as 1. The percentage of inhibition for lanes 3-6 was calculated considering the value of the stimulated cells (lane 2) as 100% of stimulation.

S100A7 induced ERK phosphorylation after 60 minutes in both MDA-MB-231 and MDA-MB-468 breast adenocarcinoma cell lines. The monoclonal antibody 2D9 was capable to block this activity in a dose-dependent manner. This results are extensible for the others monoclonal antibodies of the present invention (data not shown).

Based on these results, the inventors have showed that S100A7 induces a response in tumor cells through the activation of several signalling pathways, including ERK, and that this effect is blocked by the monoclonal antibodies against the S100A7 protein.

Example 9: S100A7 Induces the Secretion of TNFalpha and the Anti-S100A7 Monoclonal Antibodies Block this Activity It was then determined whether extracellular S100A7 can induce the secretion of TNFalpha to the tumor microenvironment by a tumor cell line and whether this activity could be blocked by the antibodies according to the invention.

Human breast adenocarcinoma cells, MDA-MB-231, were seeded in 24 well plates at a density of 150.000 cells/well and grown during 24 h. Then, cells were washed twice with serum free medium and were stimulated with 3 µM of S100A7. For neutralizing assays S100A7 was preincubated with monoclonal antibodies (3 µM) for 4 h prior to the addition to the cells. After 72 hours of stimulation, supernatants were collected and cleared by centrifugation. The same amount of supernatant of each condition (35 µl) was resolved by 15% SDS-polyacrilamide gel (PAGE) electrophoresis under reducing conditions and transferred to BioTrace™ PVDF membranes (PALL corporation). Membranes were blocked for 1 h in TBS plus 0.1% Tween-20 and 5% skimmed dried milk, incubated overnight with the primary antibody and then with the secondary antibodies for 1 h in blocking buffer, with three washes of 10 min each in TBS plus 0.1% Tween-20 after each incubation. Signals were developed using the ECL™ Western Blotting Detection Reagents (Amersham) and exposed to Hyperfilm™ ECL (Amersham). The antibodies used for western blot were: rabbit polyclonal anti-TNFalpha (Sigma) 1:1000 dilution; goat anti-rabbit (Sigma) peroxidase conjugated at a 1:25000 dilution.

Figures 5, 6:
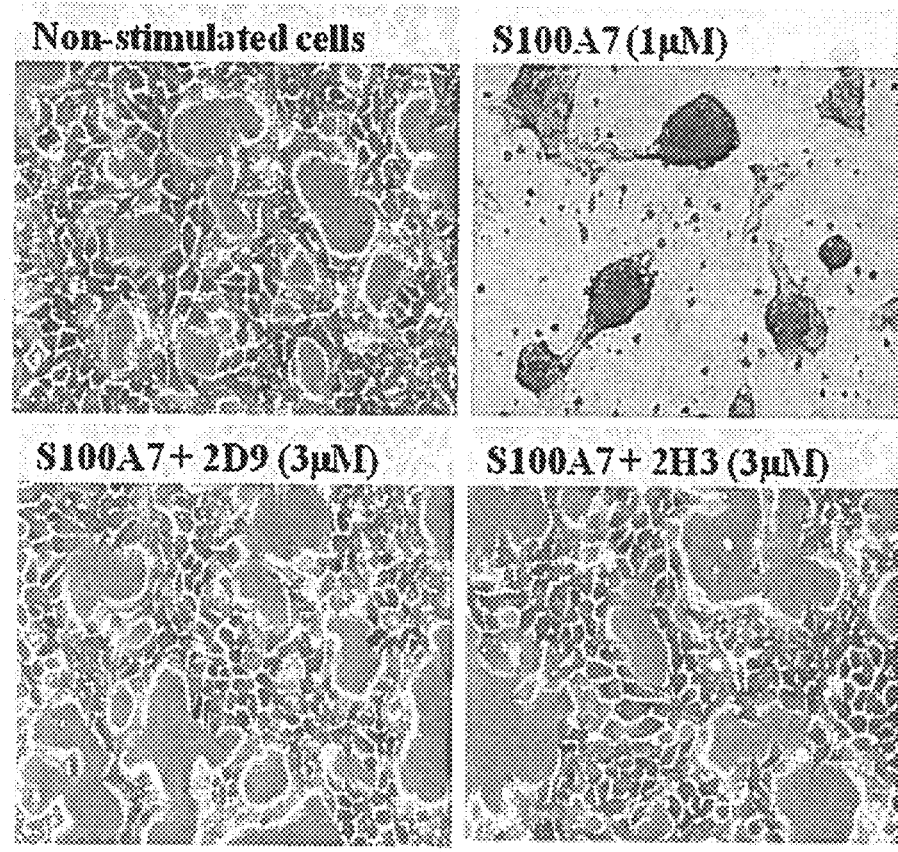
FIG. 5. 2D9 and 2H3 monoclonal antibodies block the secretion of TNFalpha induced by S100A7 in MDA-MB-231 breast adenocarcinoma cell line. Image shows immunodetection by western blot of TNFalpha protein present in supernatant of MDA-MB-231 cells after 72 h of stimulation.
FIG. 6. Inhibitory effect of monoclonal antibodies 2D9 and 2H3 on the formation of stem cell-like tumorspheres induced by S100A7 in human colon carcinoma HCT116 cell line. Cells were plated onto adherent 24-well plates and exposed to S100A7 with or without antibodies. A representative photograph was taken for each culture condition after 96 hours of incubation.

FIG. 5 shows the immunodetection of TNFalpha protein present in the supernatant of MDA-MB-231 cells after 72 h of stimulation with S100A7. Neutralizing effect of 2D9 or 2H3 monoclonal antibodies was analyzed.

Extracellular S100A7 induced the secretion of TNFalpha in breast adenocarcinoma cells MDA-MB-231, and monoclonal antibodies 2D9 and 2H3 were capable to block this activity. This results are extensible for the others monoclonal antibodies of the present invention (data not shown).

Taking into account these results, we can speculate that extracellular S100A7 present in tumor microenvironment could act as a modulator of different cell types inducing the activation of signalling pathways, as MAPK pathway, as previously showed, and the expression and secretion of other factors, such as TNFalpha, which can also act as inflammatory and tumor promoters. Monoclonal antibodies of the present invention are able to block the mechanism of action induced by soluble S001A7, and therefore they can block the inflammatory response induced by the protein.

Example 10: S100A7 Induces the Formation of HCT116 Tumor Spheres and the Anti-S100A7 Monoclonal Antibodies Block this Activity The capacity of colon adenocarcinoma cells HCT-116 to form tumorspheres have been described previously (Kai K et al. Cancer Sci. 2009 December; 100: 2275-82).

HCT-116 cells were cultured in adherent 12-well plates with 3% FCS DMEM medium at a density of 200,000 cells/well in the presence of extracellular S100A7 (1 µM) for 120 h. For blocking, S100A7 was incubated with monoclonal antibodies (3 µM) for 4 h prior to the addition to the cells. After stimulation, a representative picture of each condition was taken. The amount of spheres formed in each culture condition was analyzed visually. The assay was repeated for more than 3 times with the same results.

FIG. 6 shows representative pictures of HCT-116 cell line exposed to each culture condition. Cells exposed to extracellular S100A7 acquired a tumor spheres-like morphology after 120 h of stimulation. All the monoclonal antibodies of the present invention were able to block this activity, as shown in FIG. 6 with 2D9 and 2H3 monoclonal antibodies.

Here, we have described for the first time that S100A7 factor is able to induce this stem-like phenotype and that the monoclonal antibodies according to the invention can block this effect.

Example 11: S100A7 Induces the Proliferation of HT1080 Tumor Cells and the Anti-S100A7 Monoclonal Antibodies Block this Activity It was next determined whether S100A7 could induce the proliferation of HT1080 tumor cells and whether the anti-S100A7 monoclonal antibodies could block this activity.

Fibrosarcoma cells, HT1080, were seeded onto 96-well plates at a density of 2.000 cells/well and were stimulated with S100A7 (500 nM) for 72 h. For blocking assays S100A7 was preincubated with monoclonal antibodies (1.5 µM) for 2 h prior to the addition to the cells. After 72 h of stimulation, viability was measured by a colorimetric method based on salt tetrazolium MTT (Calbiochem) according to the manufacturer's instructions. The percentage of cell viability was calculated using the following formula: (mean absorbance of treated cells−mean absorbance of negative control cells)/(mean absorbance of untreated cells−mean absorbance of negative control cells).

Figure 7:
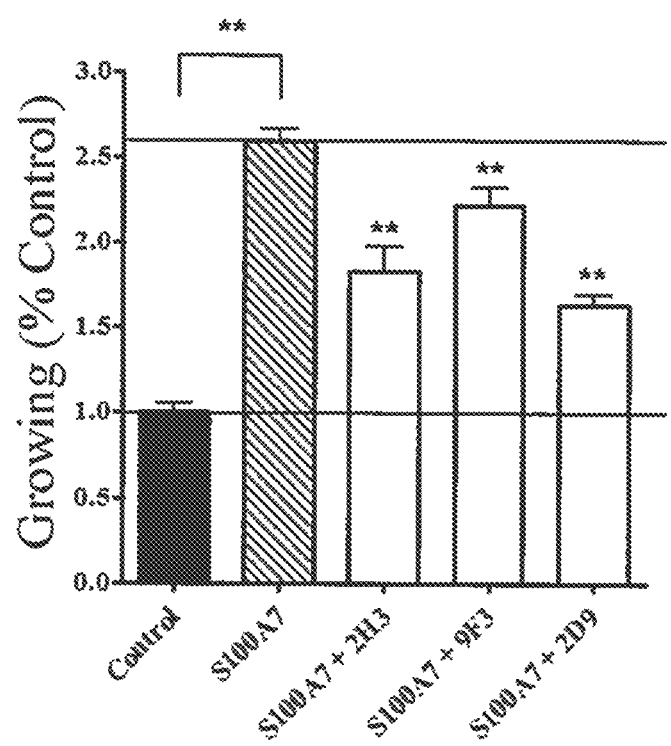
FIG. 7. Monoclonal antibodies 2D9, 2H3 and 9F3 block tumor cell proliferation induced by S100A7 in fibrosarcoma cell line HT1080. Cells were exposed to S100A7 with or without antibodies and viability was assessed after 72 h of stimulation by MTT assay. Bars show mean±s-d. ** $p<0.01$ ("Mann-Whitney U test").

FIG. 7 shows the viability after 3 independent experiments. Extracellular S100A7 induce a 2.6-fold increase of cell proliferation with respect to non-stimulated cells. Antibodies showed a statistically significant neutralizing activity of the S100A7 stimulation: mAb 2D9 (66%), mAb 9F3 (35%) and mAb 213 (63%), respectively.

Taking into account these results, we can conclude that S100A7 can be an inducer of cell proliferation, which is related with the in vivo tumor growth, and the monoclonal antibodies of the present invention can block this activity.

Example 12: S100A7 Increases the Migration of MDA-MB-231 and A431 Tumor Cells and the Anti-S100A7 Monoclonal Antibodies Block this Activity Tumor cell migration is necessary at the initiation of the metastatic cascade, at which time the tumor cells leave the primary location and gain access to the circulation.

Breast adenocarcinoma cell line MDA-MB-231 and A431 were cultured onto 24-well cell culture plates (50.000 cells/well each) with light opaque PET membrane filter inserts with 8 µm-pores (prepared according to the manufacturer). Cells may actively migrate from the upper to the lower compartment.

Medium with soluble S100A7 protein (3 µM) alone or in combination with the antibodies 2D9, 2H3, 6E3, 6F5, 8B6 or 9F3 (9 µM) were added to each well and were cultured for 24 hours. After 24 hours cells were incubated with 5 µM Calcein-AM (Calbiochem) for 15 minutes at 37° C. Fluorescence was measured using a multi-well scanning fluorometer. Comparisons between groups were made using the two-tailed nonparametric Mann Whitney U test. Differences for which P value was less than 0.05 were considered statistically significant.

Figure 8:
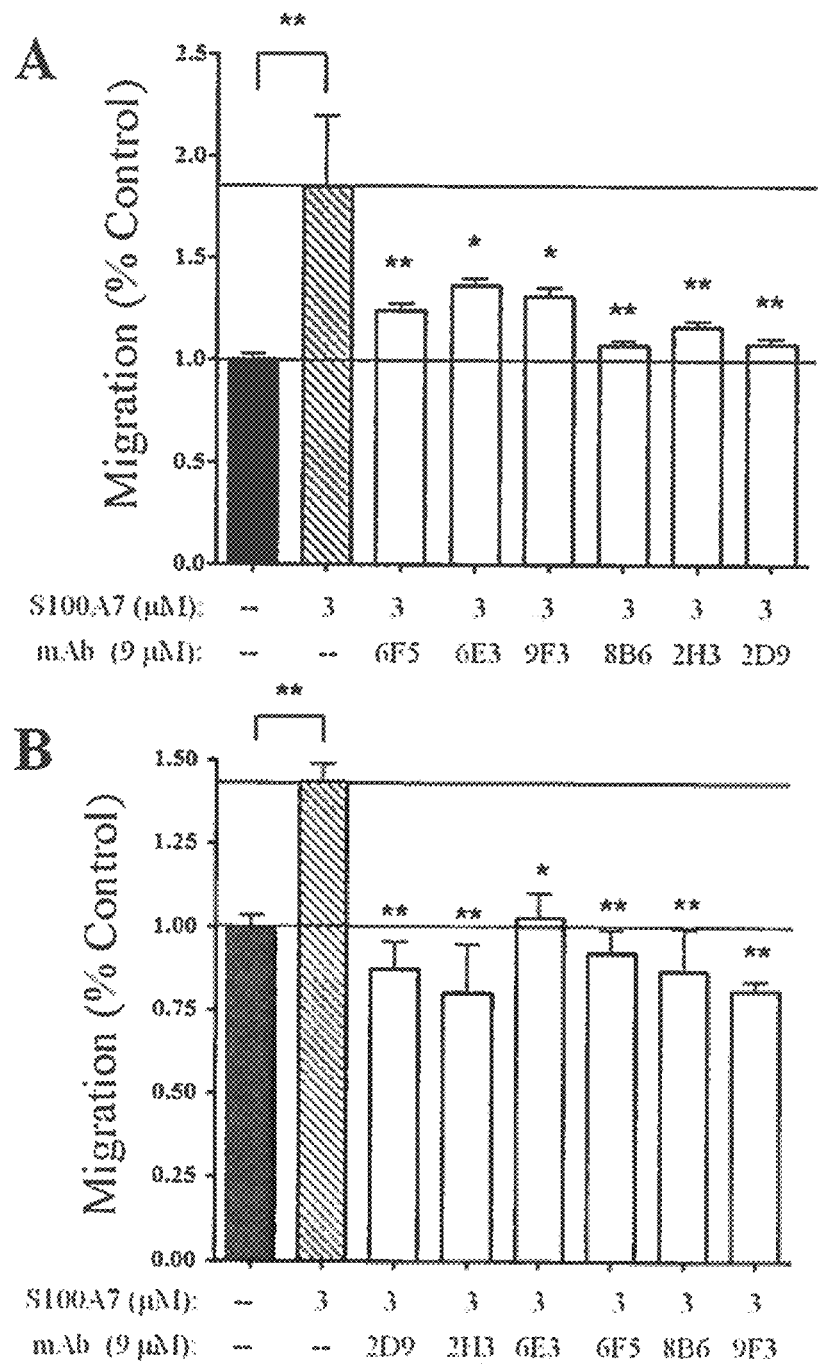
FIG. 8. Inhibitory effect of 2D9, 2H3, 6E3, 6F5, 8B6 and 9F3 monoclonal antibodies on tumor cell migration induced by S100A7 using the human breast adenocarcinoma MDA-MB-231 cell line (A) and human genital carcinoma A431 cell line (B). S100A7 was used at 3 µM and antibodies against S100A7 were used at 9 µM. Graphs show the percentage of migrated cells with respect to the non-stimulated cells (Control). Bars show mean±s-d. *$p<0.05$, ** $p<0.01$ ("Mann-Whitney U test").

FIG. 8A shows that extracellular S100A7 induces a 1.85-fold increase of MDA-MB-231 tumor cell migration with respect to non-stimulated cells. Antibodies showed a statistically significant neutralizing activity of S100A7 effect: 2D9 (90%), 2H3 (80%), 6E3 (57%), 6F5 (72%), 8B6 (91%) and 9F3 (63%), respectively.

FIG. 8B shows that extracellular S100A7 induces a 1.43-fold increase of A431 tumor cell migration with respect to non-stimulated cells. Antibodies showed a statistically significant neutralizing activity of S100A7 effect: 2D9 (100%), 2H3 (100%), 6E3 (72%), 6F5 (100%), 8B6 (100%) and 9F3 (100%), respectively.

Taking into account these results, we can conclude that S100A7 can be an inducer of cell migration, which is related with the in vivo tumor invasion and metastasis, and the monoclonal antibodies of the present invention can block this activity.

Example 13: S100A7 Increases the Migration of HUVEC Endothelial Cells and the Secretion of Matrix Metalloproteinases and the Anti-S100A7 Monoclonal Antibodies Block these Activities The capacity of the endothelial cells to form new blood vessels into the tumor (angiogenesis) is regulated by their capacity to migrate and to secrete matrix metalloproteases which allow them to move more easily.

For migration assay, human vein endothelial cells (HUVEC) were cultured onto 24-well cell culture plates (50.000 cells/well) with light opaque PET membrane filter inserts with 8 µm-pores (prepared according to the manufacturer). Membranes were coated with collagen, type I, from rat tail (upstate) at 15 µg/m for 1 h at 37° C., before seeding the cells.

Medium with soluble S100A7 protein (1 µM) alone or in combination with the antibody 6F5 (3 µM) were added to each well and were cultured for 24 hours. After 24 hours cells were incubated with 5 µM Calcein-AM (Calbiochem) for 15 minutes at 37° C. Fluorescence was measured using a multi-well scanning fluorometer. Comparisons between groups were made using the two-tailed nonparametric Mann Whitney U test. Differences for which P value was less than 0.05 were considered statistically significant.

Figure 9:
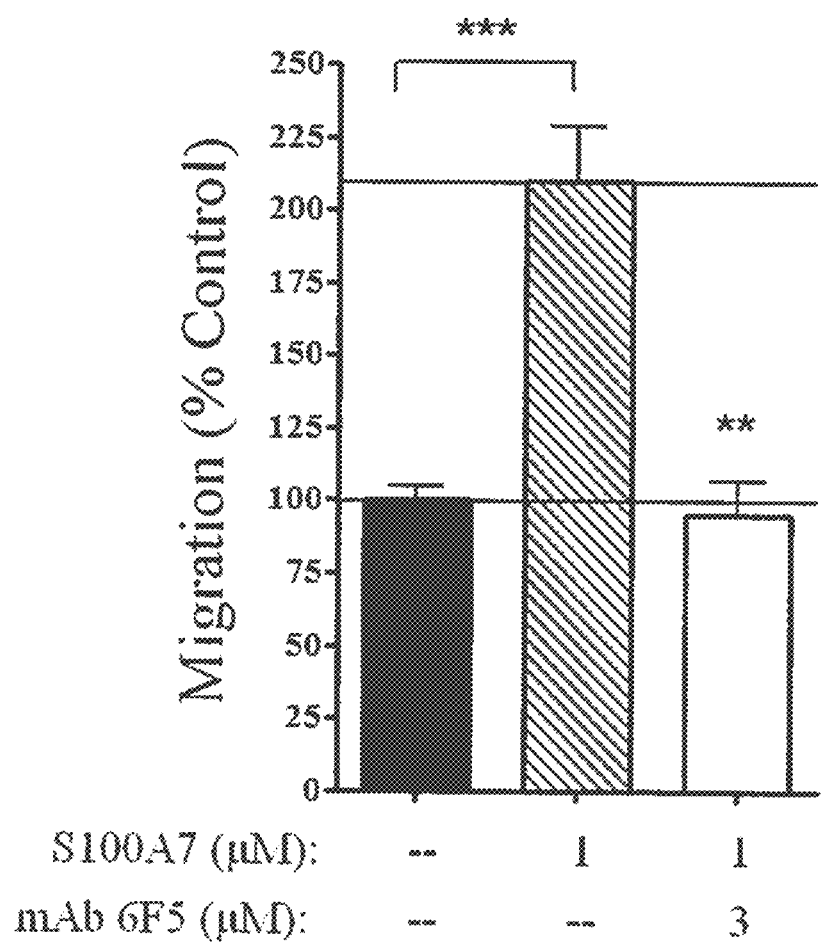
FIG. 9. Inhibitory effect of 6F5 monoclonal antibody on the S100A7-induced migration of HUVEC (Human Endothelial Vein Cells) cell line. S100A7 was used at 1 µM and the antibody against S100A7 was used at 3 µM. Graph shows the percentage of migrated cells with respect to the non-stimulated cells (Control). Bars show mean±s-d. p<0.01, * p<0.001 ("Mann-Whitney U test").

FIG. 9 shows that extracellular S100A7 induces a 2.1-fold increase of endothelial cell migration with respect to non-stimulated cells. The antibody 6F5 showed a statistically significant neutralizing activity of S100A7 effect (100% of neutralization).

Furthermore, the ability of S100A7 to induce the secretion of matrix metalloproteinases in endothelial cells were studied. HUVECs were seeded in 24 well plates at a density of 200.000 cells/well and allowed to attach during 24 h. Then, cells were washed twice with serum free medium and were stimulated with several concentration of recombinant S100A7 during 48 h. For neutralizing assays S300A7 (3 µM) was preincubated with monoclonal antibodies (9 µM) for 4 h prior to the addition to the cells. After 48 hours of stimulation, supernatants were collected and cleared by centrifugation. The same amount of supernatant of each condition (10 µl) were mixed 1:1 with nondenaturing sample buffer (80 mM Tris-HC, pH 6.8, 10% glycerol, 4% SDS, 0.01% bromophenol blue) and resolved on 8% SDS-polyacrilamide gels containing 1 mg/ml of gelatine (Sigma). Then, gels were washed with 2.5% Triton X-100 (Sigma) for 15 minutes, three times, and incubated overnight at 37° C. in pH 7.6 developer buffer (50 mM Tris-HCl, 10 mM $CaCl_2$, and 0.02% (w/v) $NaN_3$). Gels were then stained with Brilliant Blue R® (Sigma) and destained with a solution of 30% methanol and 10% acetic acid. Destained gels were scanned for analysis. Quantification of active MMP9 was performed by using NIH image software, ImageJ.

Figure 10:
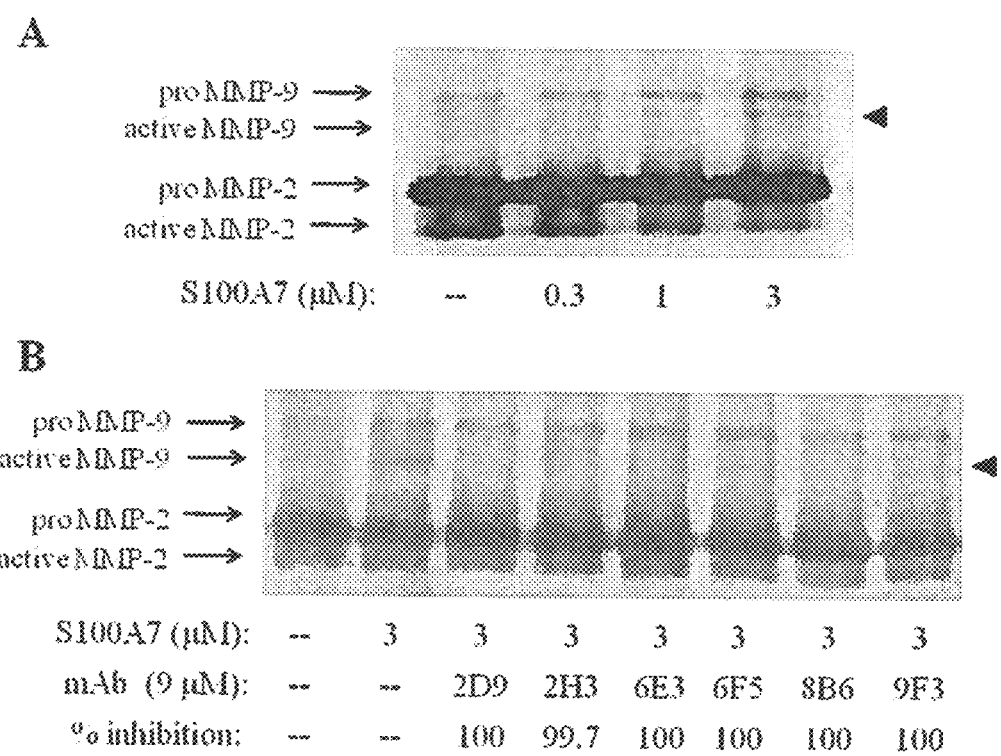
FIG. 10. Monoclonal antibodies 2D9, 2H3, 6E3, 6F5, 8B6 and 9F3 block the S100A7-induced secretion of active forms of MMP9 in HUVEC (Human Endothelial Vein Cells) cell line. (A) Dose-response effect of S100A7 on the secretion of active forms of MMP9. (B) Blockade of the S100A7 effect. S100A7 was used at 3 µM and the indicated antibodies were used at 9 µM. Cell supernatants were analyzed by gelatin zymography after 48 h of incubation with the corresponding stimulus.

FIG. 10A shows a dose-dependent increase of active MMP9 in HUVEC cell supernatants after 48 h of exposure to the indicated concentrations of S100A7. FIG. 10B shows the effect of S100A7 at 3 μM when used alone and the neutralizing effect of the monoclonal antibodies 2D9, 2H3, 6E3, 6F5, 8B6 and 9F3 when used at 9 μM and preincubated with the protein. The densitometry of the bands shows practically 100% inhibition of the S100A7 activity with all the antibodies used.

With this results we can speculate that S100A7 protein has an important role in tumor angiogenesis by inducing a higher mobility of the endothelial cells and an increased secretion of matrix metalloproteinases. The antibodies of the invention are able to block the role of S100A7 in angiogenic processes.

Example 14: S100A7 Increases the Migration of Human Monocytic Cells THP1 and the Anti-S100A7 Monoclonal Antibodies Block this Activity Immune cells infiltration into the tumor have been related with tumor progression, invasion and metastasis.

Human monocytic cells THP-1 were cultured onto 96-well culture plates (50.000 cells/well) with polyester membrane filter inserts with 8 μm-pores (prepared according to the manufacturer). Membranes were coated with collagen, type I, from rat tail (upstate) at 15 μg/ml for 1 h at 37° C., before seeding the cells. Immediately after seeding the cells in the upper chamber, stimulus were placed into the lower compartment diluted in serum free medium and the cells were allowed to migrate for 4 h. Then, the lower compartment media were collected and total migrated cells were counted using a Neubauer chamber. For blocking experiments, 3 μM of S100A7 was preincubated with each monoclonal antibody (9 μM) prior to the addition to the cells.

Figure 11:
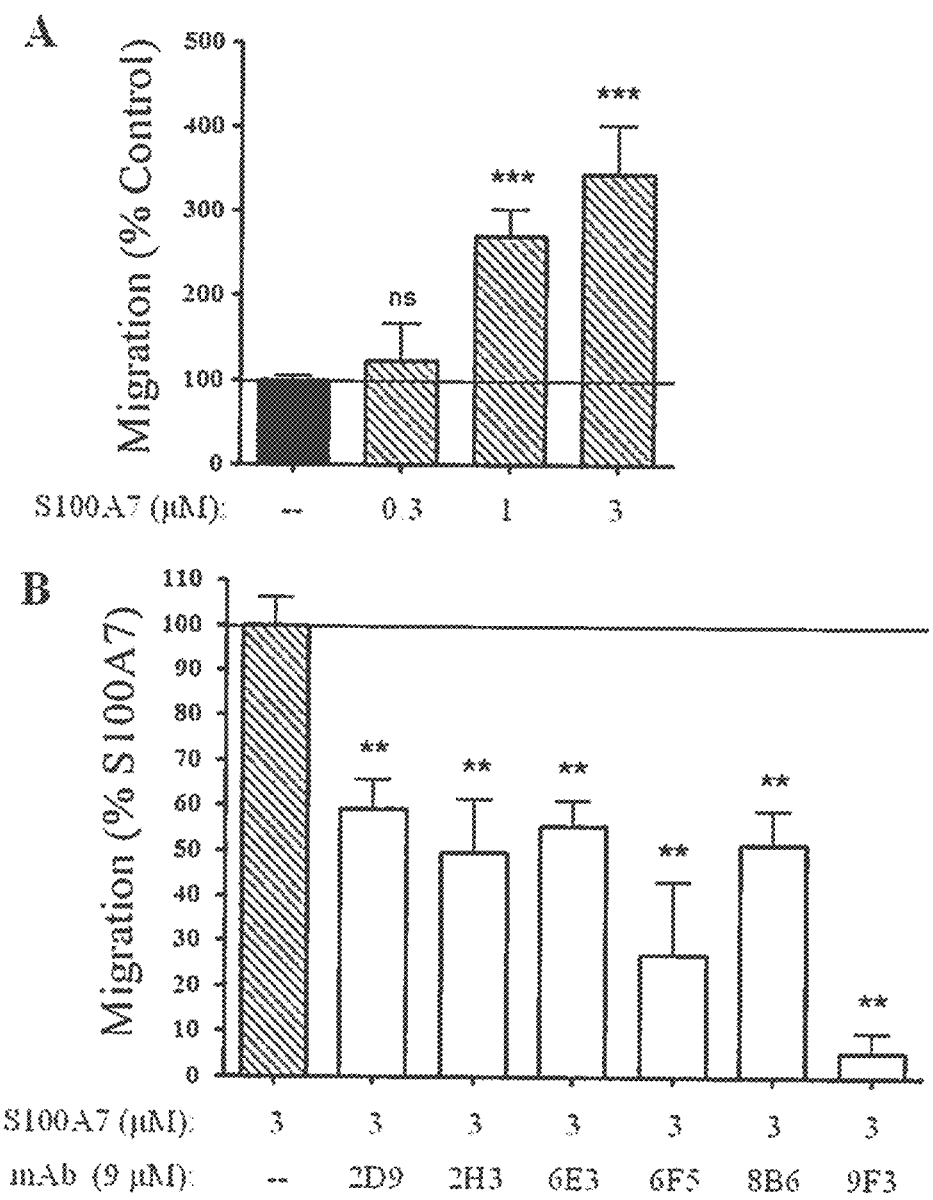
FIG. 11. Monoclonal antibodies 2D9, 2H3, 6E3, 6F5, 8B6 and 9F3 block the S100A7-induced migration of human monocytic cell line THP-1. (A) Dose-response effect of S100A7 on the monocyte migration after 4 h of stimulation. Graph shows the percentage of migrated cells respect to the non-stimulated cells (Control) (B) Blockade of the S100A7 effect. S100A7 was used at 3 µM and the indicated antibodies were used at 9 µM. Graph shows the percentage of stimulated cells with respect to the migration in the presence of S100A7, after removing the basal migration (control). Bars show mean±s-d, ns p>005, p<0.01, * p<0.001 ("Mann-Whitney U test").

FIG. 11A shows a dose-dependent increase of THP-1 cells migration in the presence of several concentrations of recombinant S100A7, when compared with the non-stimulated cells. FIG. 11B shows the neutralizing effect of the monoclonal antibodies 2D9, 2H3, 6E3, 6F5, 8B6 and 9F3 when used at 9 μM and preincubated with the protein (3 μM), achieving a percentage of inhibition of 40%, 50%, 44%, 80%, 48% and 97%, respectively.

Considering these results, we can speculate that S100A7 protein has an important role in inflammatory processes by recruiting inflammatory cells, as monocytes. The antibodies of the invention are able to block the role of S100A7 in inflammatory processes.

Example 15: Monoclonal Antibodies 2D9, 2H3, 6E3, 6F5, 8B6 and 9F3 Block the Development of A431 Tumor Cells in Athimic Nude Mice, without Side Effects Xenograft tumor models are commonly used to assess the response to antiumor agents. Results obtained in these models have been proven to be comparable to that obtained in clinical phases. Tumor xenografts are therefore good models to test the efficacy of antitumoral agents and predict the future response of cancer patients.

A431 tumor cell line (human genital carcinoma) were injected subcutaneously into the right flank of athimic nude mice ($4 \times 10^6$ cells/animal in 100 μl of serum free medium). Tumor volume was followed with the aid of caliper and calculated by using the formula:

$$\text{volume} = (D \times d^2)/2$$

were D is the major axis of the tumor and d is the minor axis. When the mean of the tumor volume reached 120 $mm^3$, animals were sorted into 7 groups (n=10), so that the mean tumor size was similar between groups, and treatments were started. Animals were treated three times a week intraperitoneally with PBS buffer (Control group) or monoclonal antibodies (2D9, 2H3, 6E3, 6F5, 8B6 or 9F3) at 25 mg/Kg/ 100 μl of sterile PBS.

Figure 12:
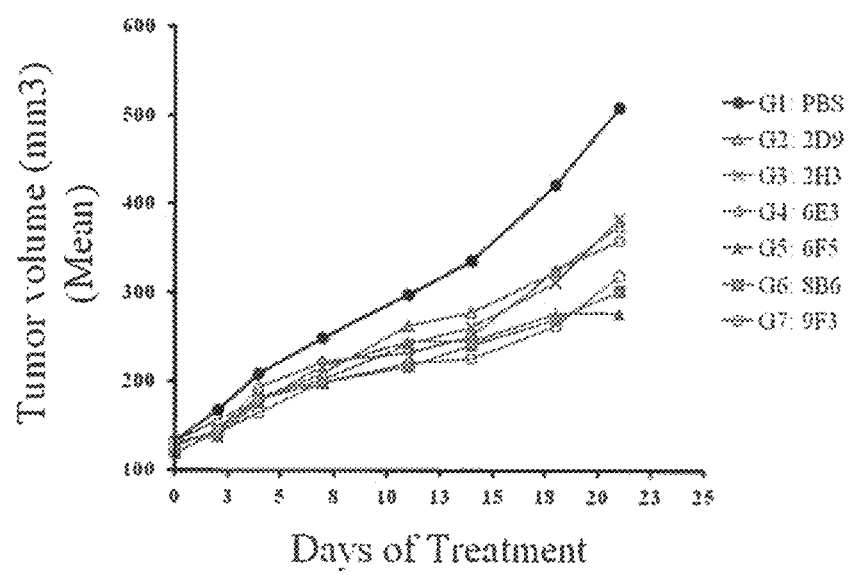
FIG. 12. Effect of monoclonal antibodies 2D9, 2H3, 6E3, 6F5, 8B6 and 9F3 on the in vivo growth of the human genital carcinoma cells A431. Four millions of A431 cells were injected into the right flank of athimic mice and allowed to grow until 120 mm$^3$. Then, mice were sorted into 7 groups of treatment (n=10). Control group received 100 µl of PBS buffer (PBS group) and treated groups received 25 mg/Kg/100 µl of sterile PBS of monoclonal antibodies (2D9, 2H3, 6E3, 6F5, 8B6 and 9F3), three times a week. Tumor volume was followed three times a week with a calliper. (A) Mean of the tumor volume of each group of treatment after the initiation of the treatment. Graph shows the mean of the tumor volume for each group of treatment. (B) TIC ratio (efficacy) of the treated groups compared with the control group (PBS).

Graph in FIG. 12 shows the evolution of the mean of tumor volume for each group along the time since the treatment started (day 0). PBS tumors reached a mean of tumor volume of 507 $mm^3$, whereas treated groups (2D9, 2H3, 6E3, 6F5, 8B6 and 9F3) reached volumes of 375, 383, 359, 275, 301 and 319 $mm^3$, respectively. The T/C ratio for each group is calculated by using the formula: T/C ratio=mean tumor volume treated group/mean tumor volume control group (PBS). Using this formula, the T/C ratios obtained for each group were: 0.73, 0.75, 0.70, 0.54, 0.59 and 0.62, respectively, as showed in the table below the graph in FIG. 12. This result means that all the monoclonal antibodies tested (2D9, 2H3, 6E3, 6F5, 8B6 and 9F3) affected the tumor growth, reducing the tumor volume in 27%, 25%, 30%, 46%, 41% and 38%, respectively.

With these results, the inventors have demonstrated for the first time that a treatment with a monoclonal antibody against S100A7 induces an important decrease in the tumor growth, compared with control group.

Figure 13:
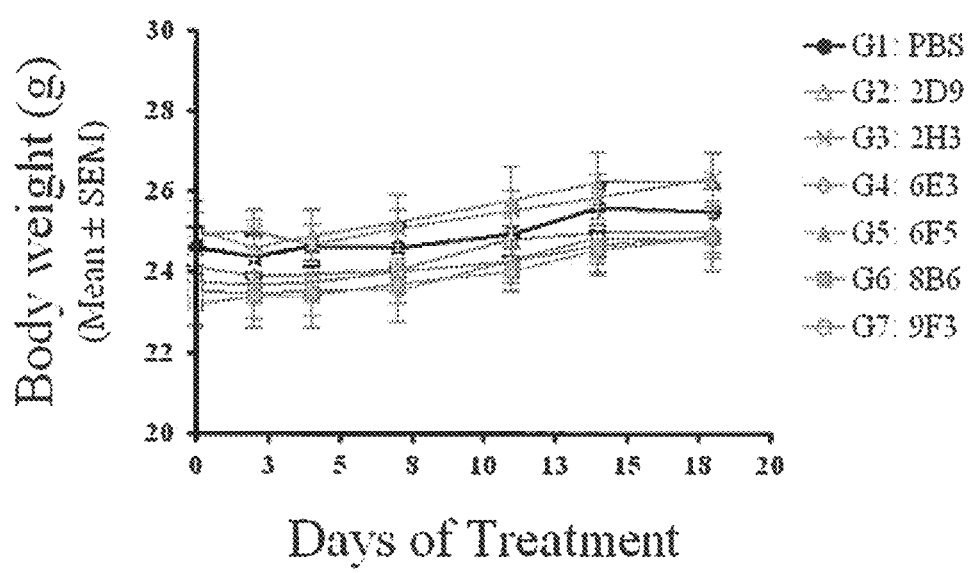
FIG. 13. Monoclonal antibodies 2D9, 2H3, 6E3, 6F5, 8B6 and 9F3 had no side effects when administered in vivo. Four millions of A431 cells were injected into the right flank of athimic mice and tumors were allowed to grow until a mean of 120 mm$^3$. Then, mice were sorted into 7 groups of treatment (n=10). Control group received 100 µl of PBS buffer (PBS group) and treated groups received 500 µg/100 µl of antibody per animal (2D9, 2H3, 6E3, 6F5, 8B6 and 9F3) in PBS buffer, three times a week. Body weight was followed three times a week during the experiment. Graph shows mean±SEM.

Furthermore, the body weight of the control and treated animals was followed, with the aim of detecting possible side effects induced by the antibodies administered. As showed in FIG. 13, no body weight loss was observed in any group. In addition, macroscopic analysis of the animals showed no abnormalities in the organs. No adverse side effects (coordination, paralysis, ataxia, seizures, diarrhea, cachexia, erythema, hypothermia or mortality) were observed in any animal throughout the experiment.

Based on these results the inventors can conclude that the treatment with a monoclonal antibody against S100A7 is not toxic at the dose and schedule used in this experiment.

Biological Material Deposits

The hybridoma which produces 2D9-C43D7-5E6 anti-S100A7 monoclonal antibody was deposited in the European Collection of Cell Cultures (ECACC) (Porton Down, stalisbury, SP4 OJG, United Kingdom) under the conditions stipulated in the Budapest Treaty. It was deposited on 7 Feb. 2013 and the number assigned to said deposit was ECACC 13020701.

The hybridoma which produces 2H3-1A12-5E12-1A4 anti-S100A7 monoclonal antibody was deposited in the European Collection of Cell Cultures (ECACC) (Porton Down, stalisbury, SP4 OJG, United Kingdom) under the conditions stipulated in the Budapest Treaty. It was deposited on 7 Feb. 2013 and the number assigned to said deposit was ECACC 13020702.

The hybridoma which produces 6E3-2D5-1F9-5B4 anti-S100A7 monoclonal antibody was deposited in the European Collection of Cell Cultures (ECACC) (Porton Down, stalisbury, SP4 OJG, United Kingdom) under the conditions stipulated in the Budapest Treaty. It was deposited on 7 Feb. 2013 and the number assigned to said deposit was ECACC 13020703.

The hybridoma which produces 6F5-2F8-2G9-1A2 anti-S100A7 monoclonal antibody was deposited in the European Collection of Cell Cultures (ECACC) (Porton Down, stalisbury, SP4 OJG, United Kingdom) under the conditions stipulated in the Budapest Treaty. It was deposited on 7 Feb. 2013 and the number assigned to said deposit was ECACC 13020704.

The hybridoma which produces 8B6-1A9-5A8-8G2 anti-S100A7 monoclonal antibody was deposited in the European Collection of Cell Cultures (ECACC) (Porton Down, stalisbury, SP4 OJG, United Kingdom) under the conditions stipulated in the Budapest Treaty. It was deposited on 7 Feb. 2013 and the number assigned to said deposit was ECACC 13020705.

The hybridoma which produces 9F3-3E6-2D7-3B3 anti-S100A7 monoclonal antibody was deposited in the European Collection of Cell Cultures (ECACC) (Porton Down, stalisbury, SP4 OJG, United Kingdom) under the conditions stipulated in the Budapest Treaty. It was deposited on 7 Feb. 2013 and the number assigned to said deposit was ECACC 13020706.

The invention claimed is:

1. A method of treatment of a disease which involves expressing of S100A7 protein and which is selected from the group consisting of cancer, a disease associated to an undesired angiogenesis, and a disease associated with inflammation in a subject comprising administering to the subject in need therefore a pharmaceutically effective amount of:
   a) an antibody that binds specifically to the S100A7 protein or of a fragment thereof with capacity for binding to said antigen; or
   b) a conjugate comprising a specific anti-S100A7 monoclonal antibody produced by a hybridoma selected from the group consisting of ECACC 13020701, ECACC 13020702, ECACC 13020703, ECACC 13020704, ECACC 13020705 and ECACC 13020706 or a polypeptide having at least one fragment of the sequence of said monoclonal antibody with capacity for binding to S100A7, said fragment including the sequence of the 6 CDRs of said monoclonal antibody, and a component selected from the group consisting of:
      (a) a cytotoxic agent;
      (b) an antiangiogenic agent;
      (c) an antimetastatic agent;
      (d) an antiproliferative agent; and
      (e) an anti-inflammatory agent,
so as to thereby treat the disease.

2. The method according to claim 1, wherein the cancer is a metastatic cancer or a cancer forming tumor spheres.

3. The method according to claim 1, wherein the tumor is characterized by an increased activation of the NAPK pathway and/or by an increased expression of TNFalpha.

4. The method according to claim 1, wherein the cancer is selected from the group consisting of colorectal carcinoma, fibrosarcoma, epidermoid carcinoma, genital carcinoma and breast cancer.

5. The method according to claim 1, wherein the cancer is digestive carcinoma.

6. The method according to claim 1, wherein the antibody is a monoclonal antibody produced by a hybridoma selected from the group consisting of ECACC 13020701, ECACC 13020702, ECACC 13020703, ECACC 13020704, ECACC 13020705 and ECACC 13020706 or a functional variant of said antibody, said variant including the sequence of the 6 CDRs of said monoclonal antibody.

7. A hybridoma cell line deposited under accession number ECACC 13020701, ECACC 13020702, ECACC 13020703, ECACC 13020704, ECACC 13020705 or ECACC 13020706.

8. A specific anti-S100A7 monoclonal antibody produced by a hybridoma cell line according to claim 7 or a polypeptide having at least one fragment of the sequence of said monoclonal antibody with capacity for binding to S100A7, said fragment including the sequence of the 6 CDRs of said monoclonal antibody.

9. A method for obtaining a monoclonal antibody according to claim 8 which comprises culturing a hybridoma cell line deposited under accession number ECACC 13020701, ECACC 13020702, ECACC 13020703, ECACC 13020704, ECACC 13020705 or ECACC 13020706 in conditions which allow the production of said antibody.

10. A pharmaceutical composition comprising a pharmaceutically effective amount of at least one monoclonal antibody or one polypeptide according to claim 8 and at least one pharmaceutically acceptable excipient.

11. A kit for diagnosing cancer or a disease associated to an undesired angiogenesis or a disease associated with inflammation in a sample which comprises at least one antibody or one polypeptide according to claim 8.

12. A conjugate co rising the monoclonal antibody or the polypeptide according to claim 8 and a second component selected from the group consisting of:
   a) a cytotoxic agent;
   b) an antiangiogenic agent;
   c) an antimetastatic agent;
   d) an antiproliferative agent; and
   e) an antiinflammatory agent.

13. An in vitro method for the diagnosis of, or for monitoring the progression of, digestive or genital carcinoma expressing S100A7 protein or of a non-cancerous disease expressing S100A7 protein associated with undesired angiogenesis or with inflammation in a subject which comprises:
   a) detecting the levels of the S100A7 protein in a biofluid of said subject by means of:
      i. an antibody that binds specifically to the S100A7 protein or of a fragment thereof with capacity for binding to said antigen; or
      ii. a specific anti-S100A7 monoclonal antibody produced by a hybridoma selected from the group consisting of ECACC 13020701, ECACC 13020702, ECACC 13020703, ECACC 13020704, ECACC 13020705 and ECACC 13020706 or a functional variant of said antibody, said variant including the sequence of the 6 CDRs of said monoclonal antibody, and
   b) comparing said levels with a reference value,
   wherein increased levels of the S100A7 protein with respect to the reference value are indicative of the subject suffering from digestive or genital carcinoma expressing the S100A7 protein or from a non-cancerous disease expressing the S100A7 protein associated with undesired angiogenesis or with inflammation.

14. The method according to claim 13, wherein the digestive carcinoma expressing the S100A7 protein is colorectal carcinoma.

15. The in vitro method of claim 13 for monitoring the progression of digestive or genital carcinoma expressing S100A7 protein or of a non-cancerous disease expressing S100A7 protein associated with undesired angiogenesis or with inflammation in a subject, wherein the reference value in b) for said protein is obtained from the same subject at an earlier time point of the disease, wherein a decrease of the levels of the S100A7 protein with respect to the reference value is indicative that the digestive or genital carcinoma expressing the S100A7 protein or the non-cancerous disease expressing the 8100A7 protein associated with undesired angiogenesis or with inflammation is not in progression, or wherein an increase of the levels of the S100A7 protein with respect to the reference value is indicative that the digestive or the genital carcinoma expressing the S100A7 protein or the non-cancerous disease expressing the S100A7 protein associated with undesired angiogenesis or with inflammation is in progression.

16. The method according to claim 15, wherein the detection is carried out by means of a monoclonal antibody produced by a hybridoma selected from the group consisting of ECACC 13020701, ECACC 13020702, ECACC 13020703, ECACC 13020704, ECACC 13020705 and ECACC 13020706 or a functional variant of said antibody, said variant including the sequence of the 6 CDRs of said monoclonal antibody.

17. The method according to claim 15, wherein the digestive carcinoma expressing the S100A7 protein is colorectal carcinoma.

* * * * *

```
                            SEQUENCE LISTING

<160> NUMBER OF SEQ ID NOS: 4

<210> SEQ ID NO 1
<211> LENGTH: 104
<212> TYPE: PRT
<213> ORGANISM: Artificial Sequence
<220> FEATURE:
<223> OTHER INFORMATION: S100A7 fusion protein

<400> SEQUENCE: 1

Gly Ser His Met Ser Asn Thr Gln Ala Glu Arg Ser Ile Ile Gly Met
1               5                   10                  15

Ile Asp Met Phe His Lys Tyr Thr Arg Arg Asp Asp Lys Ile Glu Lys
                20                  25                  30

Pro Ser Leu Leu Thr Met Met Lys Glu Asn Phe Pro Asn Phe Leu Ser
            35                  40                  45

Ala Cys Asp Lys Lys Gly Thr Asn Tyr Leu Ala Asp Val Phe Glu Lys
        50                  55                  60

Lys Asp Lys Asn Glu Asp Lys Lys Ile Asp Phe Ser Glu Phe Leu Ser
65                  70                  75                  80

Leu Leu Gly Asp Ile Ala Thr Asp Tyr His Lys Gln Ser His Gly Ala
                85                  90                  95

Ala Pro Cys Ser Gly Gly Ser Gln
            100

<210> SEQ ID NO 2
<211> LENGTH: 42
<212> TYPE: DNA
<213> ORGANISM: Artificial Sequence
<220> FEATURE:
<223> OTHER INFORMATION: forward primer

<400> SEQUENCE: 2
actcacatat gagcaacact caagctgaga ggtccataat ag              42

<210> SEQ ID NO 3
<211> LENGTH: 42
<212> TYPE: DNA
<213> ORGANISM: Artificial Sequence
<220> FEATURE:
<223> OTHER INFORMATION: reverse primer

<400> SEQUENCE: 3
actcatgagc tcatcctggc tgcccccgga acagggcgct gc              42

<210> SEQ ID NO 4
<211> LENGTH: 6
<212> TYPE: PRT
```

```
<213> ORGANISM: Artificial Sequence
<220> FEATURE:
<223> OTHER INFORMATION: Trombin protease recognition sequence in S100A7
      fusion protein

<400> SEQUENCE: 4

Leu Val Pro Arg Gly Ser
1               5
```